(12) United States Patent
Banga et al.

(10) Patent No.: US 8,603,466 B2
(45) Date of Patent: Dec. 10, 2013

(54) AGONIST ANTIBODIES AGAINST TSHR

(75) Inventors: Jasvinder-Paul Singh Banga, London (GB); Jacqueline Ann Gilbert, London (GB); Deborah Dunn-Walters, London (GB); Carolyn Padoa, Johannesburg (ZA)

(73) Assignee: King's College London, London ( * ) Notice: Subject to any disclaimer, the term of this patent is extended or adjusted under 35 U.S.C. 154(b) by 645 days.

(21) Appl. No.: 12/294,760

(22) PCT Filed: Mar. 29, 2007

(86) PCT No.: PCT/GB2007/001139
§ 371 (c)(1),
(2), (4) Date: Jun. 28, 2010

(87) PCT Pub. No.: WO2007/110648
PCT Pub. Date: Oct. 4, 2007

(65) Prior Publication Data
US 2010/0266493 A1    Oct. 21, 2010

(30) Foreign Application Priority Data

Mar. 29, 2006  (GB) .................................. 0606276.4
Apr. 12, 2006  (GB) .................................. 0607376.1

(51) Int. Cl.
*A61K 39/395*    (2006.01)

(52) U.S. Cl.
USPC .................. 424/130.1; 424/133.1; 424/138.1; 424/143.1; 424/155.1; 424/174.1; 424/178.1; 530/387.1; 530/387.3; 530/387.7; 530/388.22; 530/391.3; 530/391.7; 435/69.1; 435/320.1; 435/325; 435/334; 536/23.5

(58) Field of Classification Search
USPC ............. 530/350, 38.1, 387.3, 388.22, 387.1, 530/387, 7, 388.8, 391.3, 391.7; 435/69.1, 435/325, 334; 536/23.5; 424/130.1, 133.1, 424/138.1, 143.1, 155.1, 174.1, 178.1
See application file for complete search history.

(56) References Cited

U.S. PATENT DOCUMENTS 7,090,842 B1 *  8/2006  Chatterjee et al. ......... 424/131.1
2002/0098190 A1    7/2002  Chatterjee et al.

FOREIGN PATENT DOCUMENTS

WO    01/02531 A1    1/2001
WO    03/018632 A2   3/2003

OTHER PUBLICATIONS

Ando et al. (Mol. Endocrinol. Sep. 2001; 15 (9): 1529-38).*
Greenspan et al. (Nature Biotechnology. 1999; 7: 936-937).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Costagliola, Sabine et al., Delineation of the Discontinuous-Conformational Epitope of a Monoclonal Antibody Displaying Full in Vitro and in Vivo Thyrotropin Activity, Molecular Endocrinology, Dec. 2004, pp. 3020-3034, vol. 18, No. 12.
McLachlan, Sandra M. et al, "Thyroid stimulating monoclonal antibodies: overcoming the road blocks and the way forward", Clinical Endocrinology, Jul. 2004, pp. 10-18, vol. 61, No. 1.
Ando, Takao et al, "A monoclonal thyroid-stimulating antibody", The Journal of Clinical Investigation, Dec. 2002, pp. 1667-1674, vol. 110, No. 11.
Gilbert, Jacqueline A. et al., "Monoclonal Pathogenic Antibodies to the Thyroid-Stimulating Hormone Receptor in Graves' Disease with Potent Thyroid-Stimulating Activity but Differential Blocking Activity Activate Multiple Signaling Pathways", The Journal of Immunology, The American Association of Immunologists, Inc., Apr. 2006, pp. 5084-5092, vol. 176, No. 8.

* cited by examiner

*Primary Examiner* — Stephen Rawlings
(74) *Attorney, Agent, or Firm* — Banner & Witcoff, Ltd.

(57) ABSTRACT

The invention provides antibodies that bind the thyroid stimulating hormone receptor (TSHR), especially in humans, and their uses in diagnostic and therapeutic roles. The invention also provides hybridomas for producing such antibodies.

39 Claims, 27 Drawing Sheets

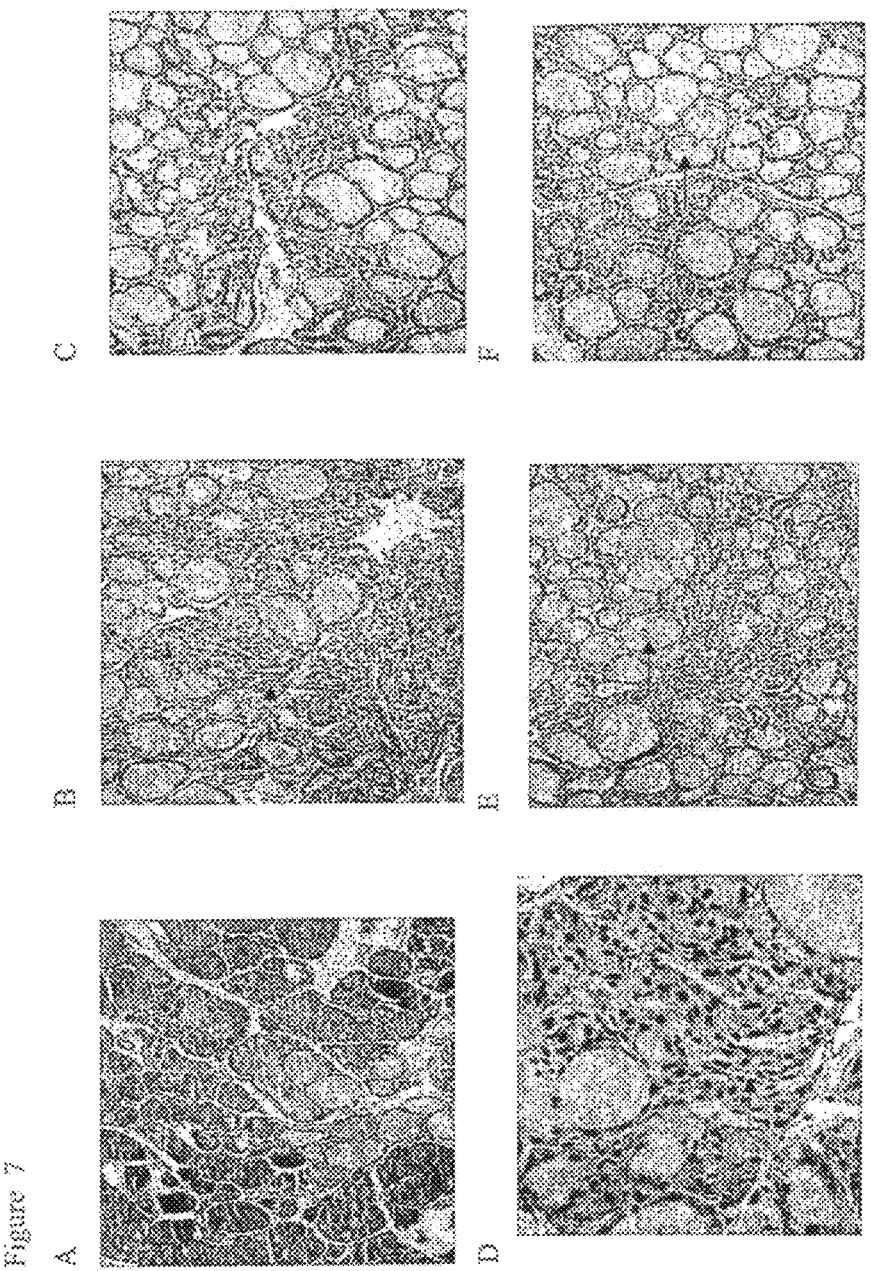

Figure 8

AYTMN

Figure 9

AYTMD

Figure 10

LINPYNGGTNYNQEFEG

Figure 11

RDWDYFDY

Figure 12

KASQNVGTFVA

Figure 13

SASNRYT

Figure 14

RQYSSYPYT

Figure 15

Figure 1A:
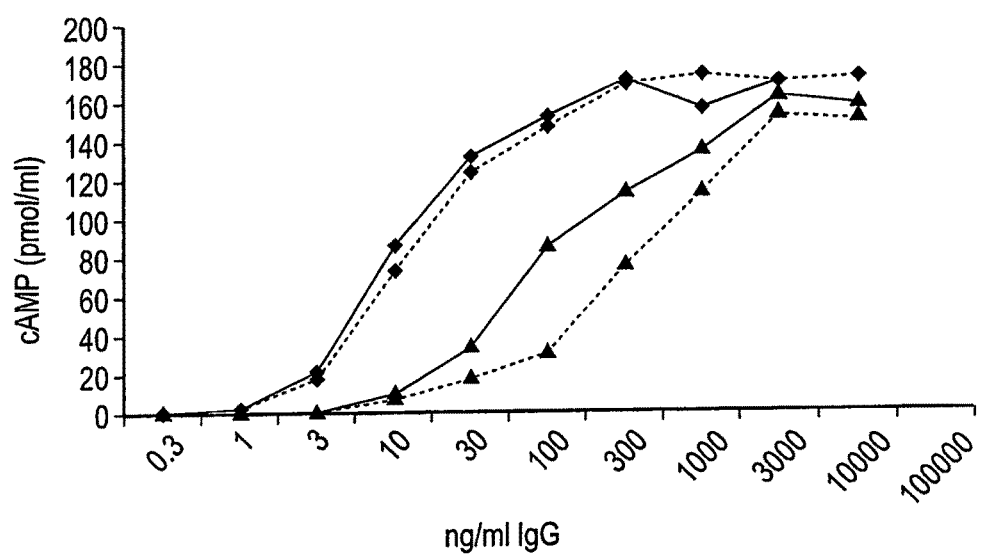

EVQLQQSGPELVKPGASMKISCKASGYSFSAYTMNWVKQSHGKNLEWIGLINPYNG
GTNYNQEFEGKATLTVNKSSNTAFMELLSLTSDDSAVYYCARRDWDYFDYWGQGT
TLTVSSAKTTTPSVYPLAPGCGDTTGSSVTLGCLVKGYFPESVTVTWNSGSLSSSVHT
FPALLQSGLYTMSSSVTVPSSTWPSQTVTCSVAHPASSTKVDKKIETRC

Figure 16

EVQLQQSGPELVKPGASMKISCKASGYSFFAYTMNWVKQSHGKNLEWIGLINPYNG
GTNYNQEFEGKATLTVNKSSNTAFMELLSLTSDDSAVYYCARRDWDYFDYWGQGT
TLTVSSAKTTPPSVYPLAPGCGDTTGSSVTLGCLVKGYFPESVTVTWNSGSLSSSVHT
FPALLQSGLYTMSSSVTVPSSTWPSQTVTCSVAHPASSTKVDKKIETRC

Figure 17

EVQLQQSGPELVKPGASMKISCKASGYSFSAYTMDWVKQSHGKNLEWIGLINPYNG
GTNYNQEFEGKATLTVNKSSNTAFMELLSLTSDDSAVYYCARRDWDYFDYWGQGT
TLTVSSAKTTPPSVYPLAPGCGDTTGSSVTLGCLVKGYFPESVTVTWNSGSLSSSVHT
FPALLQSGLYTMSSSVTVPSSTWPSQTVTCSVAHPASSTKVDRKLRRVVKGEFCRYP

Figure 18

EVQLQQSGPELVKPGASMKISCKASGYSFSAYTMNWVKQSHGKNLEWIGLINPYNG
GTNYNQEFEGKATLTVNKSSNTAFMELLSLTSDGSAVYYCARRDWDYFDYWGQGT
TLTVSSAKTTPPSVYPLAPGCGDTTGSSVTLGCLVKGYFPESVTVTWNSGSLSSSVHT
FPALLQSGLYTMSSSVTVPSSTWPSQTVTCSVAHPASSTKVDKKIETRC

Figure 19

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEIKRADAAP
TVSIFPPSSEQLTSGGASVVCFLNNFYPKDINVKWKIVGSERQNGVLNSWTDQDSKD
STYSMSSTLTLTKDEYERHNSYTCEATHKTSTSPIVKSFNRNETRC

Figure 20

EVQLQQSGPELVKPGASMKISCKASGYSFSAYTMNWVKQSHGKNLEWIGLINPYNG
GTNYNQEFEGKATLTVNKSSNTAFMELLSLTSDDSAVYYCARRDWDYFDYWGQGT
TLTVSS

Figure 21

EVQLQQSGPELVKPGASMKISCKASGYSFFAYTMNWVKQSHGKNLEWIGLINPYNG
GTNYNQEFEGKATLTVNKSSNTAFMELLSLTSDDSAVYYCARRDWDYFDYWGQGT
TLTVSS

Figure 22

EVQLQQSGPELVKPGASMKISCKASGYSFSAYTMDWVKQSHGKNLEWIGLINPYNG
GTNYNQEFEGKATLTVNKSSNTAFMELLSLTSDDSAVYYCARRDWDYFDYWGQGT
TLTVSS

Figure 23

EVQLQQSGPELVKPGASMKISCKASGYSFSAYTMNWVKQSHGKNLEWIGLINPYNG
GTNYNQEFEGKATLTVNKSSNTAFMELLSLTSDGSAVYYCARRDWDYFDYWGQGT
TLTVSS

Figure 24

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEI

Figure 25

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEIGGGGSGG
GGSGGGGSEVQLQQSGPELVKPGASMKISCKASGYSFSAYTMNWVKQSHGKNLEWI
GLINPYNGGTNYNQEFEGKATLTVNKSSNTAFMELLSLTSDDSAVYYCARRDWDYF
DYWGQGTTLTVSS

Figure 26

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEIGGGGSGG
GGSGGGGSEVQLQQSGPELVKPGASMKISCKASGYSFFAYTMNWVKQSHGKNLEWI
GLINPYNGGTNYNQEFEGKATLTVNKSSNTAFMELLSLTSDDSAVYYCARRDWDYF
DYWGQGTTLTVSS

Figure 27

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEIGGGGSGG
GGSGGGGSEVQLQQSGPELVKPGASMKISCKASGYSFSAYTMDWVKQSHGKNLEWI
GLINPYNGGTNYNQEFEGKATLTVNKSSNTAFMELLSLTSDDSAVYYCARRDWDYF
DYWGQGTTLTVSS

Figure 28

DIVMTQSQKFMSTSVGDRVSIICKASQNVGTFVAWYQQKPGQSPKLLVYSASNRYT
GVPDRFTGSGSGTDFTLTINNMQSEDLADYFCRQYSSYPYTFGGGTKLEIGGGGSGG
GGSGGGGSEVQLQQSGPELVKPGASMKISCKASGYSFSAYTMNWVKQSHGKNLEWI
GLINPYNGGTNYNQEFEGKATLTVNKSSNTAFMELLSLTSDGSAVYYCARRDWDYF
DYWGQGTTLTVSS

Figure 29

GGGGSGGGGSGGGGS

Figure 30

LINPYNGGTSYNQKFED

Figure 31

LINPYNGGTNYNQKFED

Figure 32

KASQNVGTALA

Figure 33

SASNRNT

Figure 34

QQYSSYPYT

Figure 35

EVQLQQSGPELVKPGASMKISCKASGYSFTAYTMNWVKQTHGKNLEWIGLINPYNG
GTSYNQKFEDKATLTVDKSSNTAYMDLLSLTSEDSAVYYCARRDWDYFDYWGQGT
TLTVSSAKTTAPAVYPLAPVCGDTTGSSVTLGCLVKGYFPEPVTLTWNSGSLSSGVH
TFPAVLQSDLYTLSSSVTVTSSTWPSQSITCNVAHPASSTKVDKKIETRC

Figure 36

EVQLQQSGPELVKPGASMKISCKASGYSFTAYTMNWVKQTHGKNLEWIGLINPYNG
GTNYNQKFEDKATLTVDKSSNTAYMDLLSLTSEDSAVYYCARRDWDYFDYWGQG
TTLTVSSAKTTAPSVYPLAPVCGDTTGSSVTLGCLVKGYFPEPVTLTWNSGSLSSGVH
TFPAVLQSDLYTLSSSVTVTSSTWPSQSITCNVAHPASSTKVDKKIETRC

Figure 37

EVQLQQSGPELVKPGASMKISCKASGYSFTAYTMNWVKQTHGKNLEWIGLINPYNG
GTNYNQKFEDKATLTVDKSSNTAYMDLLSLTSEDSAVYYCARRDWDYFDYWGQG
TTLTVSSAKTTAPSVYPLAPVCGDTTGSSVTLGCLVKGYFPEPVTLTWNSGSLSSGVH
T

Figure 38

DVVMTQSQKFLSTSAGDRVSISCKASQNVGTALAWYQQKPGQSPKLLIYSASNRNT
GVPDRFTGRGFGTDFTLTISNMQSEDLADYFCQQYSSYPYTFGGGTRLEIKRADAAP
TVSIFPPSSEQLTSGGASVVCFLNNFYPKDINVKWKIDGSERQNGVLNSWTDQDSKD
STYSMSSTLTLTKDEYERHNSYTCEATHKTSTSPIVKSFNRNETRC

Figure 39

EVQLQQSGPELVKPGASMKISCKASGYSFTAYTMNWVKQTHGKNLEWIGLINPYNG
GTSYNQKFEDKATLTVDKSSNTAYMDLLSLTSEDSAVYYCARRDWDYFDYWGQGT
TLTVSS

Figure 40

EVQLQQSGPELVKPGASMKISCKASGYSFTAYTMNWVKQTHGKNLEWIGLINPYNG
GTNYNQKFEDKATLTVDKSSNTAYMDLLSLTSEDSAVYYCARRDWDYFDYWGQG
TTLTVSS

Figure 41

DVVMTQSQKFLSTSAGDRVSISCKASQNVGTALAWYQQKPGQSPKLLIYSASNRNT
GVPDRFTGRGFGTDFTLTISNMQSEDLADYFCQQYSSYPYTFGGGTRLEI

Figure 42

DVVMTQSQKFLSTSAGDRVSISCKASQNVGTALAWYQQKPGQSPKLLIYSASNRNT
GVPDRFTGRGFGTDFTLTISNMQSEDLADYFCQQYSSYPYTFGGGTRLEIGGGGSGG
GGSGGGGSEVQLQQSGPELVKPGASMKISCKASGYSFTAYTMNWVKQTHGKNLEW
IGLINPYNGGTSYNQKFEDKATLTVDKSSNTAYMDLLSLTSEDSAVYYCARRDWDY
FDYWGQGTTLTVSS

Figure 43

DVVMTQSQKFLSTSAGDRVSISCKASQNVGTALAWYQQKPGQSPKLLIYSASNRNT
GVPDRFTGRGFGTDFTLTISNMQSEDLADYFCQQYSSYPYTFGGGTRLEIGGGGSGG
GGSGGGGSEVQLQQSGPELVKPGASMKISCKASGYSFTAYTMNWVKQTHGKNLEW
IGLINPYNGGTNYNQKFEDKATLTVDKSSNTAYMDLLSLTSEDSAVYYCARRDWDY
FDYWGQGTTLTVSS

Figure 44 gcctacaccatgaac

Figure 45 gcctacaccatggac

Figure 46 cttattaatccttacaatggtggtactaactacaaccaggagttcgagggc

Figure 47 agggactgggactactttgactac

Figure 48 aaggccagtcagaatgtgggtacttttgtagcc

Figure 49 tcggcatccaatcggtacact

Figure 50 cggcaatatagcagctatccgtacacg

Figure 51

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCAGCCAAAACAACAACCCCATCAGTCTATCCAC
TGGCCCCTGGGTGTGGAGATACAACTGGTTCCTCCGTGACTCTGGGATGCCTGGT
CAAGGGCTACTTCCCTGAGTCAGTGACTGTGACTTGGAACTCTGGATCCCTGTCC
AGCAGTGTGCACACCTTCCCAGCTCTCCTGCAGTCTGGACTCTACACTATGAGCA
GCTCAGTGACTGTCCCCTCCAGCACCTGGCCAAGTCAGACCGTCACCTGCAGCGT
TGCTCACCCAGCCAGCAGCACCAAGGTGGACAAGAAAATTGAGACGCGTTGT

Figure 52

GAGGTCCAGCTGCAACAGTCTGGACCTGAGCTGGTGAAGCCTGGAGCTTCAATG
AAGATATCCTGCAAGGCTTCTGGTTACTCATTCTTTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCAGCCAAAACAACACCCCATCAGTCTATCCAC
TGGCCCCTGGGTGTGGAGATACAACTGGTTCCTCCGTGACTCTGGGATGCCTGGT
CAAGGGCTACTTCCCTGAGTCAGTGACTGTGACTTGGAACTCTGGATCCCTGTCC
AGCAGTGTGCACACCTTCCCAGCTCTCCTGCAGTCTGGACTCTACACTATGAGCA
GCTCAGTGACTGTCCCCTCCAGCACCTGGCCAAGTCAGACCGTCACCTGCAGCGT
TGCTCACCCAGCCAGCAGCACCAAGGTGGACAAGAAAATTGAGACGCGTTGT

Figure 53

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGGACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCAGCCAAAACAACACCCCATCAGTCTATCCAC
TGGCCCCTGGGTGTGGAGATACAACTGGTTCCTCCGTGACTCTGGGATGCCTGGT
CAAGGGCTACTTCCCTGAGTCAGTGACTGTGACTTGGAACTCTGGATCCCTGTCC
AGCAGTGTGCACACCTTCCCAGCTCTCCTGCAGTCTGGACTCTACACTATGAGCA
GCTCAGTGACTGTCCCCTCCAGCACCTGGCCAAGTCAGACCGTCACCTGCAGCGT
TGCTCACCCAGCCAGCAGCACCAAGGTGGACA:GAAAATTGAGACGCGTTGTCAA
GGGCGAATTCTGCAGATATCCAT

Figure 54

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGGCTC
TGCAGTCTATTACTGTGCGAGAAGGGACTGGGACTACTTTGACTACTGGGGCCAA
GGCACCACTCTCACAGTCTCCTCAGCCAAAACAACACCCCATCAGTCTATCCAC
TGGCCCCTGGGTGTGGAGATACAACTGGTTCCTCCGTGACTCTGGGATGCCTGGT
CAAGGGCTACTTCCCTGAGTCAGTGACTGTGACTTGGAACTCTGGATCCCTGTCC
AGCAGTGTGCACACCTTCCCAGCTCTCCTGCAGTCTGGACTCTACACTATGAGCA
GCTCAGTGACTGTCCCCTCCAGCACCTGGCCAAGTCAGACCGTCACCTGCAGCGT
TGCTCACCCAGCCAGCAGCACCAAGGTGGACAAGAAAATTGAGACGCGTTGT

Figure 55

GACATTGTGATGACCCAGTCTCAAAAATTCATGTCCACATCAGTAGGAGACAGG
GTCAGCATCATTTGCAAGGCCAGTCAGAATGTGGGTACTTTTGTAGCCTGGTATC
AACAGAAACCAGGACAATCTCCTAAACTACTGGTTTACTCGGCATCCAATCGGTA
CACTGGAGTCCCTGATCGCTTCACAGGCAGTGGATCTGGGACAGATTTCACTCTC
ACCATCAACAATATGCAGTCTGAAGACCTGGCAGATTATTTCTGCCGGCAATATA
GCAGCTATCCGTACACGTTCGGAGGGGGGACCAAGCTAGAAATAAAACGGGCTG
ATGCTGCACCAACTGTATCCATCTTCCCACCATCCAGTGAGCAGTTAACATCTGG
AGGTGCCTCAGTCGTGTGCTTCTTGAACAACTTCTACCCCAAAGACATCAATGTC
AAGTGGAAGATTGTTGGCAGTGAACGACAAAATGGCGTCCTGAACAGTTGGACT
GATCAGGACAGCAAAGACAGCACCTACAGCATGAGCAGCACCCTCACGTTGACC
AAGGACGAGTATGAACGACATAACAGCTATACCTGTGAGGCCACTCACAAGACA
TCAACTTCACCCATTGTCAAGAGCTTCAACAGGAATGAGACGCGTTGT

Figure 56

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCA

Figure 57

GAGGTCCAGCTGCAACAGTCTGGACCTGAGCTGGTGAAGCCTGGAGCTTCAATG
AAGATATCCTGCAAGGCTTCTGGTTACTCATTCTTTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCA

Figure 58

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGGACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGACTC
TGCAGTCTATTACTGTGCGAGAAGGGACTGGGACTACTTTGACTACTGGGGCCAA
GGCACCACTCTCACAGTCTCCTCA

Figure 59

GAGGTCCAGCTGCAACAGTCTGGACCTGAGCTGGTGAAGCCTGGAGCTTCAATG
AAGATATCCTGCAAGGCTTCTGGTTACTCATTCTCTGCCTACACCATGAACTGGG
TGAAGCAGAGCCATGGAAAGAACCTTGAGTGGATTGGACTTATTAATCCTTACA
ATGGTGGTACTAACTACAACCAGGAGTTCGAGGGCAAGGCCACTTTAACTGTAA
ACAAGTCATCCAACACAGCCTTCATGGAGCTCCTCAGTCTGACATCTGACGGCTC
TGCAGTCTATTACTGTGCGAGAAGGGACTGGGACTACTTTGACTACTGGGGCCAA
GGCACCACTCTCACAGTCTCCTCA

Figure 60

GACATTGTGATGACCCAGTCTCAAAAATTCATGTCCACATCAGTAGGAGACAGG
GTCAGCATCATTTGCAAGGCCAGTCAGAATGTGGGTACTTTTGTAGCCTGGTATC
AACAGAAACCAGGACAATCTCCTAAACTACTGGTTTACTCGGCATCCAATCGGTA
CACTGGAGTCCCTGATCGCTTCACAGGCAGTGGATCTGGGACAGATTTCACTCTC
ACCATCAACAATATGCAGTCTGAAGACCTGGCAGATTATTTCTGCCGGCAATATA
GCAGCTATCCGTACACGTTCGGAGGGGGGACCAAGCTAGAAATA

Figure 61 cttattaatccatacaatggtggtactagctacaaccagaagttcgaggac

Figure 62 cttattaatccttacaatggtggtactaactacaaccagaagttcgaggac

Figure 63 aaggccagtcagaatgtgggtactgctttagcc

Figure 64 tcggcatccaatcggaacact

Figure 65 cagcaatatagcagctatccttacacg

Figure 66

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCATACA
ATGGTGGTACTAGCTACAACCAGAAGTTCGAGGACAAGGCCACATTAACTGTTG
ACAAGTCATCCAACACAGCCTACATGGACCTCCTCAGTCTGACATCTGAGGACTC
TGCAGTCTATTATTGTGCAAGAAGGGACTGGGACTACTTTGACTACTGGGGCCAA
GGCACCACTCTCACAGTCTCCTCAGCCAAAACAACAGCCCCAGCGGTCTATCCAC
TGGCCCCTGTGTGTGGAGATACGACTGGCTCCTCGGTGACTCTAGGATGCCTGGT
CAAGGGTTATTTCCCTGAGCCAGTGACCTTGACCTGGAACTCTGGATCCCTGTCC
AGTGGTGTGCACACCTTCCCAGCTGTCCTGCAGTCTGACCTCTACACCCTCAGCA
GCTCAGTGACTGTAACCTCGAGCACCTGGCCCAGCCAGTCCATCACCTGCAATGT
GGCCCACCCGGCAAGCAGCACCAAGGTGGACAAGAAAATTGAGACGCGTTGT

Figure 67

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCTTACAA
TGGTGGTACTAACTACAACCAGAAGTTCGAGGACAAGGCCACATTAACTGTCGA
CAAGTCATCCAACACAGCCTACATGGACCTCCTCAGTCTGACATCTGAGGACTCT
GCAGTCTATTATTGTGCAAGAAGGGACTGGGACTACTTTGACTACTGGGGCCAAG
GCACCACTCTCACAGTCTCCTCAGCCAAAACAACAGCCCCATCGGTCTATCCACT
GGCCCCTGTGTGTGGAGATACAACTGGCTCCTCGGTGACTCTAGGATGCCTGGTC
AAGGGTTATTTCCCTGAGCCAGTGACCTTGACCTGGAACTCTGGATCCCTGTCCA
GTGGTGTGCACACCTTCCCAGCTGTCCTGCAGTCTGACCTCTACACCCTCAGCAG
CTCAGTGACTGTAACCTCGAGCACCTGGCCCAGCCAGTCCATCACCTGCAATGTG
GCCCACCCGGCAAGCAGCACCAAGGTGGACAAGAAAATTGAGACGCGTTGT

Figure 68

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCTTACAA
TGGTGGTACTAACTACAACCAGAAGTTCGAGGACAAGGCCACATTAACTGTCGA
CAAGTCATCCAACACAGCCTACATGGACCTCCTCAGTCTGACATCTGAGGACTCT
GCAGTCTATTATTGTGCAAGAAGGGACTGGGACTACTTTGACTACTGGGGCCAAG
GCACCACTCTCACAGTCTCCTCAGCCAAAACAACAGCCCCATCGGTCTATCCACT
GGCCCCTGTGTGTGGAGATACAACTGGCTCCTCGGTGACTCTAGGATGCCTGGTC
AAGGGTTATTTCCCTGAGCCAGTGACCTTGACCTGGAACTCTGGATCCCTGTCCA
GTGGTGTGCACACC

Figure 69

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCTTACAA
TGGTGGTACTAACTACAACCAGAAGTTCGAGGACAAGGCCACATTAACTGTCGA
CAAGTCATCCAACACAGCCTACATGGACCTCCTCAGTCTGACATCTGAGGACTCT
GCAGTCTATTATTGTGCAAGAAGGGACTGGGACTACTTTGACTACTGGGGCCAAG
GCACCACTCTCACAGTCTCCTCAGCCAAAACAACAGCCCCATCGGTCTATCCACT
GGCCCCTGTGTGTGGAGATACAACTGGCTCCTCGGTGACTCTAGGATGCCTGGTC
AAGGGTTATTTCCCTGAGCCAGTGACCTTGACCTGGAACTCTGGATCCCTGTCCA
GTGGTGTGCACACC

Figure 70

GACGTTGTGATGACCCAGTCTCAAAAATTCCTGTCCACATCAGCAGGAGACAGG
GTCAGCATCTCCTGCAAGGCCAGTCAGAATGTGGGTACTGCTTTAGCCTGGTATC
AACAGAAACCAGGACAATCTCCTAAACTTTTGATTTACTCGGCATCCAATCGGAA
CACTGGAGTCCCTGATCGCTTCACAGGCAGGGGATTTGGGACAGATTTCACTCTC
ACCATCAGCAATATGCAGTCTGAAGACCTGGCAGATTATTCTGCCAGCAATATA
GCAGCTATCCTTACACGTTCGGAGGGGGGACCAGGCTGGAAATAAAGCGGGCTG
ATGCTGCACCAACTGTATCCATCTTCCCACCATCCAGTGAGCAGTTAACATCTGG
AGGTGCCTCAGTCGTGTGCTTCTTGAACAACTTCTACCCCAAAGACATCAATGTC
AAGTGGAAGATTGATGGCAGTGAACGACAAAATGGCGTCCTGAACAGTTGGACT
GATCAGGACAGCAAAGACAGCACCTACAGCATGAGCAGCACCCTCACGTTGACC
AAGGACGAGTATGAACGACATAACAGCTATACCTGTGAGGCCACTCACAAGACA
TCAACTTCACCCATTGTCAAGAGCTTCAACAGGAATGAGACGCGTTGT

Figure 71

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCATACA
ATGGTGGTACTAGCTACAACCAGAAGTTCGAGGACAAGGCCACATTAACTGTTG
ACAAGTCATCCAACACAGCCTACATGGACCTCCTCAGTCTGACATCTGAGGACTC
TGCAGTCTATTATTGTGCAAGAAGGGACTGGGACTACTTTGACTACTGGGGCCAA
GGCACCACTCTCACAGTCTCCTCA

Figure 72

GAGGTCCAGCTGCAACAGTCTGGACCTGAGCTGGTGAAGCCTGGAGCTTCAATG
AAGATATCCTGCAAGGCTTCTGGTTACTCATTCACTGCCTACACCATGAACTGGG
TGAAGCAGACCCATGGAAAGAACCTTGAGTGGATTGGACTTATTAATCCTTACAA
TGGTGGTACTAACTACAACCAGAAGTTCGAGGACAAGGCCACATTAACTGTCGA
CAAGTCATCCAACACAGCCTACATGGACCTCCTCAGTCTGACATCTGAGGACTCT
GCAGTCTATTATTGTGCAAGAAGGGACTGGGACTACTTTGACTACTGGGGCCAAG
GCACCACTCTCACAGTCTCCTCA

Figure 73

GACGTTGTGATGACCCAGTCTCAAAAATTCCTGTCCACATCAGCAGGAGACAGG
GTCAGCATCTCCTGCAAGGCCAGTCAGAATGTGGGTACTGCTTTAGCCTGGTATC
AACAGAAACCAGGACAATCTCCTAAACTTTTGATTTACTCGGCATCCAATCGGAA
CACTGGAGTCCCTGATCGCTTCACAGGCAGGGGATTTGGGACAGATTTCACTCTC
ACCATCAGCAATATGCAGTCTGAAGACCTGGCAGATTATTTCTGCCAGCAATATA
GCAGCTATCCTTACACGTTCGGAGGGGGGACCAGGCTGGAAATA

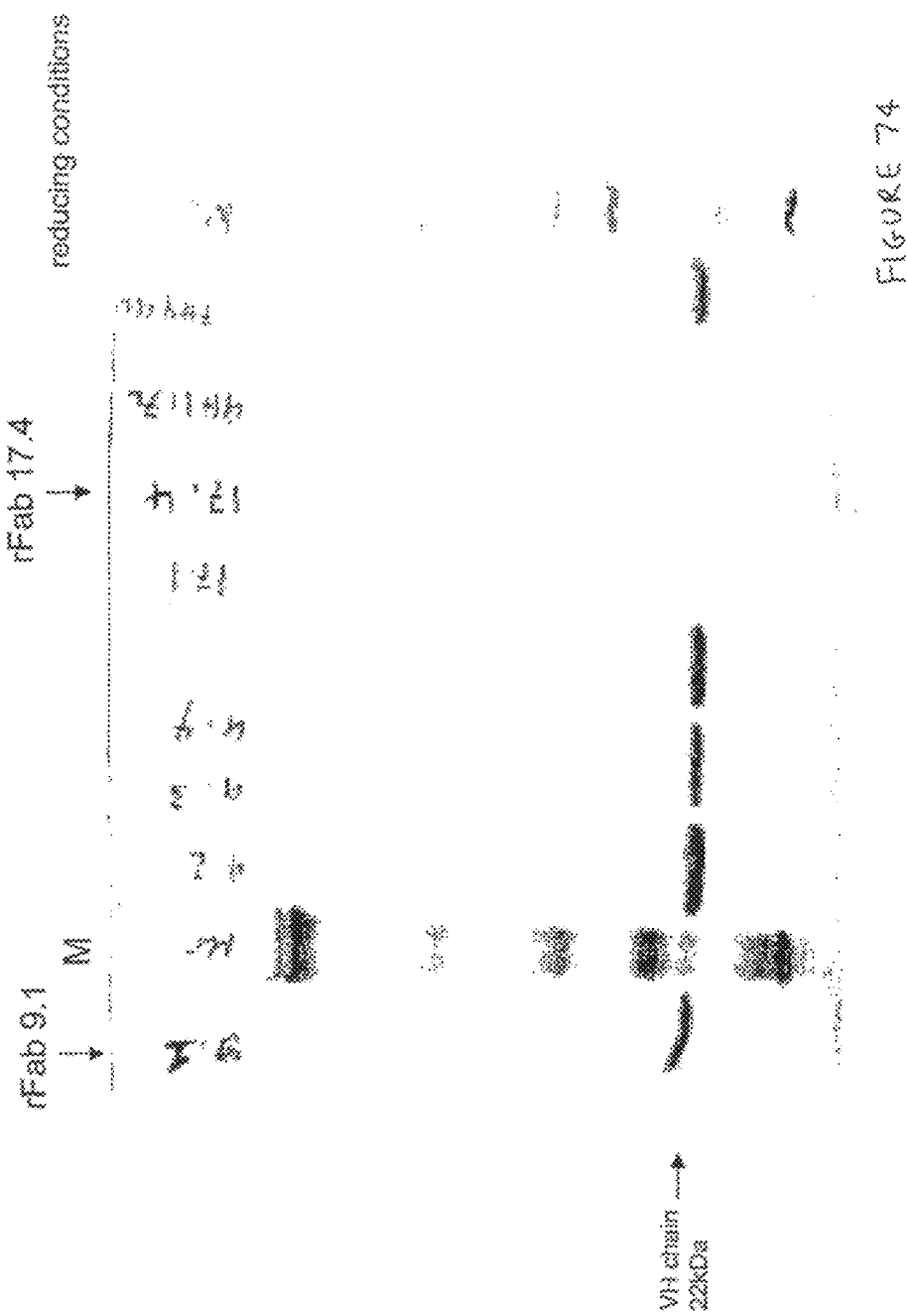

VH and VL sequence data of thyroid stimulating mAbs aligned with the mouse V-region gene family

```
V_H
    GAGATCCAGCTGCAGCAGTCTGGACCTGAGCTGGTGAAGCCTGGGGCTTCAGTGAAGGTATCCTGCAAGGCTTCTGGTTACTCATTCACTGACTACAACA  IGHV1S135
    ...G...........A......................................................T..C.....C..   mAb9Vh
    ...G...........A......................................................C.....C..    mAb17Vh

TGTACTGGGTGAAGCAGAGCCATGGAAAGAGCCTTGAGTGGATTGGATGGATTGATATATCCTACAATGGTGTACTACAACCAGAAGTTCAAGGGCAA  IGHV1S135
    .A..................A............CT....A......................A.......G......G....      mAb9Vh
    .A..........C.......A............CT....A......................A.......G....A....       mAb17Vh

GGCCACATTGACTGTTGACAAGTCCTCCAGCACAGCCTTCATGCATCTCAACAGCCTGACATCTGAGGACTCTGCAGTCTATTACTGTGCAAGA  IGHV1S135
    .....T.A......AA.......A.........................G.G...CT..T......C.............G..        mAb9Vh
    .........A.......C............A.....G.C...CT..T.............T..........                    mAb17Vh

---ACTGGGAC                                                                          IGHDQ52
    CTACTTTGACTACTGGGGCCAAGGCACCACTCTCACAGTCTCCTCA                                        IGHJ2
    AGGG ............................................                                    mAb9Vh
    ............................................                                          mAb17Vh

V_L
    AGACATTGTGATGACCCAGTCTCAAAAATTCATGTCCACATCAGTAGGAGACAGGGTCAGCATCACCTGCAAGGCCAGTCAGAATG......  IGKV6-17
    ...................G............................TT.....                                    mAb9Vk
    ........G....................C..........................T.....                             mAb17Vk

GCCTGGTATCAACAGAAACCAGGACAAATCTCCTAAACTACTGATTTACTCGGCATCCAATCGGTACACTGGAGTCCCTGATCGCTT......   IGKV6-15
    ..........................G....................TT.........                                   mAb9Vk
    ..................................A....................G.....                               mAb17Vk

CTGGGACAGATTTCACTCTCACCATCAGCAGTCTGGAGCCTGAAGACCTGGCAGTCTATTATTCTGCCAGCAATATAGCAGCTATCCT         IGKV6-15
    .......................A.............................................G.......              mAb9Vk
    .T..........................................................................             mAb17Vk

TACACGTTCGGAGGGGGGACCAAGCTGGAAATAAAAC                                                       IGKJ5
    .....................................                                                      mAb9Vk
    ..............G......................                                                      mAb17Vk
```

KSAb1 IgG2b = mAb9
KSAb2 IgG2a = mAb17

FIGURE 79

SEQUENCE LISTING

```
<160> NUMBER OF SEQ ID NOS: 66

<210> SEQ ID NO 1
<211> LENGTH: 5
<212> TYPE: PRT
<213> ORGANISM: Homo sapiens

<400> SEQUENCE: 1

Ala Tyr Thr Met Asn
1               5

<210> SEQ ID NO 2
<211> LENGTH: 5
<212> TYPE: PRT
<213> ORGANISM: Homo sapiens

<400> SEQUENCE: 2

Ala Tyr Thr Met Asp
1               5

<210> SEQ ID NO 3
<211> LENGTH: 17
<212> TYPE: PRT
<213> ORGANISM: Homo sapiens

<400> SEQUENCE: 3

Leu Ile Asn Pro Tyr Asn Gly Gly Thr Asn Tyr Asn Gln Glu Phe Glu
1               5                   10                  15

Gly

<210> SEQ ID NO 4
<211> LENGTH: 8
<212> TYPE: PRT
<213> ORGANISM: Homo sapiens
```

-continued

```
<400> SEQUENCE: 4

Arg Asp Trp Asp Tyr Phe Asp Tyr
1               5

<210> SEQ ID NO 5
<211> LENGTH: 11
<212> TYPE: PRT
<213> ORGANISM: Homo sapiens

<400> SEQUENCE: 5

Lys Ala Ser Gln Asn Val Gly Thr Phe Val Ala
1               5                  10

<210> SEQ ID NO 6
<211> LENGTH: 7
<212> TYPE: PRT
<213> ORGANISM: Homo sapiens

<400> SEQUENCE: 6

Ser Ala Ser Asn Arg Tyr Thr
1               5

<210> SEQ ID NO 7
<211> LENGTH: 9
<212> TYPE: PRT
<213> ORGANISM: Homo sapiens

<400> SEQUENCE: 7

Arg Gln Tyr Ser Ser Tyr Pro Tyr Thr
1               5

<210> SEQ ID NO 8
<211> LENGTH: 218
<212> TYPE: PRT
<213> ORGANISM: Homo sapiens

<400> SEQUENCE: 8

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser Ala Lys Thr Thr Thr Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
```

```
                180                 185                 190
Pro Ser Gln Thr Val Thr Cys Ser Val Ala His Pro Ala Ser Ser Thr
            195                 200                 205

Lys Val Asp Lys Lys Ile Glu Thr Arg Cys
    210                 215

<210> SEQ ID NO 9
<211> LENGTH: 218
<212> TYPE: PRT
<213> ORGANISM: Homo sapiens

<400> SEQUENCE: 9

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Phe Ala Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Lys Val Asp Lys Lys Ile Glu Thr Arg Cys
    210                 215

<210> SEQ ID NO 10
<211> LENGTH: 226
<212> TYPE: PRT
<213> ORGANISM: Homo sapiens

<400> SEQUENCE: 10

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
            20                  25                  30

Thr Met Asp Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80
```

```
Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
                100                 105                 110

Leu Thr Val Ser Ser Ala Lys Thr Thr Pro Pro Ser Val Tyr Pro Leu
                115                 120                 125

Ala Pro Gly Cys Gly Asp Thr Thr Gly Ser Ser Val Thr Leu Gly Cys
            130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Val Thr Val Pro Ser Ser Thr Trp
                180                 185                 190

Pro Ser Gln Thr Val Thr Cys Ser Val Ala His Pro Ala Ser Ser Thr
                195                 200                 205

Lys Val Asp Arg Lys Leu Arg Arg Val Val Lys Gly Glu Phe Cys Arg
210                 215                 220

Tyr Pro
225

<210> SEQ ID NO 11
<211> LENGTH: 218
<212> TYPE: PRT
<213> ORGANISM: Homo sapiens

<400> SEQUENCE: 11

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Gly Ser Ala Val Tyr Tyr Cys
                85                  90                  95

Ala Arg Arg Asp Trp Asp Tyr Phe Asp Tyr Trp Gly Gln Gly Thr Thr
                100                 105                 110

Leu Thr Val Ser Ser Ala Lys Thr Thr Pro Pro Ser Val Tyr Pro Leu
                115                 120                 125

Ala Pro Gly Cys Gly Asp Thr Thr Gly Ser Ser Val Thr Leu Gly Cys
            130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Val Thr Val Pro Ser Ser Thr Trp
                180                 185                 190

Pro Ser Gln Thr Val Thr Cys Ser Val Ala His Pro Ala Ser Ser Thr
                195                 200                 205

Lys Val Asp Lys Lys Ile Glu Thr Arg Cys
210                 215
```

```
<210> SEQ ID NO 12
<211> LENGTH: 216
<212> TYPE: PRT
<213> ORGANISM: Homo sapiens

<400> SEQUENCE: 12

Asp Ile Val Met Thr Gln Ser Gln Lys Phe Met Ser Thr Ser Val Gly
1               5                   10                  15

Asp Arg Val Ser Ile Ile Cys Lys Ala Ser Gln Asn Val Gly Thr Phe
            20                  25                  30

Val Ala Trp Tyr Gln Gln Lys Pro Gly Gln Ser Pro Lys Leu Leu Val
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Arg Gln Tyr Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Val Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Thr Arg Cys
    210                 215

<210> SEQ ID NO 13
<211> LENGTH: 117
<212> TYPE: PRT
<213> ORGANISM: Homo sapiens

<400> SEQUENCE: 13

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110
```

```
Leu Thr Val Ser Ser
        115

<210> SEQ ID NO 14
<211> LENGTH: 117
<212> TYPE: PRT
<213> ORGANISM: Homo sapiens

<400> SEQUENCE: 14

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Phe Ala Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser
        115

<210> SEQ ID NO 15
<211> LENGTH: 117
<212> TYPE: PRT
<213> ORGANISM: Homo sapiens

<400> SEQUENCE: 15

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
            20                  25                  30

Thr Met Asp Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
    50                  55                  60

Glu Gly Lys Ala Thr Leu Thr Val Asn Lys Ser Ser Asn Thr Ala Phe
65                  70                  75                  80

Met Glu Leu Leu Ser Leu Thr Ser Asp Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser
        115

<210> SEQ ID NO 16
<211> LENGTH: 117
<212> TYPE: PRT
<213> ORGANISM: Homo sapiens

<400> SEQUENCE: 16

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Ser Ala Tyr
            20                  25                  30
```

```
Thr Met Asn Trp Val Lys Gln Ser His Gly Lys Asn Leu Glu Trp Ile
        35                  40                  45

Gly Leu Ile Asn Pro Tyr Asn Gly Gly Thr Asn Tyr Asn Gln Glu Phe
     50                  55                  60

Glu Gly Lys Ala Thr Leu Thr Val Asn Lys Ser Asn Thr Ala Phe
 65                  70                  75                  80

Met Glu Leu Leu Ser Leu Thr Ser Asp Gly Ser Ala Val Tyr Tyr Cys
                 85                  90                  95

Ala Arg Arg Asp Trp Asp Tyr Phe Asp Tyr Trp Gly Gln Gly Thr Thr
                100                 105                 110

Leu Thr Val Ser Ser
            115

<210> SEQ ID NO 17
<211> LENGTH: 106
<212> TYPE: PRT
<213> ORGANISM: Homo sapiens

<400> SEQUENCE: 17

Asp Ile Val Met Thr Gln Ser Gln Lys Phe Met Ser Thr Ser Val Gly
 1               5                  10                  15

Asp Arg Val Ser Ile Ile Cys Lys Ala Ser Gln Asn Val Gly Thr Phe
             20                  25                  30

Val Ala Trp Tyr Gln Gln Lys Pro Gly Gln Ser Pro Lys Leu Leu Val
         35                  40                  45

Tyr Ser Ala Ser Asn Arg Tyr Thr Gly Val Pro Asp Arg Phe Thr Gly
     50                  55                  60

Ser Gly Ser Gly Thr Asp Phe Thr Leu Thr Ile Asn Asn Met Gln Ser
 65                  70                  75                  80

Glu Asp Leu Ala Asp Tyr Phe Cys Arg Gln Tyr Ser Ser Tyr Pro Tyr
                 85                  90                  95

Thr Phe Gly Gly Gly Thr Lys Leu Glu Ile
                100                 105

<210> SEQ ID NO 18
<211> LENGTH: 238
<212> TYPE: PRT
<213> ORGANISM: Homo sapiens

<400> SEQUENCE: 18

Asp Ile Val Met Thr Gln Ser Gln Lys Phe Met Ser Thr Ser Val Gly
 1               5                  10                  15

Asp Arg Val Ser Ile Ile Cys Lys Ala Ser Gln Asn Val Gly Thr Phe
             20                  25                  30

Val Ala Trp Tyr Gln Gln Lys Pro Gly Gln Ser Pro Lys Leu Leu Val
         35                  40                  45

Tyr Ser Ala Ser Asn Arg Tyr Thr Gly Val Pro Asp Arg Phe Thr Gly
     50                  55                  60

Ser Gly Ser Gly Thr Asp Phe Thr Leu Thr Ile Asn Asn Met Gln Ser
 65                  70                  75                  80

Glu Asp Leu Ala Asp Tyr Phe Cys Arg Gln Tyr Ser Ser Tyr Pro Tyr
                 85                  90                  95

Thr Phe Gly Gly Gly Thr Lys Leu Glu Ile Gly Gly Gly Ser Gly
                100                 105                 110

Gly Gly Gly Ser Gly Gly Gly Ser Glu Val Gln Leu Gln Gln Ser
        115                 120                 125
```

```
Gly Pro Glu Leu Val Lys Pro Gly Ala Ser Met Lys Ile Ser Cys Lys
            130                 135                 140
Ala Ser Gly Tyr Ser Phe Ser Ala Tyr Thr Met Asn Trp Val Lys Gln
145                 150                 155                 160
Ser His Gly Lys Asn Leu Glu Trp Ile Gly Leu Ile Asn Pro Tyr Asn
                165                 170                 175
Gly Gly Thr Asn Tyr Asn Gln Glu Phe Glu Gly Lys Ala Thr Leu Thr
            180                 185                 190
Val Asn Lys Ser Ser Asn Thr Ala Phe Met Glu Leu Leu Ser Leu Thr
                195                 200                 205
Ser Asp Asp Ser Ala Val Tyr Tyr Cys Ala Arg Arg Asp Trp Asp Tyr
            210                 215                 220
Phe Asp Tyr Trp Gly Gln Gly Thr Thr Leu Thr Val Ser Ser
225                 230                 235

<210> SEQ ID NO 19
<211> LENGTH: 238
<212> TYPE: PRT
<213> ORGANISM: Homo sapiens

<400> SEQUENCE: 19

Asp Ile Val Met Thr Gln Ser Gln Lys Phe Met Ser Thr Ser Val Gly
1               5                   10                  15
Asp Arg Val Ser Ile Ile Cys Lys Ala Ser Gln Asn Val Gly Thr Phe
                20                  25                  30
Val Ala Trp Tyr Gln Gln Lys Pro Gly Gln Ser Pro Lys Leu Leu Val
            35                  40                  45
Tyr Ser Ala Ser Asn Arg Tyr Thr Gly Val Pro Asp Arg Phe Thr Gly
50                  55                  60
Ser Gly Ser Gly Thr Asp Phe Thr Leu Thr Ile Asn Asn Met Gln Ser
65                  70                  75                  80
Glu Asp Leu Ala Asp Tyr Phe Cys Arg Gln Tyr Ser Ser Tyr Pro Tyr
                85                  90                  95
Thr Phe Gly Gly Gly Thr Lys Leu Glu Ile Gly Gly Gly Ser Gly
                100                 105                 110
Gly Gly Gly Ser Gly Gly Gly Ser Glu Val Gln Leu Gln Gln Ser
            115                 120                 125
Gly Pro Glu Leu Val Lys Pro Gly Ala Ser Met Lys Ile Ser Cys Lys
            130                 135                 140
Ala Ser Gly Tyr Ser Phe Phe Ala Tyr Thr Met Asn Trp Val Lys Gln
145                 150                 155                 160
Ser His Gly Lys Asn Leu Glu Trp Ile Gly Leu Ile Asn Pro Tyr Asn
                165                 170                 175
Gly Gly Thr Asn Tyr Asn Gln Glu Phe Glu Gly Lys Ala Thr Leu Thr
            180                 185                 190
Val Asn Lys Ser Ser Asn Thr Ala Phe Met Glu Leu Leu Ser Leu Thr
                195                 200                 205
Ser Asp Asp Ser Ala Val Tyr Tyr Cys Ala Arg Arg Asp Trp Asp Tyr
            210                 215                 220
Phe Asp Tyr Trp Gly Gln Gly Thr Thr Leu Thr Val Ser Ser
225                 230                 235

<210> SEQ ID NO 20
<211> LENGTH: 238
<212> TYPE: PRT
<213> ORGANISM: Homo sapiens
```

US 8,603,466 B2
51                                                                    52
-continued

<400> SEQUENCE: 20

Asp Ile Val Met Thr Gln Ser Gln Lys Phe Met Ser Thr Ser Val Gly
1               5                   10                  15

Asp Arg Val Ser Ile Ile Cys Lys Ala Ser Gln Asn Val Gly Thr Phe
            20                  25                  30

Val Ala Trp Tyr Gln Gln Lys Pro Gly Gln Ser Pro Lys Leu Leu Val
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Arg Gln Tyr Ser Ser Tyr Pro Tyr
                85                  90                  95

Thr Phe Gly Gly Gly Thr Lys Leu Glu Ile Gly Gly Gly Ser Gly
            100                 105                 110

Gly Gly Gly Ser Gly Gly Gly Ser Glu Val Gln Leu Gln Gln Ser
        115                 120                 125

Gly Pro Glu Leu Val Lys Pro Gly Ala Ser Met Lys Ile Ser Cys Lys
130                 135                 140

Ala Ser Gly Tyr Ser Phe Ser Ala Tyr Thr Met Asp Trp Val Lys Gln
145                 150                 155                 160

Ser His Gly Lys Asn Leu Glu Trp Ile Gly Leu Ile Asn Pro Tyr Asn
                165                 170                 175

Gly Gly Thr Asn Tyr Asn Gln Glu Phe Glu Gly Lys Ala Thr Leu Thr
            180                 185                 190

Val Asn Lys Ser Ser Asn Thr Ala Phe Met Glu Leu Leu Ser Leu Thr
        195                 200                 205

Ser Asp Asp Ser Ala Val Tyr Tyr Cys Ala Arg Arg Asp Trp Asp Tyr
    210                 215                 220

Phe Asp Tyr Trp Gly Gln Gly Thr Thr Leu Thr Val Ser Ser
225                 230                 235

<210> SEQ ID NO 21
<211> LENGTH: 238
<212> TYPE: PRT
<213> ORGANISM: Homo sapiens

<400> SEQUENCE: 21

Asp Ile Val Met Thr Gln Ser Gln Lys Phe Met Ser Thr Ser Val Gly
1               5                   10                  15

Asp Arg Val Ser Ile Ile Cys Lys Ala Ser Gln Asn Val Gly Thr Phe
            20                  25                  30

Val Ala Trp Tyr Gln Gln Lys Pro Gly Gln Ser Pro Lys Leu Leu Val
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Arg Gln Tyr Ser Ser Tyr Pro Tyr
                85                  90                  95

Thr Phe Gly Gly Gly Thr Lys Leu Glu Ile Gly Gly Gly Ser Gly
            100                 105                 110

Gly Gly Gly Ser Gly Gly Gly Ser Glu Val Gln Leu Gln Gln Ser
        115                 120                 125

Gly Pro Glu Leu Val Lys Pro Gly Ala Ser Met Lys Ile Ser Cys Lys

```
                    130                 135                 140
Ala Ser Gly Tyr Ser Phe Ser Ala Tyr Thr Met Asn Trp Val Lys Gln
145                 150                 155                 160

Ser His Gly Lys Asn Leu Glu Trp Ile Gly Leu Ile Asn Pro Tyr Asn
                165                 170                 175

Gly Gly Thr Asn Tyr Asn Gln Glu Phe Glu Gly Lys Ala Thr Leu Thr
            180                 185                 190

Val Asn Lys Ser Ser Asn Thr Ala Phe Met Glu Leu Leu Ser Leu Thr
        195                 200                 205

Ser Asp Gly Ser Ala Val Tyr Tyr Cys Ala Arg Arg Asp Trp Asp Tyr
    210                 215                 220

Phe Asp Tyr Trp Gly Gln Gly Thr Thr Leu Thr Val Ser Ser
225                 230                 235

<210> SEQ ID NO 22
<211> LENGTH: 15
<212> TYPE: PRT
<213> ORGANISM: Homo sapiens

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 17
<212> TYPE: PRT
<213> ORGANISM: Homo sapiens

<400> SEQUENCE: 23

Leu Ile Asn Pro Tyr Asn Gly Gly Thr Ser Tyr Asn Gln Lys Phe Glu
1               5                   10                  15

Asp

<210> SEQ ID NO 24
<211> LENGTH: 17
<212> TYPE: PRT
<213> ORGANISM: Homo sapiens

<400> SEQUENCE: 24

Leu Ile Asn Pro Tyr Asn Gly Gly Thr Asn Tyr Asn Gln Lys Phe Glu
1               5                   10                  15

Asp

<210> SEQ ID NO 25
<211> LENGTH: 11
<212> TYPE: PRT
<213> ORGANISM: Homo sapiens

<400> SEQUENCE: 25

Lys Ala Ser Gln Asn Val Gly Thr Ala Leu Ala
1               5                   10

<210> SEQ ID NO 26
<211> LENGTH: 7
<212> TYPE: PRT
<213> ORGANISM: Homo sapiens

<400> SEQUENCE: 26

Ser Ala Ser Asn Arg Asn Thr
1               5
```

```
<210> SEQ ID NO 27
<211> LENGTH: 9
<212> TYPE: PRT
<213> ORGANISM: Homo sapiens

<400> SEQUENCE: 27

Gln Gln Tyr Ser Ser Tyr Pro Tyr Thr
1               5

<210> SEQ ID NO 28
<211> LENGTH: 218
<212> TYPE: PRT
<213> ORGANISM: Homo sapiens

<400> SEQUENCE: 28

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
            20                  25                  30

Thr Met Asn Trp Val Lys Gln Thr His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Glu Asp Lys Ala Thr Leu Thr Val Asp Lys Ser Ser Asn Thr Ala Tyr
65                  70                  75                  80

Met Asp Leu Leu Ser Leu Thr Ser Glu Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser Ala Lys Thr Thr Ala Pro Ala Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Thr Arg Cys
    210                 215

<210> SEQ ID NO 29
<211> LENGTH: 218
<212> TYPE: PRT
<213> ORGANISM: Homo sapiens

<400> SEQUENCE: 29

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
            20                  25                  30

Thr Met Asn Trp Val Lys Gln Thr His Gly Lys Asn Leu Glu Trp Ile
        35                  40                  45

Gly Leu Ile Asn Pro Tyr Asn Gly Gly Thr Asn Tyr Asn Gln Lys Phe
    50                  55                  60
```

Glu Asp Lys Ala Thr Leu Thr Val Asp Lys Ser Ser Asn Thr Ala Tyr
65                  70                  75                  80

Met Asp Leu Leu Ser Leu Thr Ser Glu Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Thr Arg Cys
    210                 215

<210> SEQ ID NO 30
<211> LENGTH: 169
<212> TYPE: PRT
<213> ORGANISM: Homo sapiens

<400> SEQUENCE: 30

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
                20                  25                  30

Thr Met Asn Trp Val Lys Gln Thr His Gly Lys Asn Leu Glu Trp Ile
            35                  40                  45

Gly Leu Ile Asn Pro Tyr Asn Gly Gly Thr Asn Tyr Asn Gln Lys Phe
        50                  55                  60

Glu Asp Lys Ala Thr Leu Thr Val Asp Lys Ser Ser Asn Thr Ala Tyr
65                  70                  75                  80

Met Asp Leu Leu Ser Leu Thr Ser Glu Asp Ser Ala Val Tyr Tyr Cys
                85                  90                  95

Ala Arg Arg Asp Trp Asp Tyr Phe Asp Tyr Trp Gly Gln Gly Thr Thr
            100                 105                 110

Leu Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr
                165

<210> SEQ ID NO 31
<211> LENGTH: 216
<212> TYPE: PRT
<213> ORGANISM: Homo sapiens

<400> SEQUENCE: 31

Asp Val Val Met Thr Gln Ser Gln Lys Phe Leu Ser Thr Ser Ala Gly

```
             1               5                  10                 15
Asp Arg Val Ser Ile Ser Cys Lys Ala Ser Gln Asn Val Gly Thr Ala
                20                  25                 30

Leu Ala Trp Tyr Gln Gln Lys Pro Gly Gln Ser Pro Lys Leu Leu Ile
            35                  40                 45

Tyr Ser Ala Ser Asn Arg Asn Thr Gly Val Pro Asp Arg Phe Thr Gly
        50                  55                 60

Arg Gly Phe Gly Thr Asp Phe Thr Leu Thr Ile Ser Asn Met Gln Ser
65                  70                 75                  80

Glu Asp Leu Ala Asp Tyr Phe Cys Gln Gln Tyr Ser Ser Tyr Pro Tyr
                85                 90                  95

Thr Phe Gly Gly Gly Thr Arg Leu Glu Ile Lys Arg Ala Asp Ala Ala
                100                105                110

Pro Thr Val Ser Ile Phe Pro Pro Ser Ser Glu Gln Leu Thr Ser Gly
            115                 120                125

Gly Ala Ser Val Val Cys Phe Leu Asn Asn Phe Tyr Pro Lys Asp Ile
        130                 135                140

Asn Val Lys Trp Lys Ile Asp Gly Ser Glu Arg Gln Asn Gly Val Leu
145                 150                 155                160

Asn Ser Trp Thr Asp Gln Asp Ser Lys Asp Ser Thr Tyr Ser Met Ser
                165                170                 175

Ser Thr Leu Thr Leu Thr Lys Asp Glu Tyr Glu Arg His Asn Ser Tyr
            180                 185                190

Thr Cys Glu Ala Thr His Lys Thr Ser Thr Ser Pro Ile Val Lys Ser
        195                 200                205

Phe Asn Arg Asn Glu Thr Arg Cys
    210                 215

<210> SEQ ID NO 32
<211> LENGTH: 117
<212> TYPE: PRT
<213> ORGANISM: Homo sapiens

<400> SEQUENCE: 32

Glu Val Gln Leu Gln Gln Ser Gly Pro Glu Leu Val Lys Pro Gly Ala
1               5                  10                 15

Ser Met Lys Ile Ser Cys Lys Ala Ser Gly Tyr Ser Phe Thr Ala Tyr
                20                 25                  30

Thr Met Asn Trp Val Lys Gln Thr His Gly Lys Asn Leu Glu Trp Ile
            35                  40                 45

Gly Leu Ile Asn Pro Tyr Asn Gly Gly Thr Ser Tyr Asn Gln Lys Phe
        50                  55                 60

Glu Asp Lys Ala Thr Leu Thr Val Asp Lys Ser Ser Asn Thr Ala Tyr
65                  70                 75                  80

Met Asp Leu Leu Ser Leu Thr Ser Glu Asp Ser Ala Val Tyr Tyr Cys
                85                 90                  95

Ala Arg Arg Asp Trp Asp Tyr Phe Asp Tyr Trp Gly Gln Gly Thr Thr
                100                105                110

Leu Thr Val Ser Ser
    115

<210> SEQ ID NO 33
<211> LENGTH: 117
<212> TYPE: PRT
<213> ORGANISM: Homo sapiens

<400> SEQUENCE: 33
```

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
            20                  25                  30

Thr Met Asn Trp Val Lys Gln Thr His Gly Lys Asn Leu Glu Trp Ile
        35                  40                  45

Gly Leu Ile Asn Pro Tyr Asn Gly Gly Thr Asn Tyr Asn Gln Lys Phe
    50                  55                  60

Glu Asp Lys Ala Thr Leu Thr Val Asp Lys Ser Ser Asn Thr Ala Tyr
65                  70                  75                  80

Met Asp Leu Leu Ser Leu Thr Ser Glu Asp Ser Ala Val Tyr Tyr Cys
                85                  90                  95

Ala Arg Arg Asp Trp Asp Tyr Phe Asp Tyr Trp Gly Gln Gly Thr Thr
                100                 105                 110

Leu Thr Val Ser Ser
        115

<210> SEQ ID NO 34
<211> LENGTH: 106
<212> TYPE: PRT
<213> ORGANISM: Homo sapiens

<400> SEQUENCE: 34

Asp Val Val Met Thr Gln Ser Gln Lys Phe Leu Ser Thr Ser Ala Gly
1               5                   10                  15

Asp Arg Val Ser Ile Ser Cys Lys Ala Ser Gln Asn Val Gly Thr Ala
            20                  25                  30

Leu Ala Trp Tyr Gln Gln Lys Pro Gly Gln Ser Pro Lys Leu Leu Ile
        35                  40                  45

Tyr Ser Ala Ser Asn Arg Asn Thr Gly Val Pro Asp Arg Phe Thr Gly
    50                  55                  60

Arg Gly Phe Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Arg Leu Glu Ile
                100                 105

<210> SEQ ID NO 35
<211> LENGTH: 238
<212> TYPE: PRT
<213> ORGANISM: Homo sapiens

<400> SEQUENCE: 35

Asp Val Val Met Thr Gln Ser Gln Lys Phe Leu Ser Thr Ser Ala Gly
1               5                   10                  15

Asp Arg Val Ser Ile Ser Cys Lys Ala Ser Gln Asn Val Gly Thr Ala
            20                  25                  30

Leu Ala Trp Tyr Gln Gln Lys Pro Gly Gln Ser Pro Lys Leu Leu Ile
        35                  40                  45

Tyr Ser Ala Ser Asn Arg Asn Thr Gly Val Pro Asp Arg Phe Thr Gly
    50                  55                  60

Arg Gly Phe Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Tyr
                85                  90                  95

```
Thr Phe Gly Gly Gly Thr Arg Leu Glu Ile Gly Gly Gly Ser Gly
                100                 105                 110

Gly Gly Gly Ser Gly Gly Gly Ser Glu Val Gln Leu Gln Gln Ser
            115                 120                 125

Gly Pro Glu Leu Val Lys Pro Gly Ala Ser Met Lys Ile Ser Cys Lys
130                 135                 140

Ala Ser Gly Tyr Ser Phe Thr Ala Tyr Thr Met Asn Trp Val Lys Gln
145                 150                 155                 160

Thr His Gly Lys Asn Leu Glu Trp Ile Gly Leu Ile Asn Pro Tyr Asn
                165                 170                 175

Gly Gly Thr Ser Tyr Asn Gln Lys Phe Glu Asp Lys Ala Thr Leu Thr
            180                 185                 190

Val Asp Lys Ser Ser Asn Thr Ala Tyr Met Asp Leu Leu Ser Leu Thr
        195                 200                 205

Ser Glu Asp Ser Ala Val Tyr Tyr Cys Ala Arg Arg Asp Trp Asp Tyr
    210                 215                 220

Phe Asp Tyr Trp Gly Gln Gly Thr Thr Leu Thr Val Ser Ser
225                 230                 235
```

<210> SEQ ID NO 36
<211> LENGTH: 238
<212> TYPE: PRT
<213> ORGANISM: Homo sapiens
<400> SEQUENCE: 36

```
Asp Val Val Met Thr Gln Ser Gln Lys Phe Leu Ser Thr Ser Ala Gly
1               5                   10                  15

Asp Arg Val Ser Ile Ser Cys Lys Ala Ser Gln Asn Val Gly Thr Ala
                20                  25                  30

Leu Ala Trp Tyr Gln Gln Lys Pro Gly Gln Ser Pro Lys Leu Leu Ile
            35                  40                  45

Tyr Ser Ala Ser Asn Arg Asn Thr Gly Val Pro Asp Arg Phe Thr Gly
        50                  55                  60

Arg Gly Phe Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Arg Leu Glu Ile Gly Gly Gly Gly Ser Gly
                100                 105                 110

Gly Gly Gly Ser Gly Gly Gly Ser Glu Val Gln Leu Gln Gln Ser
            115                 120                 125

Gly Pro Glu Leu Val Lys Pro Gly Ala Ser Met Lys Ile Ser Cys Lys
130                 135                 140

Ala Ser Gly Tyr Ser Phe Thr Ala Tyr Thr Met Asn Trp Val Lys Gln
145                 150                 155                 160

Thr His Gly Lys Asn Leu Glu Trp Ile Gly Leu Ile Asn Pro Tyr Asn
                165                 170                 175

Gly Gly Thr Asn Tyr Asn Gln Lys Phe Glu Asp Lys Ala Thr Leu Thr
            180                 185                 190

Val Asp Lys Ser Ser Asn Thr Ala Tyr Met Asp Leu Leu Ser Leu Thr
        195                 200                 205

Ser Glu Asp Ser Ala Val Tyr Tyr Cys Ala Arg Arg Asp Trp Asp Tyr
    210                 215                 220

Phe Asp Tyr Trp Gly Gln Gly Thr Thr Leu Thr Val Ser Ser
225                 230                 235
```

```
<210> SEQ ID NO 37
<211> LENGTH: 15
<212> TYPE: DNA
<213> ORGANISM: Homo sapiens

<400> SEQUENCE: 37
gcctacacca tgaac                                                          15

<210> SEQ ID NO 38
<211> LENGTH: 15
<212> TYPE: DNA
<213> ORGANISM: Homo sapiens

<400> SEQUENCE: 38
gcctacacca tggac                                                          15

<210> SEQ ID NO 39
<211> LENGTH: 51
<212> TYPE: DNA
<213> ORGANISM: Homo sapiens

<400> SEQUENCE: 39
cttattaatc cttacaatgg tggtactaac tacaaccagg agttcgaggg c                  51

<210> SEQ ID NO 40
<211> LENGTH: 24
<212> TYPE: DNA
<213> ORGANISM: Homo sapiens

<400> SEQUENCE: 40
agggactggg actactttga ctac                                                24

<210> SEQ ID NO 41
<211> LENGTH: 33
<212> TYPE: DNA
<213> ORGANISM: Homo sapiens

<400> SEQUENCE: 41
aaggccagtc agaatgtggg tactttttgta gcc                                     33

<210> SEQ ID NO 42
<211> LENGTH: 21
<212> TYPE: DNA
<213> ORGANISM: Homo sapiens

<400> SEQUENCE: 42
tcggcatcca atcggtacac t                                                   21

<210> SEQ ID NO 43
<211> LENGTH: 27
<212> TYPE: DNA
<213> ORGANISM: Homo sapiens

<400> SEQUENCE: 43
cggcaatata gcagctatcc gtacacg                                             27

<210> SEQ ID NO 44
<211> LENGTH: 654
<212> TYPE: DNA
<213> ORGANISM: Homo sapiens

<400> SEQUENCE: 44
gaggtccagc tgcaacagtc tggacctgag ctggtgaagc ctggagcttc aatgaagata         60
```

```
tcctgcaagg cttctggtta ctcattctct gcctacacca tgaactgggt gaagcagagc    120
catggaaaga accttgagtg gattggactt attaatcctt acaatggtgg tactaactac    180
aaccaggagt tcgagggcaa ggccacttta actgtaaaca agtcatccaa cacagccttc    240
atggagctcc tcagtctgac atctgacgac tctgcagtct attactgtgc gagaagggac    300
tgggactact ttgactactg gggccaaggc accactctca cagtctcctc agccaaaaca    360
acaaccccat cagtctatcc actggcccct gggtgtggag atacaactgg ttcctccgtg    420
actctgggat gcctggtcaa gggctacttc cctgagtcag tgactgtgac ttggaactct    480
ggatccctgt ccagcagtgt gcacaccttc ccagctctcc tgcagtctgg actctacact    540
atgagcagct cagtgactgt cccctccagc acctggccaa gtcagaccgt cacctgcagc    600
gttgctcacc cagccagcag caccaaggtg acaagaaaaa ttgagacgcg ttgt           654

<210> SEQ ID NO 45
<211> LENGTH: 654
<212> TYPE: DNA
<213> ORGANISM: Homo sapiens

<400> SEQUENCE: 45
gaggtccagc tgcaacagtc tggacctgag ctggtgaagc ctggagcttc aatgaagata     60
tcctgcaagg cttctggtta ctcattcttt gcctacacca tgaactgggt gaagcagagc    120
catggaaaga accttgagtg gattggactt attaatcctt acaatggtgg tactaactac    180
aaccaggagt tcgagggcaa ggccacttta actgtaaaca agtcatccaa cacagccttc    240
atggagctcc tcagtctgac atctgacgac tctgcagtct attactgtgc gagaagggac    300
tgggactact ttgactactg gggccaaggc accactctca cagtctcctc agccaaaaca    360 acaccccat cagtctatcc actggcccct gggtgtggag atacaactgg ttcctccgtg     420
actctgggat gcctggtcaa gggctacttc cctgagtcag tgactgtgac ttggaactct    480
ggatccctgt ccagcagtgt gcacaccttc ccagctctcc tgcagtctgg actctacact    540
atgagcagct cagtgactgt cccctccagc acctggccaa gtcagaccgt cacctgcagc    600
gttgctcacc cagccagcag caccaaggtg acaagaaaaa ttgagacgcg ttgt           654

<210> SEQ ID NO 46
<211> LENGTH: 679
<212> TYPE: DNA
<213> ORGANISM: Homo sapiens

<400> SEQUENCE: 46
gaggtccagc tgcaacagtc tggacctgag ctggtgaagc ctggagcttc aatgaagata     60
tcctgcaagg cttctggtta ctcattctct gcctacacca tggactgggt gaagcagagc    120
catggaaaga accttgagtg gattggactt attaatcctt acaatggtgg tactaactac    180
aaccaggagt tcgagggcaa ggccacttta actgtaaaca agtcatccaa cacagccttc    240
atggagctcc tcagtctgac atctgacgac tctgcagtct attactgtgc gagaagggac    300
tgggactact ttgactactg gggccaaggc accactctca cagtctcctc agccaaaaca    360 acaccccat cagtctatcc actggcccct gggtgtggag atacaactgg ttcctccgtg     420
actctgggat gcctggtcaa gggctacttc cctgagtcag tgactgtgac ttggaactct    480
ggatccctgt ccagcagtgt gcacaccttc ccagctctcc tgcagtctgg actctacact    540
atgagcagct cagtgactgt cccctccagc acctggccaa gtcagaccgt cacctgcagc    600
gttgctcacc cagccagcag caccaaggtg acagaaaat tgagacgcgt tgtcaagggc     660
```

```
gaattctgca gatatccat                                               679
```

<210> SEQ ID NO 47
<211> LENGTH: 654
<212> TYPE: DNA
<213> ORGANISM: Homo sapiens

<400> SEQUENCE: 47

```
gaggtccagc tgcaacagtc tggacctgag ctggtgaagc ctggagcttc aatgaagata    60
tcctgcaagg cttctggtta ctcattctct gcctacacca tgaactgggt gaagcagagc   120
catggaaaga accttgagtg gattggactt attaatcctt acaatggtgg tactaactac   180
aaccaggagt tcgagggcaa ggccacttta actgtaaaca agtcatccaa cacagccttc   240
atggagctcc tcagtctgac atctgacggc tctgcagtct attactgtgc gagaagggac   300
tgggactact ttgactactg gggccaaggc accactctca cagtctcctc agccaaaaca   360
acaccccat cagtctatcc actgcccct gggtgtggag atacaactgg ttcctccgtg     420
actctgggat gcctggtcaa gggctacttc cctgagtcag tgactgtgac ttggaactct   480
ggatccctgt ccagcagtgt gcacaccttc ccagctctcc tgcagtctgg actctacact   540
atgagcagct cagtgactgt cccctccagc acctggccaa gtcagaccgt cacctgcagc   600
gttgctcacc cagccagcag caccaaggtg acaagaaaa ttgagacgcg ttgt           654
```

<210> SEQ ID NO 48
<211> LENGTH: 648
<212> TYPE: DNA
<213> ORGANISM: Homo sapiens

<400> SEQUENCE: 48

```
gacattgtga tgacccagtc tcaaaaattc atgtccacat cagtaggaga cagggtcagc    60
atcatttgca aggccagtca gaatgtgggt acttttgtag cctggtatca acagaaacca   120
ggacaatctc ctaaaactact ggtttactcg gcatccaatc ggtacactgg agtccctgat   180
cgcttcacag gcagtggatc tgggacagat ttcactctca ccatcaacaa tatgcagtct   240
gaagacctgg cagattattt ctgccggcaa tatagcagct atccgtacac gttcggaggg   300
gggaccaagc tagaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gttggcagtg aacgacaaaa tggcgtcctg   480
aacagttgga ctgatcagga cagcaaagac agcacctaca gcatgagcag cacccctcacg   540
ttgaccaagg acgagtatga acgacataac agctatacct gtgaggccac tcacaagaca   600
tcaacttcac ccattgtcaa gagcttcaac aggaatgaga cgcgttgt                 648
```

<210> SEQ ID NO 49
<211> LENGTH: 351
<212> TYPE: DNA
<213> ORGANISM: Homo sapiens

<400> SEQUENCE: 49

```
gaggtccagc tgcaacagtc tggacctgag ctggtgaagc ctggagcttc aatgaagata    60
tcctgcaagg cttctggtta ctcattctct gcctacacca tgaactgggt gaagcagagc   120
catggaaaga accttgagtg gattggactt attaatcctt acaatggtgg tactaactac   180
aaccaggagt tcgagggcaa ggccacttta actgtaaaca agtcatccaa cacagccttc   240
atggagctcc tcagtctgac atctgacgac tctgcagtct attactgtgc gagaagggac   300
```

```
tgggactact ttgactactg gggccaaggc accactctca cagtctcctc a        351
```

<210> SEQ ID NO 50
<211> LENGTH: 351
<212> TYPE: DNA
<213> ORGANISM: Homo sapiens

<400> SEQUENCE: 50

```
gaggtccagc tgcaacagtc tggacctgag ctggtgaagc ctggagcttc aatgaagata    60
tcctgcaagg cttctggtta ctcattcttt gcctacacca tgaactgggt gaagcagagc   120
catggaaaga accttgagtg gattggactt attaatcctt acaatggtgg tactaactac   180
aaccaggagt tcgagggcaa ggccacttta actgtaaaca agtcatccaa cacagccttc   240
atggagctcc tcagtctgac atctgacgac tctgcagtct attactgtgc gagaagggac   300
tgggactact ttgactactg gggccaaggc accactctca cagtctcctc a            351
```

<210> SEQ ID NO 51
<211> LENGTH: 351
<212> TYPE: DNA
<213> ORGANISM: Homo sapiens

<400> SEQUENCE: 51

```
gaggtccagc tgcaacagtc tggacctgag ctggtgaagc ctggagcttc aatgaagata    60
tcctgcaagg cttctggtta ctcattctct gcctacacca tggactgggt gaagcagagc   120
catggaaaga accttgagtg gattggactt attaatcctt acaatggtgg tactaactac   180
aaccaggagt tcgagggcaa ggccacttta actgtaaaca agtcatccaa cacagccttc   240
atggagctcc tcagtctgac atctgacgac tctgcagtct attactgtgc gagaagggac   300
tgggactact ttgactactg gggccaaggc accactctca cagtctcctc a            351
```

<210> SEQ ID NO 52
<211> LENGTH: 351
<212> TYPE: DNA
<213> ORGANISM: Homo sapiens

<400> SEQUENCE: 52

```
gaggtccagc tgcaacagtc tggacctgag ctggtgaagc ctggagcttc aatgaagata    60
tcctgcaagg cttctggtta ctcattctct gcctacacca tgaactgggt gaagcagagc   120
catggaaaga accttgagtg gattggactt attaatcctt acaatggtgg tactaactac   180
aaccaggagt tcgagggcaa ggccacttta actgtaaaca agtcatccaa cacagccttc   240
atggagctcc tcagtctgac atctgacggc tctgcagtct attactgtgc gagaagggac   300
tgggactact ttgactactg gggccaaggc accactctca cagtctcctc a            351
```

<210> SEQ ID NO 53
<211> LENGTH: 318
<212> TYPE: DNA
<213> ORGANISM: Homo sapiens

<400> SEQUENCE: 53

```
gacattgtga tgacccagtc tcaaaaattc atgtccacat cagtaggaga cagggtcagc    60
atcatttgca aggccagtca gaatgtgggt acttttgtag cctggtatca acagaaacca   120
ggacaatctc ctaaaactact ggtttactcg gcatccaatc ggtacactgg agtccctgat   180
cgcttcacag gcagtggatc tgggacagat ttcactctca ccatcaacaa tatgcagtct   240
gaagacctgg cagattattt ctgccggcaa tatagcagct atccgtacac gttcggaggg   300
```

```
gggaccaagc tagaaata                                                  318

<210> SEQ ID NO 54
<211> LENGTH: 51
<212> TYPE: DNA
<213> ORGANISM: Homo sapiens

<400> SEQUENCE: 54
cttattaatc catacaatgg tggtactagc tacaaccaga agttcgagga c              51

<210> SEQ ID NO 55
<211> LENGTH: 51
<212> TYPE: DNA
<213> ORGANISM: Homo sapiens

<400> SEQUENCE: 55
cttattaatc cttacaatgg tggtactaac tacaaccaga agttcgagga c              51

<210> SEQ ID NO 56
<211> LENGTH: 33
<212> TYPE: DNA
<213> ORGANISM: Homo sapiens

<400> SEQUENCE: 56
aaggccagtc agaatgtggg tactgcttta gcc                                 33

<210> SEQ ID NO 57
<211> LENGTH: 21
<212> TYPE: DNA
<213> ORGANISM: Homo sapiens

<400> SEQUENCE: 57
tcggcatcca atcggaacac t                                              21

<210> SEQ ID NO 58
<211> LENGTH: 27
<212> TYPE: DNA
<213> ORGANISM: Homo sapiens

<400> SEQUENCE: 58
cagcaatata gcagctatcc ttacacg                                        27

<210> SEQ ID NO 59
<211> LENGTH: 654
<212> TYPE: DNA
<213> ORGANISM: Homo sapiens

<400> SEQUENCE: 59
gaggtccagc tgcaacagtc tggacctgag ctggtgaagc ctggagcttc aatgaagata     60
tcctgcaagg cttctggtta ctcattcact gcctacacca tgaactgggt gaagcagacc    120
catgaaaaga accttgagtg gattggactt attaatccat acaatggtgg tactagctac    180
aaccagaagt tcgaggacaa ggccacatta actgttgaca gtcatccaa cacagcctac     240 atggacctcc tcagtctgac atctgaggac tctgcagtct attattgtgc aagaagggac    300
tgggactact ttgactactg ggccaaggc accactctca cagtctcctc agccaaaaca     360
acagccccag cggtctatcc actggcccct gtgtgtggag atacgactgg ctcctcggtg    420
actctaggat gcctggtcaa gggttatttc cctgagccag tgaccttgac ctggaactct    480
ggatccctgt ccagtggtgt gcacaccttc ccagctgtcc tgcagtctga cctctacacc    540
ctcagcagct cagtgactgt aacctcgagc acctggccca gccagtccat cacctgcaat    600
```

```
gtggcccacc cggcaagcag caccaaggtg gacaagaaaa ttgagacgcg ttgt          654
```

<210> SEQ ID NO 60
<211> LENGTH: 654
<212> TYPE: DNA
<213> ORGANISM: Homo sapiens

<400> SEQUENCE: 60

```
gaggtccagc tgcaacagtc tggacctgag ctggtgaagc ctggagcttc aatgaagata    60
tcctgcaagg cttctggtta ctcattcact gcctacacca tgaactgggt gaagcagacc   120
catggaaaga accttgagtg gattggactt attaatcctt acaatggtgg tactaactac   180
aaccagaagt tcgaggacaa ggccacatta actgtcgaca agtcatccaa cacagcctac   240
atggacctcc tcagtctgac atctgaggac tctgcagtct attattgtgc aagaagggac   300
tgggactact ttgactactg gggccaaggc accactctca cagtctcctc agccaaaaca   360
acagccccat cggtctatcc actggcccct gtgtgtggag atacaactgg ctcctcggtg   420
actctaggat gcctggtcaa gggttatttc cctgagccag tgaccttgac ctggaactct   480
ggatccctgt ccagtggtgt gcacaccttc ccagctgtcc tgcagtctga cctctacacc   540
ctcagcagct cagtgactgt aacctcgagc acctggccca gccagtccat cacctgcaat   600
gtggcccacc cggcaagcag caccaaggtg gacaagaaaa ttgagacgcg ttgt          654
```

<210> SEQ ID NO 61
<211> LENGTH: 507
<212> TYPE: DNA
<213> ORGANISM: Homo sapiens

<400> SEQUENCE: 61

```
gaggtccagc tgcaacagtc tggacctgag ctggtgaagc ctggagcttc aatgaagata    60
tcctgcaagg cttctggtta ctcattcact gcctacacca tgaactgggt gaagcagacc   120
catggaaaga accttgagtg gattggactt attaatcctt acaatggtgg tactaactac   180
aaccagaagt tcgaggacaa ggccacatta actgtcgaca agtcatccaa cacagcctac   240
atggacctcc tcagtctgac atctgaggac tctgcagtct attattgtgc aagaagggac   300
tgggactact ttgactactg gggccaaggc accactctca cagtctcctc agccaaaaca   360
acagccccat cggtctatcc actggcccct gtgtgtggag atacaactgg ctcctcggtg   420
actctaggat gcctggtcaa gggttatttc cctgagccag tgaccttgac ctggaactct   480
ggatccctgt ccagtggtgt gcacacc                                       507
```

<210> SEQ ID NO 62
<211> LENGTH: 507
<212> TYPE: DNA
<213> ORGANISM: Homo sapiens

<400> SEQUENCE: 62

```
gaggtccagc tgcaacagtc tggacctgag ctggtgaagc ctggagcttc aatgaagata    60
tcctgcaagg cttctggtta ctcattcact gcctacacca tgaactgggt gaagcagacc   120
catggaaaga accttgagtg gattggactt attaatcctt acaatggtgg tactaactac   180
aaccagaagt tcgaggacaa ggccacatta actgtcgaca agtcatccaa cacagcctac   240
atggacctcc tcagtctgac atctgaggac tctgcagtct attattgtgc aagaagggac   300
tgggactact ttgactactg gggccaaggc accactctca cagtctcctc agccaaaaca   360
acagccccat cggtctatcc actggcccct gtgtgtggag atacaactgg ctcctcggtg   420
```

```
actctaggat gcctggtcaa gggttatttc cctgagccag tgaccttgac ctggaactct    480
ggatccctgt ccagtggtgt gcacacc                                        507

<210> SEQ ID NO 63
<211> LENGTH: 648
<212> TYPE: DNA
<213> ORGANISM: Homo sapiens

<400> SEQUENCE: 63
gacgttgtga tgacccagtc tcaaaaattc ctgtccacat cagcaggaga cagggtcagc     60
atctcctgca aggccagtca gaatgtgggt actgctttag cctggtatca acagaaacca    120
ggacaatctc ctaaactttt gatttactcg gcatccaatc ggaacactgg agtccctgat    180
cgcttcacag gcaggggatt tgggacagat ttcactctca ccatcagcaa tatgcagtct    240
gaagacctgg cagattattt ctgccagcaa tatagcagct atccttacac gttcggaggg    300
gggaccaggc tggaaataaa gcgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctataccr gtgaggccac tcacaagaca    600
tcaacttcac ccattgtcaa gagcttcaac aggaatgaga cgcgttgt                 648

<210> SEQ ID NO 64
<211> LENGTH: 351
<212> TYPE: DNA
<213> ORGANISM: Homo sapiens

<400> SEQUENCE: 64
gaggtccagc tgcaacagtc tggacctgag ctggtgaagc ctggagcttc aatgaagata     60
tcctgcaagg cttctggtta ctcattcact gcctacacca tgaactgggt gaagcagacc    120
catggaaaga accttgagtg gattggactt attaatccat acaatggtgg tactagctac    180
aaccagaagt tcgaggacaa ggccacatta actgttgaca agtcatccaa cacagcctac    240
atggacctcc tcagtctgac atctgaggac tctgcagtct attattgtgc aagaagggac    300
tgggactact ttgactactg gggccaaggc accactctca cagtctcctc a             351

<210> SEQ ID NO 65
<211> LENGTH: 351
<212> TYPE: DNA
<213> ORGANISM: Homo sapiens

<400> SEQUENCE: 65
gaggtccagc tgcaacagtc tggacctgag ctggtgaagc ctggagcttc aatgaagata     60
tcctgcaagg cttctggtta ctcattcact gcctacacca tgaactgggt gaagcagacc    120
catggaaaga accttgagtg gattggactt attaatcctt acaatggtgg tactaactac    180
aaccagaagt tcgaggacaa ggccacatta actgtcgaca agtcatccaa cacagcctac    240
atggacctcc tcagtctgac atctgaggac tctgcagtct attattgtgc aagaagggac    300
tgggactact ttgactactg gggccaaggc accactctca cagtctcctc a             351

<210> SEQ ID NO 66
<211> LENGTH: 318
<212> TYPE: DNA
<213> ORGANISM: Homo sapiens
```

-continued

```
<400> SEQUENCE: 66
gacgttgtga tgacccagtc tcaaaaattc ctgtccacat cagcaggaga cagggtcagc        60
atctcctgca aggccagtca gaatgtgggt actgctttag cctggtatca acagaaacca       120
ggacaatctc ctaaactttt gatttactcg gcatccaatc ggaacactgg agtccctgat       180
cgcttcacag gcaggggatt tgggacagat ttcactctca ccatcagcaa tatgcagtct       240
gaagacctgg cagattattt ctgccagcaa tatagcagct atccttacac gttcggaggg       300
gggaccaggc tggaaata                                                     318
```

AGONIST ANTIBODIES AGAINST TSHR

The invention relates to antibodies, particularly human antibodies and fragments thereof that bind the thyroid stimulating hormone receptor (TSHR), especially in humans, and their uses in diagnostic and therapeutic roles.

The thyroid gland is, as is well known, one site of metabolic control within the body. Cancer of the thyroid gland is not particularly common, but the high rate of disease reoccurrence necessitates long term surveillance. Usually, during treatment for cancer of the thyroid, the majority of the thyroid tumor is removed, but a small amount often remains that must be treated by radiotherapy. Following surgery, it is necessary to treat the patient with thyroid hormone, as the patient will no longer produce this. One role of the thyroid gland is to take up iodine from the body. Hence, it should be possible to treat any remaining tumor cells with radioactive iodine. Unfortunately, though, thyroid cancer cells do not take up iodine well. So, in order for the radioactive iodine to work, the patient has to either be treated with recombinant TSH or have thyroid hormone treatment withdrawn in order to elevate natural TSH levels, to stimulate iodine uptake. However, a significant proportion of the treated patients fail to respond to recombinant TSH after some time. Moreover, recombinant TSH is very expensive and not all patients may be offered this treatment. Withdrawal of thyroid hormone has quite unpleasant side effects for the patient, particularly fatigue, muscle cramps, puffiness and constipation. It would be beneficial if a new cheaper treatment could be found that stimulated iodine uptake, without causing such unpleasant side effects.

Graves' disease is a common antibody-mediated disorder in which the primary target antigen has been identified as the thyroid follicular cell surface receptor for thyroid stimulating hormone (TSHR). One group of anti-TSHR antibodies behave as agonists, mimicking the action of the natural ligand, TSH, on the receptor and are known as thyroid stimulating antibodies (TSAbs). The TSAbs hyperstimulate the thyroid follicular cells to secrete thyroxine resulting in hyperthyroidism. Another group of anti-TSHR antibodies (TSBAb) may act as antagonists of TSH binding to the receptor which may occasionally lead to hypothyroidism. Neutral class antibodies to the TSHR that have neither agonist nor antagonist activity have also been described, although their role in disease remains to be clarified.

The treatment for Graves' disease has been standard for almost fifty years. It is very difficult to study Graves' disease because the antibodies involved in the disease are present at very low levels. It would be useful to have antibodies that stimulate the TSHR in order to further the studies into Graves' disease.

The TSHR belongs to the family of G protein coupled receptors (GPCRs) with a large extracellular domain, a seven transmembrane (TM) region and a short cytoplasmic tail. The TM region of the GPCRs is responsible for the transmission of the activating signal by regulating small secondary messengers such as cAMP, diacylglycerol and inositolphosphate (IP3). It is likely that the mode of TSHR activation and the consequent intracellular regulatory cascade may ultimately be responsible for the variations observed in different patients with regard to toxic hyperplasia (gland enlargement, goitre), extrathyroidal complications and response to treatment. The TSHR is unique among the large family of GPCRs in undergoing complex post-translational modifications such as cleavage into two disulphide-linked subunits, known as the A-subunit and the B-subunit. The A-subunit of 53 kD, corresponding to the ectodomain of TSHR is of special interest as it preferentially binds TSAbs and it has been proposed that the resulting, cleaved fragment released into the bloodstream may be the primary stimulus for provoking autoimmunity in susceptible individuals.

The isolation of TSAbs as monoclonal antibodies (mabs) has been a long sought goal, but has proved to be extraordinarily difficult to achieve. The establishment of experimental animal models of hyperthyroid Graves' disease has led to the development of IgG mabs with limited TSAb activity. At the same time, a human IgG mab to TSHR, developed from a patient with Graves' disease, was described with powerful thyroid activity in the nanogram range. The human mab acted as a full agonist by activating the TSHR to maximal stimulation equivalent to that achieved with sub-saturating concentrations of TSH. More recently, a murine mab developed from an experimental model, with similar efficacy, which behaves as a full agonist for the TSHR has also been described. Moreover, the mab was pathogenic in antibody transfer experiments in vivo and reportedly led to a lymphocytic infiltrate of the thyroid gland. The determinants on the receptor for the full agonist and other stimulatory and blocking murine mabs are dependent on the conformational, three dimensional folding of the ectodomain, residing in a region rich in leucine repeats within the horseshoe structure. The paucity of full agonist autoantibodies to TSHR present in patients' serum, precluded a comparison of their properties, which may impact on the pathogenesis of Graves' disease. The inventors have surprisingly developed two antibodies that have an extraordinarily high affinity for TSHR and consequently powerfully stimulate TSHR. Interestingly, the two mabs show full agonist activity to the TSHR, but also show subtle differences in their behavior at low concentrations of IgG in terms of antagonistic activity for the TSHR. The mabs are pathogenic in vivo when transferred into mice whereby a single injection of microgram quantities of IgG induces rapid hypersecretion of thyroxine leading to sustained hyperthyroidism with considerable morphological changes, but with minimal mononuclear cell infiltrate in the thyroid glands.

According to the invention, there is provided an antibody that binds to the TSHR, particularly to human TSHR with high affinity and specificity.

Accordingly, there is provided an antibody comprising a CDR comprising an amino acid sequence having substantial homology to an amino acid sequence selected from the sequences shown in FIGS.

8, 9, 10, 11, 12, 13, 14, 30, 31, 32, 33 and 34.

In particular, there is provided an antibody comprising a first CDR comprising an amino acid sequence having substantial homology to an amino acid sequence selected from the sequences shown in FIGS.

8, 9, 12 and 32;

a second CDR comprising an amino acid sequence having substantial homology to an amino acid sequence selected from the sequences shown in FIGS.

10, 13, 30, 31 and 33; and a third CDR comprising an amino acid sequence having substantial homology to an amino acid sequence selected from the sequences shown in FIGS.

11, 14 and 34.

Also provided is an antibody comprising a heavy chain comprising one or more CDRs having an amino acid sequence having substantial homology to an amino acid sequence selected from the sequences shown in FIGS.

8, 9, 10, 11, 30 and 31.

The invention further provides an antibody comprising a light chain comprising one or more CDRs having an amino acid sequence having substantial homology to an amino acid sequence selected from the sequences shown in FIGS. 12, 13, 14, 32, 33 and 34.

Additionally, there is provided an antibody comprising an amino acid sequence having substantial homology to an amino acid sequence selected from the sequences shown in FIGS. 15, 16, 17, 18, 19, 20, 21, 22, 23, 24, 25, 26, 27, 28, 35, 36, 37, 38, 39, 40, 41, 42 and 43.

The invention also provides an antibody comprising a heavy chain variable region having substantial homology to an amino acid sequence selected from the sequences shown in FIGS. 20, 21, 22, 23, 39 and 40.

Preferably the antibody has a light chain variable region having substantial homology to the amino acid sequence shown in FIGS. 24. Alternatively the antibody has a light chain variable region having substantial homology to the amino acid sequence shown in FIG. 41.

Also provided is an antibody comprising a light chain variable region having substantial homology to an amino acid sequence selected from the sequences shown in FIGS. 24 and 41.

In a further embodiment, there is provided an antibody comprising a CDR encoded by a nucleotide sequence having substantial homology to a nucleotide sequence selected from the sequences shown in FIGS. 44, 45, 46, 47, 48, 49, 50, 61, 62, 63, 64 and 65.

In particular, there is provided an antibody comprising:
1) a first CDR encoded by a nucleotide sequence having substantial homology to a nucleotide sequence selected from the sequences shown in FIGS. 44, 45, 48 and 63;
b) a second CDR encoded by a nucleotide sequence having substantial homology to a nucleotide sequence selected from the sequences shown in FIGS. 46, 49, 61, 62 and 64; and
c) a third CDR encoded by a nucleotide sequence having substantial homology to a nucleotide sequence selected from:
47, 50 and 65.

Also provided is an antibody comprising a heavy chain comprising one or more CDRs encoded by a nucleotide sequence having substantial homology to a nucleotide sequence selected from the sequences shown in FIGS. 44, 45, 46, 47, 61 and 62.

Additionally, there is provided an antibody comprising a light chain comprising one or more CDRs encoded by a nucleotide sequence having substantial homology to a nucleotide sequence selected from the sequences shown in FIGS. 48, 49, 50, 63, 64 and 65.

The invention further provides an antibody encoded by a nucleotide sequence having substantial homology to a nucleotide sequence selected from the sequences shown in FIGS. 51, 52, 53, 54, 55, 56, 57, 58, 59, 60, 66, 67, 68, 69, 70, 71, 72 and 73.

Also provided is an antibody comprising a heavy chain variable region encoded by a nucleotide sequence having substantial homology to a nucleotide sequence selected from the sequences shown in FIGS. 56, 57, 58, 59, 71 and 72.

Preferably the antibody comprises a light chain variable region encoded by a nucleotide sequence having substantial homology to the nucleotide sequence shown in FIG. 60. Alternatively the antibody comprises a light chain variable region encoded by a nucleotide sequence having substantial homology to the nucleotide sequence shown in FIG. 73.

Further provided is an antibody comprising a light chain variable region encoded by a nucleotide sequence having substantial homology to a nucleotide sequence selected from the sequences shown in FIGS. 60 and 73.

In another embodiment, there is provided an antibody that binds to the same epitope as an antibody according to other aspects of the invention.

In order that the invention may be better understood, certain terms are defined. Additional definitions may be found throughout the specification.

The term "antibody" is well known in the art. Herein it means an immunoglobulin or any functional fragment thereof. It encompasses any polypeptide that has an antigen-binding site.

It includes but is not limited to monoclonal, polyclonal, monospecific, polyspecific, non-specific, humanized, human, single-chain, chimeric, synthetic, recombinant, hybrid, mutated, grafted, and in vitro generated antibodies. The term "antibody" encompasses antibody fragments such as Fab, F (ab') 2, Fv, scFv, Fd, dAb, and any other antibody fragments that retain antigen-binding function. Typically, such fragments would comprise an antigen-binding domain. When preceded by the word "intact" the term "antibody" means a whole antibody molecule, namely two heavy chains, each with one variable region and three constant regions, and two light chains, each with one variable region and one constant region.

Intact antibodies are also known as immunoglobulins (Ig). As indicated above, intact antibodies comprise light chains and heavy chains. Light chains are classified into two isotypes, and heavy chains are classified into five isotypes (A, D, E, G, and M). Some heavy chain isotypes are further divided into isotype subclasses, e.g., 1gG1, IgG2, IgG3, and IgG4. It is particularly preferred that the antibodies of the invention are IgG antibodies. In particular, IgG2b and IgG2a antibodies are preferred.

The domain and three dimensional structures of different antibodies are known in the art. The light chain is composed of a constant domain (C) and an N-terminal variable domain (V). The heavy chain is composed of three or four constant domains ($C_H$), a hinge region, and a N-terminal variable domain ($V_H$). The $C_H$ adjacent to the $V_H$ domain is designated $C_{H1}$. The $V_H$ and $V_L$ domains contain four regions of conserved sequence called framework (FR) regions (FR1, FR2, FR3, and FR4), which form a scaffold for three regions of hypervariable sequence called complementarity determining regions (CDR). The CDRs (CDR1, CDR2, and CDR3) contain most of the antibody amino acids that specifically binds antigen. Heavy chain CDRs are denoted H1, H2, and H3, while light chain CDRs are denoted L1, L2, and L3. The term CDR is well known in the art. One skilled in the art would be able to recognise CDRs in an antibody or fragment by using Kabat numbering and the amino acids found either side of the CDRs.

The Fab fragment (Fragment antigen-binding) consists of $V_H$, $C_H1$, $V_L$, and —$C_L$ domains covalently linked by a disulfide bond between the constant regions. The Fv fragment is smaller and consists of $V_H$ and $V_L$ domains non-covalently linked. To overcome the tendency of non-covalently domains to dissociate, a single chain Fv fragment (scFv) can be constructed. The scFv contains a flexible polypeptide that links the C-terminus of $V_H$ to the N-terminus of $V_L$, or the C-terminus of $V_L$ to the N-terminus of $V_H$. A 15-mer $(Gly_4Ser)_3$ peptide may be used as a linker, but other linkers are well known.

The antibodies of the invention are preferably able to bind to the Thyroid Stimulating Hormone Receptor (TSHR), especially the human TSHR. The antibodies also preferably cross react with the mouse TSHR. Further they are preferably able to agonise that receptor, that is to stimulate the production of thyroid hormone. It is possible to screen for these functions using techniques well known in the art. A functional fragment is an antibody fragment that is still able to bind TSHR. Further, a functional fragment is preferably able to agonise TSHR.

The terms "antigen-binding site", "antigen-binding domain" and "antigen-binding fragment" mean the part of an antibody that specifically binds antigen. The part of the antigen that is recognised and bound by the antibody is referred to as the "epitope". An antigen-binding domain usually comprises variable regions from both the light chain ($V_L$) and the heavy chain ($V_H$), but it does not have to comprise both. Antigen-binding fragments include Fab fragments (monovalent fragments consisting of the $V_L$, $V_H$, $C_L$ and $C_{H1}$ domains); F(ab')$_2$ fragments (bivalent fragments comprising two Fab fragments linked by a disulfide bridge at the hinge region); Fd fragments (the two $V_H$ and $C_{H1}$ domains); Fv fragments ($V_L$ or $V_H$ domains, dAb fragments (Ward et al., (1989) Nature 341: 544-546), one or more complementarity determining regions (CDR); and single chain Fvs. The various antibody fragments can be obtained using conventional techniques known to those with skill in the art. It is possible to screen for the functionality of the fragments, e.g. binding and agonising a receptor using techniques known in the art.

As is known in the art, it is possible to use murine antibodies from mice and rats for therapy in humans. However, rodent antibodies tend to provoke strong Human anti-Murine Antibody (HAMA) immune responses which restricts their usefulness for repeated application in the same patient. Hence, the antibodies according to the invention are preferably chimeric, humanised (CDR grafted or reshaped).

The term "chimeric" refers to antibodies in which the whole of the variable regions of a mouse or rat antibody are expressed along with human constant regions. This provides the antibody with human effector functions and also reduces immunogenicity (HAMA) caused by the murine Fc region.

"Humanised" antibodies (also called CDR grafted or reshaped antibodies)" are an alternative to chimeric antibodies in which only the complimentarity determining regions from the rodent antibody V-regions are combined with framework regions from human V-regions. The idea is that these antibodies should be more human-like than chimeric and thus perhaps less immunogenic than chimeric antibodies.

It is also possible to obtain fully human antibodies from transgenic mice or other transgenic animals. Transgenic mice have been created which have a repertoire of human immunoglobulin germline gene segments. These mice when immunised thus make human like antibodies. B cells from such immunised mice may be used in the production of monoclonal antibodies.

All of these types of antibodies are encompassed by the invention.

The antibodies and nucleic acids of the invention are preferably isolated. The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The phrase "substantially homologous" means that the relevant amino acid or nucleotide sequence (e.g., CDR (s), $V_H$ or $V_L$ domain) will be identical to or have minor differences to the specifically defined sequences. Minor differences include minor amino acid changes, such as 1 or 2 substitutions in a 5 amino acid sequence of a specified region. In the case of antibodies, the second antibody has the same specificity and has at least 50% of the affinity of the same.

Sequences substantially identical or homologous (e.g., at least about 85% sequence identity) to the sequences disclosed herein are also part of this application. In some embodiments, the sequence identity can be about 90%, 91%, 92%, 93%, 94%, 95%, 96%, 97%, 98% or 99% or higher. In particular, when dealing with sequences of CDRs, substantial homology preferably means at least 90%, 91%, 92%, 93%, 94%, 95%, 96%, 97%, 98%, 99% homology. When dealing with longer sequences, such as the sequences of the light or heavy chain variable regions, homology may be at least 85%, 87%, 90%, 91%, 92%, 93%, 94%, 95%, 96%, 97%, 98% or 99%. Sequences including constant regions may have less homology, for example, 75%, 80%, 85%, 87%, 90%, 91%, 92%, 93%, 94%, 95%, 96%, 97%, 98% or 99% or higher. Substantially identical or homologous sequences also include nucleic acid sequences that will hybridize under selective hybridization conditions (e.g., highly stringent hybridization conditions), to the complement of the specifically defined strand. The percent identity can be determined by standard alignment algorithms, for example, the Basic Local Alignment Tool (BLAST) described by Altshul et al. ((1990) J. Mol. Biol., 215: 403-410); the algorithm of Needleman et al. ((1970) J. Mol. Biol., 48: 444-453); or the algorithm of Meyers et al. ((1988) Comput. Appl. Biosci., 4: 11-17). The percent identity between two amino acid or nucleotide sequences can also be determined using the algorithm of E. Meyers and W. Miller ((1989) CABIOS, 4: 11-17) which has been incorporated into the ALIGN program (version 2.0). This would be known by those skilled in the art.

The term "stringent" describes conditions for hybridization and washing. Stringent conditions are known to those skilled in the art and can be found in Current Protocols in Molecular Biology, John Wiley & Sons, N.Y. (1989), 6.3.1-6.3. 6.

Antibodies can be made by any method known in the art. A preferred method is using traditional hybridoma techniques (Kohler and Milstein (1975) Nature, 256: 495-499). For additional antibody production techniques, see Antibodies: A Laboratory Manual, eds. Harlow et al., Cold Spring Harbor Laboratory, 1988. No limitation is placed on the present invention as to method of production or source of antibody.

The invention provides antibodies that bind to TSHR. It is further envisaged that one skilled in the art could create more antibodies by altering the $V_H$ and/or $V_L$ sequence(s) provided. Such antibodies may be derived by a skilled person using techniques known in the art and are also encompassed by the invention. For example, modifications such as amino acid substitutions, deletions, or additions can be introduced into any part of the antibody, providing functionality remains. Changes may be introduced into the framework regions, especially to, for example improve the stability of the antibody. Changes may also be introduced into the CDRs to alter the antibody's affinity for the TSHR. The affinity of an antibody for the TSHR may be tested using standard techniques known in the art.

Conservative modifications to the $V_H$ and $V_L$, sequences are envisaged in particular. Such changes will produce molecules having functional and chemical characteristics similar to those of the antibodies from which the modifications are made. Conservative modifications are modifications unlikely to dramatically change the shape or function of the antibody, such as replacing one amino acid with another amino acid that has similar characteristics, e.g. replacing a hydrophobic amino acid with another hydrophobic amino acid.

When substituting amino acids, natural amino acids may be used, as may non-naturally occurring amino acids that have been created by, for example, chemical synthesis.

The antibodies according to the invention may be linked to other molecules. For example, antibodies may be linked to a protein or to a nonproteinaceous polymer such as polyethylene glycol, polypropylene glycol, and polyoxyalkylenes. Linking antibodies to such molecules is well known in the art and may be carried out by standard methods. Linking antibodies to such molecules can have an effect on certain characteristics of the antibodies, for example half life in blood.

Other molecules that may be linked to the antibody include detectable or functional tags or labels, such as enzymatic labels, e.g. horseradish peroxidase or alkaline phosphatase, radiolabels and chemical moieties e.g. biotin. The antibodies may also be linked to toxic agents such as toxins, cytostatic or cytotoxic molecules and radioisotopes. Alternatively, the antibodies may be linked to other antibodies.

In a particularly preferred embodiment, the antibodies are linked to radioactive iodine.

Linking such molecules to antibodies is well known in the art and may be achieved by standard techniques, for example by covalent attachment.

The invention also provides methods of making antibodies, including a method of generating an antibody or functional fragment thereof comprising:

a) providing a repertoire of nucleic acids encoding a variable domain that either includes a CDR1, CDR2 or CDR3 encoding region to be replaced or lacks a CDR1, CDR2 or CDR3 encoding region;
b) combining the repertoire with a donor nucleic acid having a nucleotide sequence substantially homologous to a sequence selected from the sequences in FIGS. 44, 45, 46, 47, 48, 49, 50, 61, 62, 63, 64 and 65 to provide a repertoire of nucleic acids encoding a variable domain; and
c) expressing a nucleic acid from the repertoire.

When replacing or inserting a nucleotide sequence encoding a CDR, one skilled in the art would use standard techniques and would know whether the CDR sequence could be inserted in isolation or whether framework regions should also be inserted. The skilled person would be able to make appropriate changes to the framework region if necessary.

The term "repertoire" refers to a genetically diverse collection of nucleotide sequences derived wholly or partially from sequences encoding immunoglobulins. The sequences may be generated by the method given above, or by rearrangement in vivo of the V, D, and J segments of heavy chains, and the V and J segments of light chains. Alternatively, the sequences can be generated from a cell in response to which rearrangement occurs, e.g., in vitro stimulation. Alternatively, part or all of the sequences may be obtained by DNA splicing, nucleotide synthesis, mutagenesis, and other methods, see, e.g., U.S. Pat. No. 5,565,332.

The method may additionally comprise selecting an antibody that binds TSHR from the expressed antibodies and isolating it. It may include the step of selecting an antibody that agonises TSHR from the expressed antibodies and isolating it.

The invention also provides isolated nucleic acids encoding antibodies according to the invention including nucleotides encoding the CDRs, variable domains and other functional fragments of such antibodies, and substantially homologous sequences. The nucleic acids may comprise DNA or RNA, and they may be synthetic (completely or partially) or recombinant (completely or partially).

The nucleotide sequences provided and references thereto encompass DNA molecules with the specified sequence, and encompass RNA molecules with the specified sequence in which U is substituted for T.

A nucleic acid may encode any part of the antibody for example, a CDR, a variable region, a light chain, a heavy chain, an scFv, a Fab, the entire antibody or any other functional fragment thereof.

Particularly provided is an isolated nucleic acid having substantial homology to a sequence selected from: the sequences shown in FIGS.
44, 45, 46, 47, 48, 49, 50, 51, 52, 53, 54, 55, 56, 57, 58, 59, 60, 61, 62, 63, 64, 65, 66, 67, 68, 69, 70, 71, 72 and 73.

The nucleic acids of the invention are substantially homologous to the sequences provided. In particular, the sequences are preferably at least 85%, 90%, 91%, 92%, 93%, 94%, 95%, 96%, 97%, 98%, 99% homologous to the sequences provided.

The invention also provides constructs such as plasmids, vectors, transcription or expression cassettes, which comprise at least one nucleic acid according to the invention.

Also provided is a host cell comprising at least one such construct.

Further provided is a the method of making an antibody comprising culturing host cells under appropriate conditions so they express the antibody from the nucleic acid. Following expression and production, any desired fragment or antibody may be isolated and/or purified using any suitable technique, then used as appropriate.

Systems for cloning and expressing polypeptides in a variety of host cells are known in the art. Suitable host cells include mammalian cells, insect cells, plant cells, yeast cells, or prokaryotic cells, e.g., *E. coli*. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells.

It is particularly preferred that the antibodies of the invention are monoclonal antibodies. Monoclonal antibodies may be produced by standard methods, as first described by Kohler and Milstein.

In particular, the antibodies may be produced using a hybridoma. There is provided a first hybridoma having ECACC accession number 06032901. Also provided is a second hybridoma having ECACC accession number 06032902.

Also provided is an antibody produced by a hybridoma according to the invention, or a functional fragment thereof.

Additionally provided is a method of producing an antibody comprising culturing a hybridoma according to the invention under conditions that allow expression of the antibody and isolating the antibody from the culture.

A hybridoma, as is well known in the art, is a cell created artificially by fusion of a tumour cell with a B-lymphocyte. Such cells are produced in the standard method of producing monoclonal antibodies, as first described by Kohler and Milstein.

The antibodies of the invention have multiple uses. Firstly, they may be used to further the studies into TSHR and Graves' disease.

Secondly, the antibodies also have therapeutic and diagnostic uses. In one use, the antibodies may be used to target cancer cells, especially thyroid tumor cells and metastases of thyroid tumors. The antibodies may be used to deliver radioactive compounds such as radioactive iodine to the tumor cells ("magic bullets") or to stimulate the tumor cells to take up radioactive iodine for both diagnostic and therapeutic purposes. When the tumor cells take up radioactive iodine, they are killed. They can also be identified by scanning for radioactivity using either the magic bullet approach or the radioactive iodine uptake procedure.

There is provided a pharmaceutical composition comprising an antibody according to the invention.

The composition is suitable for administration to patients. In addition to the antibody, it may comprise one or more appropriate pharmaceutical excipient(s) such as solvents, dispersion media, coatings, antibacterial and antifungal agents, isotonic and absorption delaying agents. The preparation of pharmaceutical compositions and the use of excipients is well known in the art. Other active compounds may also be included. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may be possible to create compositions which may be topically or orally administered, or which may be capable of transmission across mucous membranes. For example, the administration may be intravenous, intraperitoneal, intramuscular, intracavity, subcutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, CremophorELT™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminium monostearate and gelatin.

Oral compositions include an inert diluent or edible carrier. The composition can be enclosed in gelatin or compressed into tablets. For the purpose of oral administration, the antibodies can be incorporated with excipients and prepared as tablets or capsules, for example. The oral composition may also contain, for example, a binder, an excipient, a lubricant and flavourings.

Compositions may also be administered by a transmucosal or transdermal route. For example, antibodies that comprise a Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of composition containing ointments, salves, gels, or creams known in the art. For transmucosal or transdermal administration, penetrants appropriate to the barrier to be permeated are used.

For administration by inhalation, antibodies are delivered in an aerosol spray from a pressured container or dispenser, which contains a propellant (e.g., liquid or gas) or a nebulizer.

In certain embodiments, antibodies of this invention are prepared with carriers to protect the antibodies against rapid elimination from the body. Biodegradable polymers (e.g., ethylene vinyl acetate, polyanhydrides, polyglycolic acid, collagen, polyorthoesters, polylactic acid) are often used.

Methods for the preparation of such pharmaceutical compositions are known by those skilled in the art.

Antibodies or compositions according to the invention may be administered in therapeutically effective amounts, as determined, based on, for example, the patient's weight, gender, age and medical condition. The antibodies or compositions may be administered in a single dose, as a bolus or as continuous therapy.

The term "effective amount" refers to a dosage or amount that is sufficient to stimulate TSHR activity to produce thyroid hormone or to stimulate the uptake of iodine.

As used herein, the terms "subject" and "patient" are intended to include human and non-human animals. Subjects may include a human patient having a thyroid cancer or a metastasis of thyroid cancer.

The term "non-human animals" of the invention includes all vertebrates, such as non-human primates, sheep, dogs, cows, chickens, amphibians, reptiles, etc.

Additionally, there is provided an antibody or functional fragment thereof according to the invention for use in therapy.

In particular, the invention provides the use of an antibody or functional fragment thereof according to the invention, in the preparation of a medicament for the diagnosis or treatment of cancer.

The term cancer refers especially to cancers of the thyroid gland and to metastases of such cancers.

Also provided is a method of locating tumor cells comprising:
1) administering an antibody according to the invention to a patient;
2) subsequently administering a radioactive compound to the patient;
3) scanning the patient for the presence, localisation or accumulation of radioactive iodine; and
4) generating an image of the patient.

Further provided is a method of locating tumor cells comprising:
1) administering an antibody conjugated to a radioactive compound according to the invention to a patient;
2) scanning the patient for the presence, localisation or accumulation of the radioactive compound; and
3) generating an image of the patient.

Preferably the radioactive compound is readioactive iodine.

Additionally provided is a method of treating tumor cells comprising:
1) administering an antibody according to the invention to a patient;
2) subsequently administering radioactive iodine to the patient.

A method of treating tumor cells comprising:
1) administering an antibody conjugated to radioactive iodine according to the invention to a patient.

Antibodies according to the invention may also be used in assays, such as competition assays for the presence of anti-TSHR antibodies. There is provided a kit for assaying for the presence of anti-TSHR antibodies in a sample, comprising a support to which TSHR molecules are bound and labeled antibodies according to the invention.

Also provided is a method of assaying for the presence of anti-TSHR antibodies, comprising:
a) providing a support to which TSHRs are bound;
b) applying labeled antibodies according to the invention to the support;
c) applying a test sample to the support; and
d) assaying the displacement of the antibodies.

In this method, the labeled antibodies bind to the TSHRs and the amount of antibodies bound may be measured. If there are anti-TSHR antibodies in the test sample, they will compete with labeled antibodies to bind to the TSHRs. The amount of anti-TSHR antibodies in the sample can be assayed by measuring the difference in amount of labeled antibodies bound before and after application of the sample. Competition assays of this nature are well known and appropriate techniques and support apparatus could be used by those skilled in the art. A labeled antibody is an antibody to which a detectable label has been attached. Suitable labels are well known in the art and examples are discussed above.

It is useful to be able to detect anti-TSHR antibodies in a sample to diagnose, for example, Graves' disease or hypothyroidism in a patient. The method provided above could be used as a diagnostic method, in which the test sample is a sample of serum taken from the patient.

The invention will now be described in detail, by way of example only, with reference to the figures:

FIG. 1

Dose response curves of thyroid stimulating antibody activities (TSAbs) of KSAb1 and KSAb2 IgG and Fab fragments assessed by bio-assay in CHO cells stably transfected with human TSHR. Varying concentrations of KSAb1 IgG (■-■) and Fab fragments (■---■) and KSAb2 IgG (▲—▲) and Fab fragments (▲-.-.-▲) (in ng/ml) were added to CHO cells stably transfected with human TSHR in (A) salt-free isotonic HBSS buffer containing sucrose and HEPES or (B) physiological isotonic HBSS buffer containing NaCl and the stimulated cAMP measured (in pmol/ml) as described in Materials and Methods. The cAMP responses of a sub-saturating dose of bTSH in the salt free and physiological isotonic medium were 164 and 157 pmol/ml respectively. The results shown are representative of at least three independent experiments performed in triplicate.

FIG. 2

Thyroid stimulating blocking activity (TSBAbs) of KSAb1 (□) and KSAb2 (■) IgG measured in JPO9 cells using a sub-saturating concentration of 40 µU bTSH. The TSBAb activity, expressed as % inhibition of TSH induced cAMP, was calculated as described in Materials and Methods. Different concentrations of KSAb1 and KSAb2 IgG were examined to ensure that the blocking activity was not dependent upon the antibody concentration. The results shown are representative of at least two independent experiments performed in triplicate.

FIG. 3

Dose response curves of TSH binding inhibiting immunoglobulins (TBII) activity of KSAb1 IgG (■-■) and Fab fragments (■---■) and KSAb2 IgG (▲—▲) and Fab fragments (▲-.-.-▲) using TRAK (DYNOtest human) kits. Different concentrations of IgG or Fab fragments (ng/ml) diluted in normal human serum were added to the human TSHR coated tubes for the assay. The results shown are representative of at least three independent experiments performed in triplicate.

FIG. 4

Measurement for antibody affinity (Kd) of (A) KSAb1 and (B) KSAB2 IgG by saturating binding experiments using human TSHR coated tubes from TRAK (DYNOtest human) kits as a source of immobilized receptor and $^{125}$I-labeled mab (approximately 2.5 µCi/ml) with or without increasing concentrations of unlabeled IgG. IC50 and Kd values were calculated using Excel. The antibody affinity was expressed as reciprocal Kd values (L/mol). Non specific binding using an irrelevant IgG mab (GAD1) was <5%. All determinations were performed in duplicate samples.

FIG. 5

Competition studies using $^{125}$I-labeled KSAb1 IgG or Fab fragments and KSAb2 IgG or Fab fragments with (A) patients' serum (B) between KSAb1 and KSAb2 IgG and (C) between KSAb1 and KSAb2 Fab fragments for binding to immobilized human TSHR. Serum from patients with Graves' disease (n=6) and hypothyroid patients with high levels of TSBAbs (n=6) were used. As controls, normal human serum (n=4) from individuals with no family history of autoimmune disease were utilized. The results are expressed as $^{251}$I-IgG binding. The results show the broad spectrum of inhibitory activity of all sera from Graves' disease patients and TSBAb positive hypothyroid patients with $^{125}$I-labeled KSAb1 or KSAb2 IgG confirming that the monoclonal antibodies bound similar autoreactive epitopes on TSHR to those recognized by patients' sera. The control normal serum gave negligible inhibition (<15%).

FIG. 6

Serum thyroxine (TT4) levels at various time points in BALB/c female mice following passive transfer of (A) KSAb1 IgG (■-■) and (B) KSAb2 IgG (▲—▲) by intravenous injection. The TT4 values (µg/ml) in individual mice from each group (n=3) are shown at time 0 (prior to injection of mab), 7, 26 and 70 hrs. The result of administration of KSAb2 IgG by intraperitoneal injection is shown in (C). Control mice treated with irrelevant IgG (GAD1 mab) are also shown (_13_).**p<0.01

FIG. 7

Histology of thyroid glands from mice following passive transfer of KSAb1 or KSAb2 IgG to induce hyperthyroid disease. Panel A, thyroid from control GAD1 treated mouse; panels B and C, KSAb1 IgG at doses of 10 and 100 µg respectively; Panel D, detailed view of collapsed follicles from panel B; Panels E and F, KSAb2 IgG at doses of 10 and 100 µg respectively. Magnification ×60. Apoptotic epithelial cells within colloid (→) and follicles without colloid showed epithelial cell lining of columnar and cuboidal cells with multilayering (--→).

FIGS. 8 to 73 show sequences (SEQ ID NOS: 1-66, respectively) of antibodies that are examples of the invention. The figures show various fragments of two antibodies. The fragment to which each figure relates is defined in Table 2.

FIG. 74

SDS Polyacrylamide gel electrophoresis of purified rFab preparations under reducing conditions. The H-chain fragment of the rFab is labelled with an arrow. M=standard molecular weight markers.

FIG. 75

TSH binding inhibition activities of KSAb1 and KSAb2 IgGs (labelled as IgG 9 and IgG17 respectively) and purified rFab fragments (labelled as Fab 9 and Fab 17 respectively) assessed in TRAK assay.

FIG. 76

Thyroid stimulating antibody activities of KSAb1 and KSAb2 IgGs (labelled as IgG 9 and IgG17 respectively) and purified rFab fragments (labelled as Fab 9 and Fab 17 respectively) assessed in isotonic HBSS buffer containing sucrose.

FIG. 77

TSH binding inhibition activities of KSAb1 and KSAb2 IgGs (labelled as IgG 9 and IgG17 respectively), purified rFab fragments (labelled as Fab 9 and Fab 17 respectively) and L-chain swaps of the rFab fragment (labelled as Fab 9.1-17L and Fab 17.4-9L respectively) assessed in TRAK assay.

FIG. 78

Thyroid stimulating antibody activities of KSAb1 and KSAb2 IgGs (labelled as IgG 9 and IgG17 respectively), purified rFab fragments (labelled as Fab 9 and Fab 17 respectively) and L-chain swaps of the rFab fragments (labelled as Fab 9.1-17L and Fab 17.4-9L respectively) assessed in isotonic HBSS buffer containing sucrose.

FIG. 79

Alignment of VH and VL gene sequences of thyroid stimulating antibodies with the corresponding murine V-region gene family.

EXAMPLES

Materials and Methods

Measurement of TSHR Antibodies and Thyroid Function Tests.

Depending on the samples for assessment, antibodies to TSHR were measured using two different types of TSH binding inhibition assays (porcine TRAK RIA and TRAK II [DYNOtest human] kits) (BRAHMS GmbH, Germany) requiring 50 µl and 100 µl neat serum respectively, essentially according to the manufacturer's instructions (1). The results were expressed as percentage inhibition of $^{125}$I-TSH binding. TSAb and TSBAb activities were measured by bioassay using CHO cells stably transfected with human TSHR, 24 h after seeding 30,000 cells/well in flat bottomed 96-well plates (1, 2). Prior to the assay, the medium was replaced with sodium chloride free isotonic Hank's buffered solution (HBSS) containing sucrose and HEPES supplemented with 0.5 mM isobutyl-1-methylxanthine (IBMX, Sigma-Aldrich) to inhibit phosphodiesterase activity (1, 2). Assays were also conducted in physiological sodium chloride containing isotonic HBSS, where sucrose was replaced with 130 mM NaCl. Bovine TSH (bTSH, Sigma-Aldrich) (40 µU/ml), test serum (3 µl) or purified IgG diluted in the appropriate HBSS medium was added to each well in triplicates and incubated for 4 h at 37 C. The cAMP released into the medium was measured by RIA (R&D systems) and the results expressed as pmols/ml or stimulation over basal value obtained with medium, as described (2). TSBAbs were detected similarly by adding a sub-saturating dose of bTSH (40 µU/ml) with test sample or control serum and measuring the reduction in TSH mediated stimulation of cAMP, as previously described (2). In our laboratory, the inter- and intra-assay coefficients of variation for TSAbs have been measured as <16% and <14% and for TSBAbs were <24% and 11% respectively (2). Total thyroid hormone (TT4) was determined by RIA with 25 µl of serum (D S Labs, UK), using serum from four normal BALB/c animals for determination of basal values.

Recombinant Adenoviruses

Recombinant adenovirus expressing the human TSHR holoreceptor (TSHR-Ad) was constructed using the AdEasy Adenoviral Vector system (Quantum Biotechnologies). Briefly, TSHR cDNA (26) was excised from pBluescript IISK—by digestion with KpnI and NotI and ligated into the adenovirus transfer vector (pShuttleCMV) (Quantum Biotechnologies). After linearisation of the pShuttleCMV/hT-SHR CMV vector with PmeI and treatment with alkaline phosphatase, the linear DNA was co-transformed by electroporation into electrocompetent E. coli BJ5183 together with supercoiled plasmid containing viral DNA, pAdEasy-1. Recombinants were selected in kanamycin, extracted and digested with PacI to expose the ITRs and finally transfected into HEK293A cells to generate viral particles. Adenovirus containing human TSHR-A subunit (amino acids 1 to 289) (referred to as A-subunit-Ad) used. Adenovirus expressing β-galactosidase was used as control and prepared using the AdEasy system. All virus constructs were propagated in HEK293 cells and purified twice over CsCl gradient centrifugation (3, 4), dialysed against PBS and viral concentration determined by optical absorbance at 280 nm. Purified adenoviruses were aliquoted and stored at −80 C.

Immunization and Selection of Animals for Hybridomas

All mice were obtained from Harlan UK Ltd.

Recombinant adenovirus expressing the human TSHR holoreceptor (TSHR-Ad) was constructed using the AdEasy Adenoviral Vector system (Quantum Biotechnologies). Briefly, TSHR cDNA (1) was excised from pBluescript IISK— by digestion with KpnI and NotI and ligated into the adenovirus transfer vector (pShuttleCMV) (Quantum Biotechnologies). After linearisation of the pShuttleCMV/hT-SHR CMV vector with PmeI and treatment with alkaline phosphatase, the linear DNA was co-transformed by electroporation into electrocompetent E. coli BJ5183 together with supercoiled plasmid containing viral DNA, pAdEasy-1. Recombinants were selected in kanamycin, extracted and digested with PacI to expose the ITRs and finally transfected into HEK293A cells to generate viral particles. Adenovirus containing human TSHR-A subunit (amino acids 1 to 289) (referred to as A-subunit-Ad) was obtained (3, 4). For A-subunit-Ad injections, a low dose immunization protocol of $10^9$ particles was used (4). Female BALB/c mice (16 animals, age 7-8 weeks) were immunized as described and bled one week and three weeks after the second injection and tested individually for TSAb activity. The animals with consistently elevated TSAb activity received a third injection of A-subunit-Ad. One week later, this was followed by a booster intraperitoneal injection of CHO cells expressing TSHR ectodomain via a GPI-anchor ($2 \times 10^6$ cells in 500 µl PBS) (5). The animals were sacrificed three days later and the spleens removed aseptically for hybridoma production, followed by collection of blood by cardiac puncture for serum and excision of thyroid glands for histological analysis. All animal experiments were performed under approval of the Home Office Regulations (United Kingdom) and King's College London, with full veterinary welfare care.

Screening of Hybridomas and Cloning

Spleen cell suspensions were fused with X63-Ag8653 myeloma cells at a ratio of 5:1 using PEG fusion medium for hybridoma production (50% solution, Immune Systems Ltd, UK) in RPMI medium containing 20% FCS, 2 mM sodium pyruvate, 2 mM L-glutamine and 0.01% PSF (all from Invitrogen, UK) and plated into 96 well plates. Hybridomas were selected under hypoxanthine, aminopterine and thymidine (HAT medium, Invitrogen) and HT medium (Immune Systems Ltd). The supernatants (1000 from wells showing growth were tested for TBII activity using TRAK H (DYNOtest human) kits. Positive wells were expanded and subcloned twice at 0.3 cells/well in medium supplemented with 10 to 20% Hybridoma feeder supplement, Doma Drive (Immune Systems Ltd). The hybridomas were isotyped using Mouse Monoclonal Isotyping kit (Serotec, UK). IgG was purified from tissue culture supernatants by protein-A SEPHAROSE™ chromatography (6), purity assessed by SDS polyacrylamide gel electrophoresis and quantified for protein by Bradford protein assay.

Preparation of Fab Fragments

Fab fragments were prepared from IgG by digestion with papain (Sigma-Aldrich), using 2.5 mg IgG, 1 M cysteine (25 .mu.1), 20 mM EDTA (25 .mu.1) and 1 mg/ml papain in acetate buffer (5 .mu.1) and incubated overnight at 37 C. (6). Following addition of 100 mM iodoacetamide (110 .mu.1) to terminate the reaction, the digest was mixed with protein-A SEPHAROSE™ for 1 h at 4 C. After a brief microfuge centrifugation step, the supernatant was collected and dialysed overnight against PBS. The purity of the Fab fragments was examined by SDS polyacrylamide gel electrophoresis and TSHR reactivity confirmed by assessing TBII activity.

Iodination of IgG and Fab Fragments and Displacement Studies 0.25 nM of IgG or Fab fragments of KSAb1 or KSAb2 in 10 .mu.1 PBS were labeled with 5.mu.1 $^{125}$I-Na using iodogen coated tubes by incubating for 10 min at room temperature. Free isotope was removed by gel filtration in SEPHAROSE™ G25 columns and specific activity calculated (7). Antibody affinity was measured by saturation binding analysis. Briefly, different concentrations of $^{125}$I-labeled IgG of KSAb1 or KSAb2 were added in duplicates to human TSHR coated tubes (from TRAK II [DYNOtest human kit), resuspended in binding buffer from the kit in 200 .mu.1 final volume and incubated overnight in the cold room to reach equilibrium. After washing the tubes 3 times in washing buffer from the kit, the bound $^{125}$I-IgG was measured by counting the radioactivity in a gamma counter (DPC laboratories, UK). Non specific binding was subtracted and the Kd values calculated at 50% saturation using Excel software. The affinity results were expressed as reciprocal Kd values (L/mol).

Competition studies were carried out similarly to above: Different concentrations of unlabeled IgG or Fab fragments were resuspended in binding buffer (from TRAK II [DYNOtest human kit) in a final volume 200 µl and added to human TSHR coated tubes from the kit. After 2 h incubation with shaking at room temperature, the tubes were washed twice with washing buffer from the kit. A sub-saturating concentration of $^{125}$I-labeled KSAb1 or KSAb2 IgG was added, incubation continued for 1 h and the tubes washed and counted in a gamma counter. For competition with sera from Graves' patients, 100 µl serum was added to the human TSHR coated tubes as described above. The inhibition of binding of $^{125}$I-labeled KSAb1 or KSAb2 was determined and expressed as percentage inhibition.

Injection of KSAb1 and KSAb2 IgG for In Vivo Stimulation of Thyroid Gland

Injection of different doses of purified IgG of KSAb1 or KSAb2 was performed by the intravenous and the intraperitoneal route. Female BALB/c mice (18 animals, age 7-8 weeks) were treated with a single intravenous injection in the tail vein of KSAb1 or KSAb2 IgG in sterile PBS (50 µl) containing 10 µg or 100 µg antibody (3 mice per group). Another group of mice were treated with a single intraperitoneal injection of KSAb2 IgG in sterile PBS (100 µg). For controls, animals were injected intravenously with isotype matched, 100 µg IgG mab specific for the islet cell antigen, glutamic acid decarboxylase (mab GAD-1). All animals were bled at time 7, 28 and 70 h post injection and serum TT4 levels were determined. Mice were sacrificed at 70 h and thyroid glands excised for histological analysis.

Thyroid Histology

Thyroid glands were fixed in formalin and processed in formalin. Sections were stained with hematoxylin and eosin for morphological analysis. Immunohistochemistry was performed for the detection of B and T cells on the fixed thyroid sections with anti-mouse CD20 followed by detection with the ImmunoCruz anti-goat kit (Santa Cruz Biotechnology), rat anti-mouse CD4 and CD8 mabs followed by detection with biotinylated anti-rat antibody (Vector laboratories, UK) and a strepavidin-biotin peroxidase conjugate (Dako, Denmark). Antigen retrieval was performed prior to staining by pressure cooking at pH 6.0 for CD20 and CD8 antibodies, and at pH 9.0 for CD4 antibody.

Results

BALB/c mice were immunized with recombinant adenovirus expressing the TSHR holoreceptor (TSHR-Ad) and the TSHR-A subunit (A-subunit-Ad) to induce Graves' hyperthyroid disease. Initial assessment for anti-TSHR antibodies was performed for TSAbs in individual sample bleeds of all animals.

One week after the second injection, nine animals were positive (56%) for TSAb activity, ranging from 3.1 to 92.6 fold increased activity over basal levels (Table 1). Eleven animals (68%) showed significant elevation of serum TT4 levels and hence were hyperthyroid (Table 1). These results are in complete agreement with those of Chen and colleagues (4). One animal from this group with the highest, stable TSAb levels was selected for hybridoma production and boosted with a third injection of A-subunit-Ad, followed one week later by an intraperitoneal injection of CHO cells expressing high levels of human TSHR ectodomain linked by the glycosylphosphatidylinositol anchor to the plasma membrane cell surface, to expand the antibody secreting splenic B cell population. Serum from the selected animal at sacrifice showed it to be hyperthyroid with elevated TT4 (134 µg/ml, control BALB/c mice 56.25+/−8.26 µg/ml), as well as being highly positive for TBII activity with 87% inhibition of $^{125}$I-TSH binding.

Monoclonal Antibodies

Culture supernatants (100 µl) were collected from 70-80% confluent wells and tested neat for TBII activity using TRAK II [DYNOtest human) kits. A total of 250 wells were screened, resulting in 3 positive wells (well 9, 98%; well 17, 96% and well 233, 80% inhibition). Upon expansion, the TBII activity of well 233 primary cell line declined rapidly. The remaining two lines were cloned twice at 0.3 cells per well and renamed KSAb1 and KSAb2, which have been in continuous culture for >7 months. The H- and L-chain subtypes for KSAb1 and KSAb2 were shown to be IgG2b/k and IgG2a/k respectively.

Thyroid Stimulating Activity of the Mabs

Both KSAb1 and KSAb2 IgG stimulated cAMP production in CHO cells stably transfected with human TSHR. Initial dose response studies were conducted in NaCl-free sucrose containing medium routinely used for its increased sensitivity for detecting TSAbs (8). As shown in FIG. 1A, in dose response studies both KSAb1 and KSAb2 IgG showed typical sigmoid curves by stimulating TSHR to reach >98% of the response achieved with a sub-saturating dose of bTSH. However, although both the mabs show full agonist activity by achieving near maximal cAMP stimulatory responses, they showed differences in their cAMP stimulatory responses at lower doses of IgG. Thus, overall KSAb1 and KSAb2 showed maximal stimulation of 199 and 183 fold over basal value, with 3 fold stimulation obtained at 1.2 ng/ml and 2.2 ng/ml IgG respectively (FIG. 1A). The $EC_{50}$ values for KSAb1 and KSAb2 IgG were determined to be 9.4 ng/ml and 93 ng/ml respectively (FIG. 1A). Fab fragments of KSAb1 and KSAb2 also gave similar TSAb responses to the intact parental IgG (FIG. 1A) and therefore also behaved as full agonists for the TSHR.

Figure 1B:
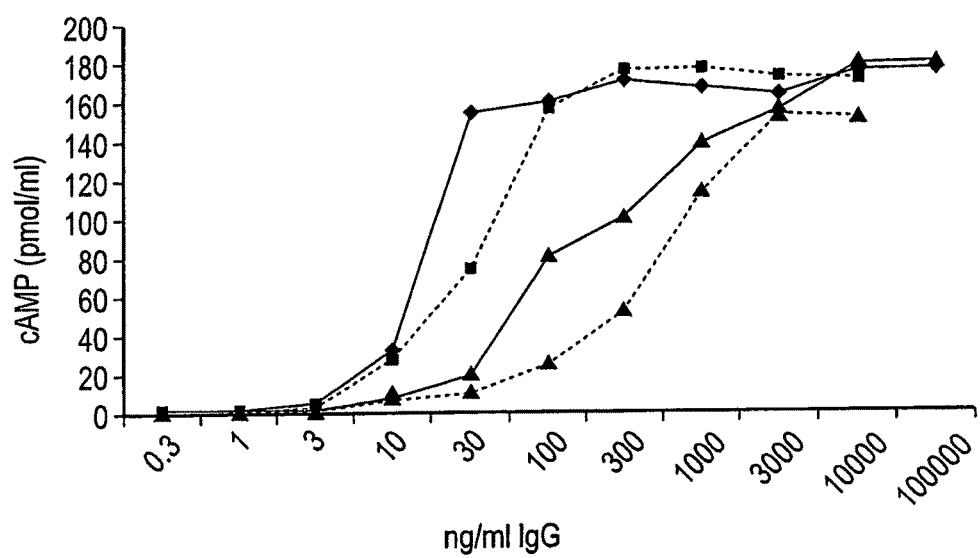

We also performed dose response studies under physiological salt concentrations, although these assay conditions demonstrate reduced sensitivity compared to the use of salt free sucrose containing isotonic HBSS buffer (8). The dose response for TSH induced cAMP production was not altered significantly in the NaCl containing buffer, with 40 μU/ml giving maximal stimulation (not shown). Importantly, both KSAb1 and KSAb2 IgG continued to show full agonist activity with maximal cAMP stimulatory responses reaching >98% of the response obtained with sub-saturating dose of bTSH (FIG. 1B). Typical sigmoid dose response curves were observed, which again at lower doses showed differences in the cAMP stimulatory activity of KSAb1 and KSAb2 IgG (FIG. 1B). Under the physiological salt conditions, KSAb1 and KSAb2 continued to be active at concentrations of <1 ng/ml and 3 ng/ml respectively. The IgGs showed $EC_{50}$ values in the nM range of 16.5 ng/ml and 100 ng/ml respectively (FIG. 1B). Moreover, Fab fragments of KSAb1 and KSAb2 also showed similar efficacies of cAMP stimulation (FIG. 1B).

Blocking of TSH Mediated Stimulation (TSBAb) Activity

Figure 2:
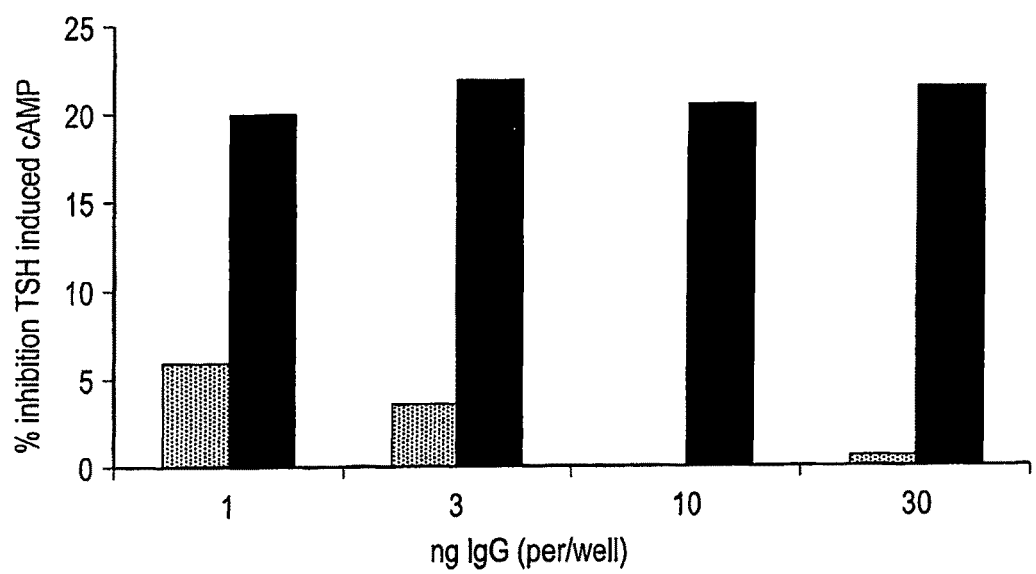

The ability of KSAb1 and KSAb2 IgG to block TSH mediated stimulation of cAMP in JP09 cells was measured in a TSH mediated stimulation blocking assay. Different concentrations of IgG were examined in the assay to ensure that the blocking activity was not dependent upon the antibody concentration. Whilst KSAb1 showed negligible TSBAb activity, KSAb2 IgG showed a reproducible >20% TSBAb activity in all antibody concentrations tested (≤30 ng/well) equivalent to 240 ng/ml, which were below the sub-saturating concentration of agonist activity for KSAb2. Consequently, KSAb2 acted with weak antagonism to TSH mediated stimulation of cAMP (FIG. 2). Interestingly, neither KSAb1 nor KSAb2 IgG demonstrated reactivity with any specific peptide in a complete set of synthetic peptides of TSHR ectodomain by ELISA (2), giving compelling evidence on the recognition of conformational epitopes on the receptor (not shown).

TSH Binding Inhibiting Immunoglobulin (TBII)

Figure 3:
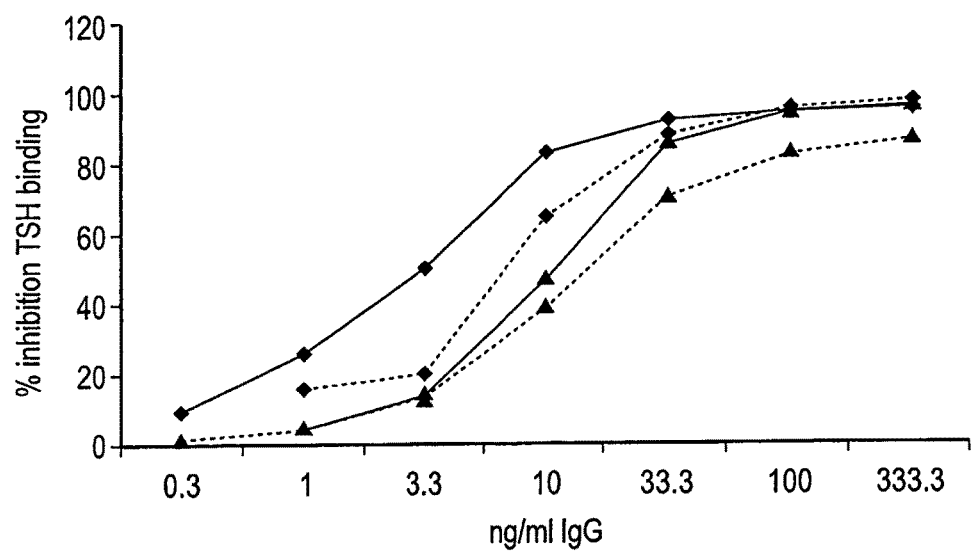

In TBII assays using TRAK II [DYNOtest human] kits, dose response analysis of KSAb1 and KSAb2 IgG showed concentrations of 3.3 ng/ml and 10 ng/ml were sufficient to give 50% inhibition of $^{125}$I-TSH binding activity (FIG. 3). Moreover, for both the mabs, 20% inhibition was achieved at concentrations of 0.7-4.4 ng/ml, whilst 100 ng/ml was sufficient to give 95% inhibition (FIG. 3). Fab fragments gave similar TBII activity to the intact, parental IgG (FIG. 3).

Competition Studies with KSAb1 and KSAb2

Figure 4A:
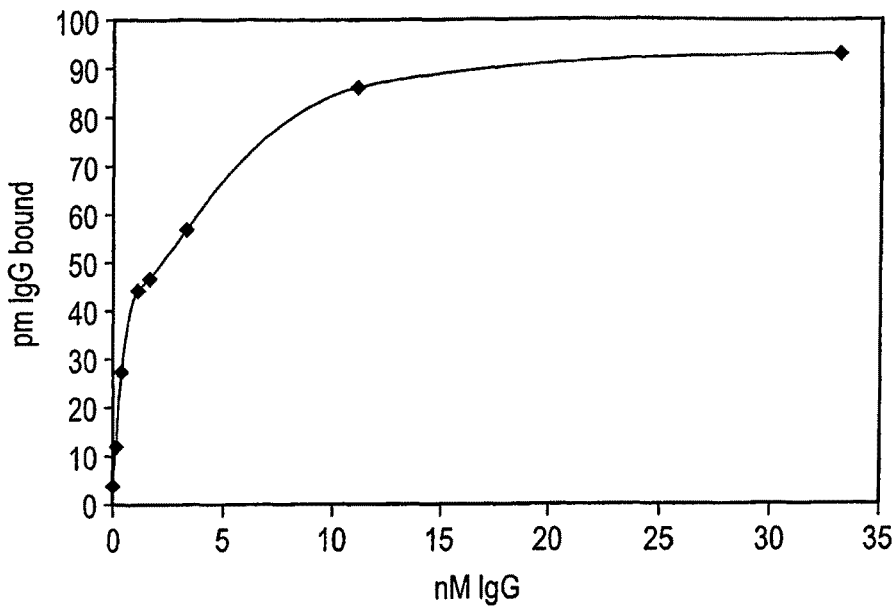
Figure 4B:
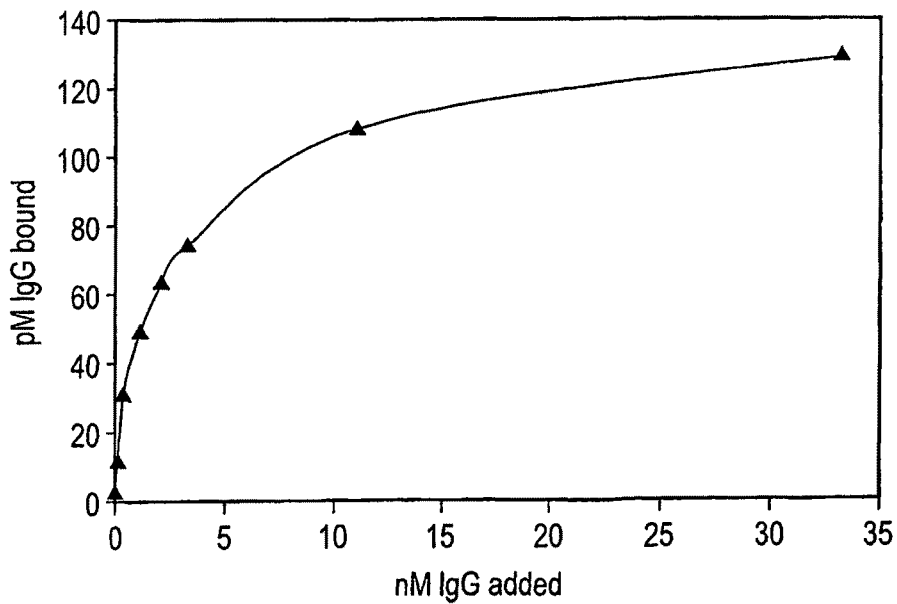
Figure 5A:
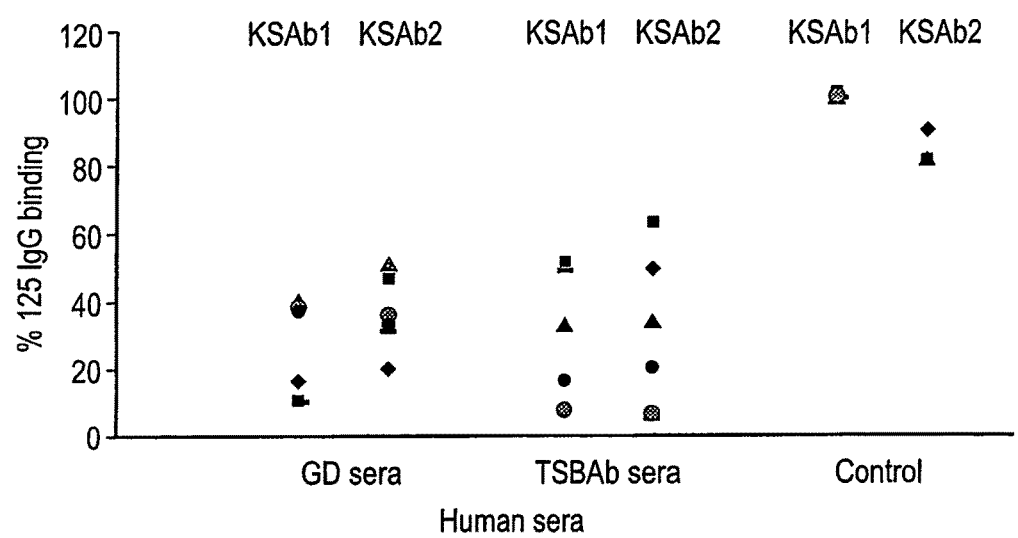
Figure 5B:
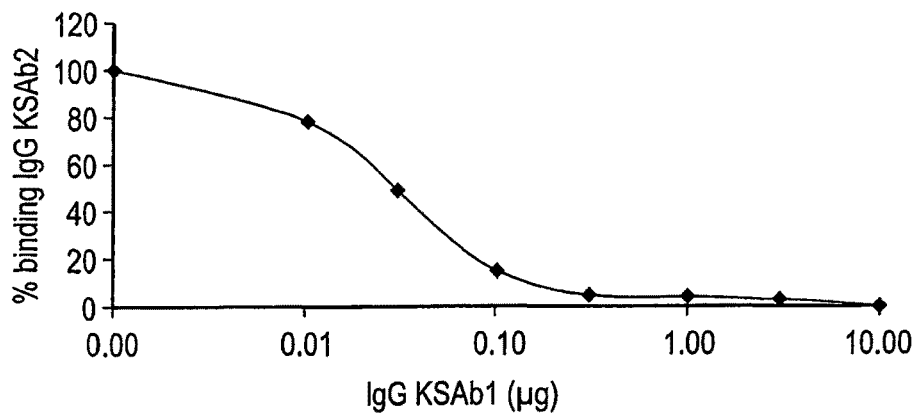
Figure 5C:
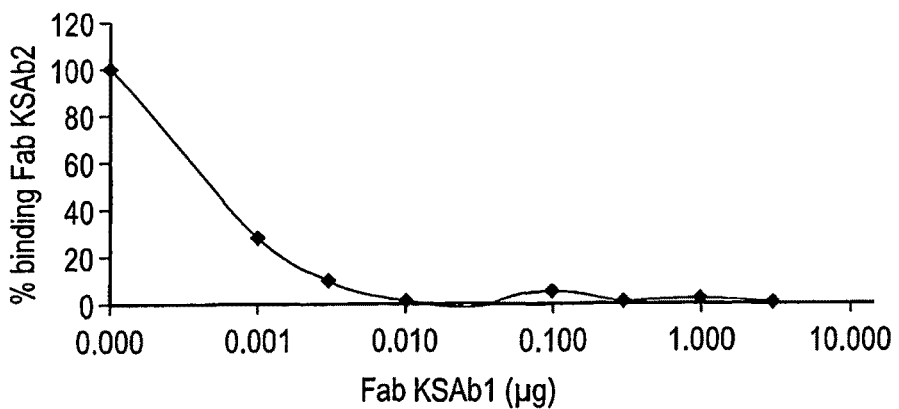

By saturation binding analysis using human TSHR coated tubes (from TRAK II [DYNOtest human] kits), both $^{125}$I-labeled KSAb1 and KSAb2 IgG bound the receptor with high affinity, with Kds of $4.5 \times 10^{10}$ L/mol and $6.25 \times 10^{10}$ L/mol respectively (FIG. 4). The labeled IgG and Fab fragments of the mabs were then used as tracers in competition studies to study the epitopes on the receptor. We investigated whether labeled KSAb1 and KSAb2 IgG displaced heterogeneous autoantibodies to TSHR from Graves' disease patients. Serum from normal individuals, with no family history of autoimmunity were used as controls. As shown in FIG. 5A, sera from Graves' disease patients inhibited the binding of KSAb1 or KSAb2 to the immobilized receptor. Furthermore, although different sera competed to a similar degree with both labeled KSAb1 and KSAb2 IgG, the sera varied in their inhibitory activity, indicating the heterogeneous nature of anti-TSHR autoantibodies in serum from different patients (FIG. 5A). To investigate the autoimmune determinants on TSHR present in other conditions, we assessed sera with strong blocking activity from autoimmune hypothyroid patients which also competed in binding to the receptor with labeled KSAb1 or KSAb2 IgG (FIG. 5A). Finally, using sub-saturating concentrations of $^{125}$I-IgG on human TSHR coated tubes, both KSAb1 and KSAb2 IgG competed with each other showing that their epitopes overlapped on the TSHR (FIG. 5B). Moreover, Fab fragments of KSAb1 and KSAb2 also competed with each other, indicating the close association of their determinants on the TSHR (FIG. 5C).

Displacement studies using labeled KSAb1 and KSAb2 IgG as tracers were also performed with another panel of anti-TSHR IgG mabs which are specific for linear determinants on the receptor and which show negligible thyroid stimulatory activity (9). Neither KSAb1 or KSAb2 IgG showed any competition with the mabs A10, A9 and A7 which are specific for residues located in the amino, middle and the carboxy-terminal regions of the receptor respectively (9) (not shown). Thus the stimulatory epitopes on the TSHR are different from the linear epitopes recognized by this panel of anti-TSHR mabs.

Passive Transfer Studies on KSAb1 and KSAb2 IgG

Figure 6A:
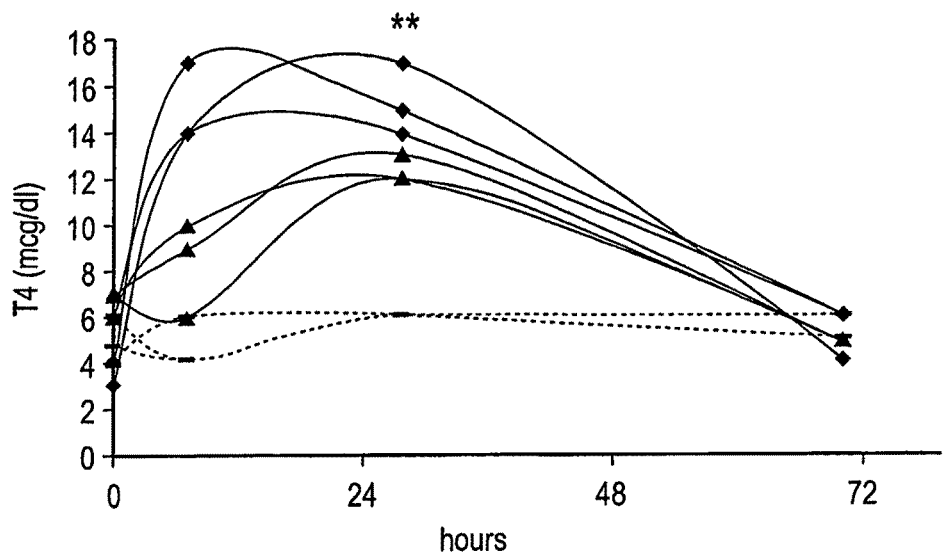
Figure 6B:
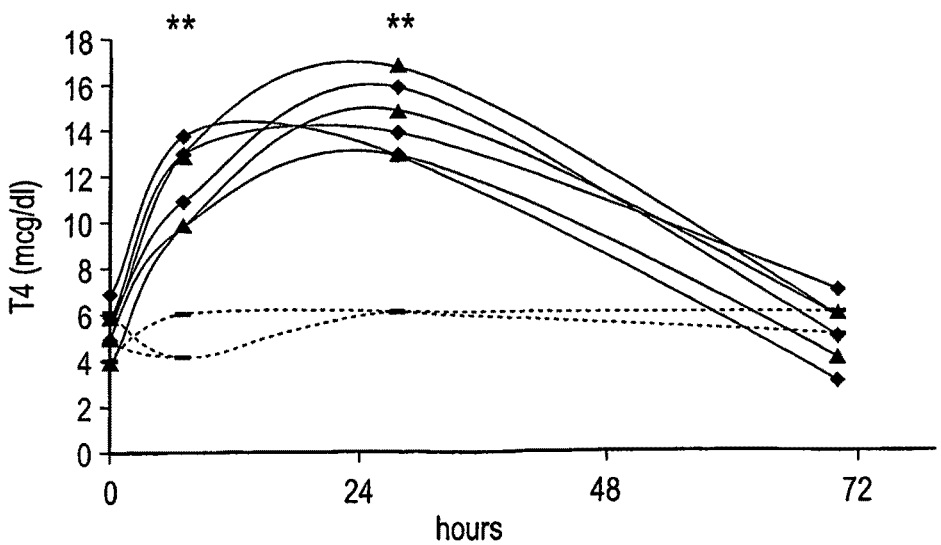
Figure 6C:
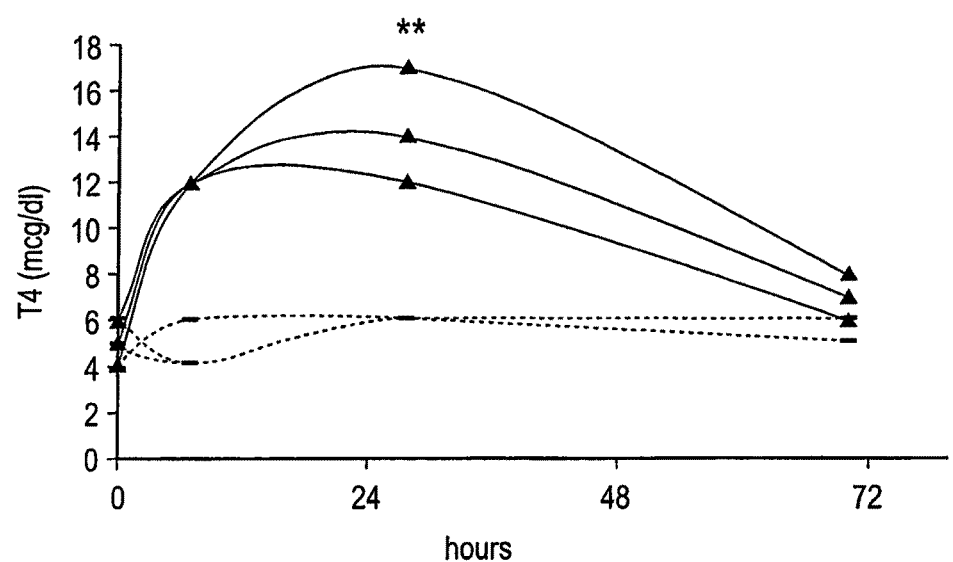
Figure 75:
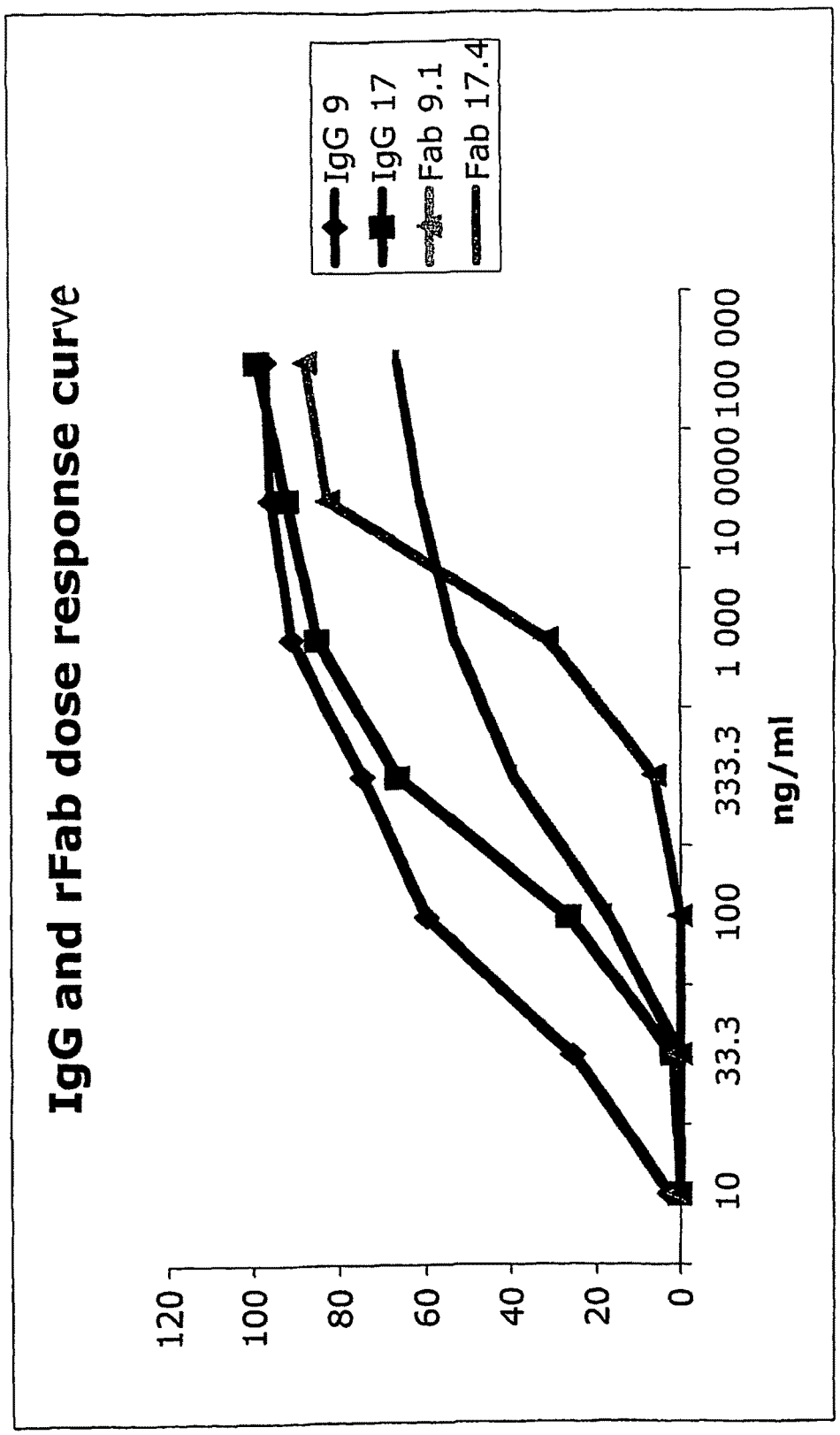
Figure 76:
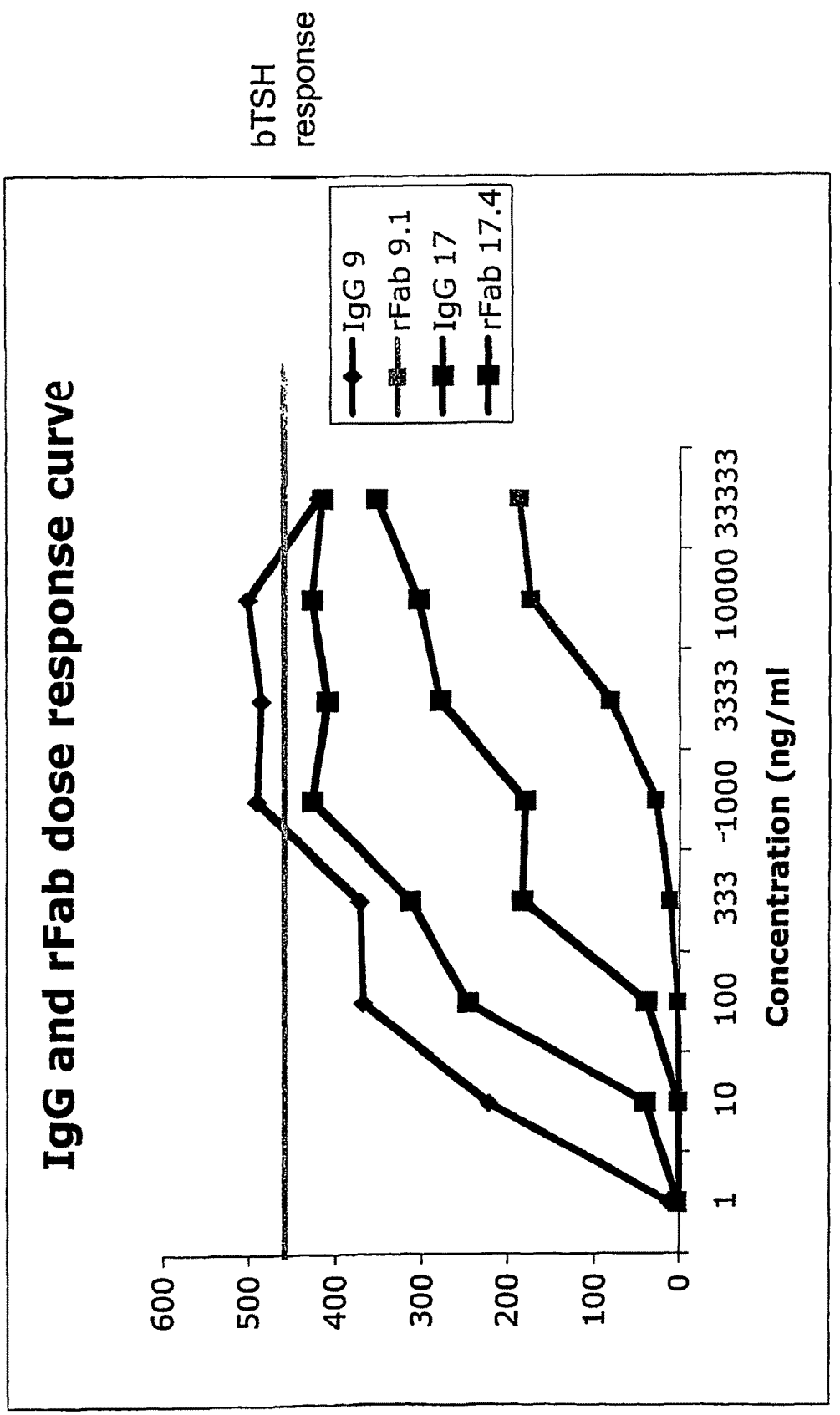
Figure 77:
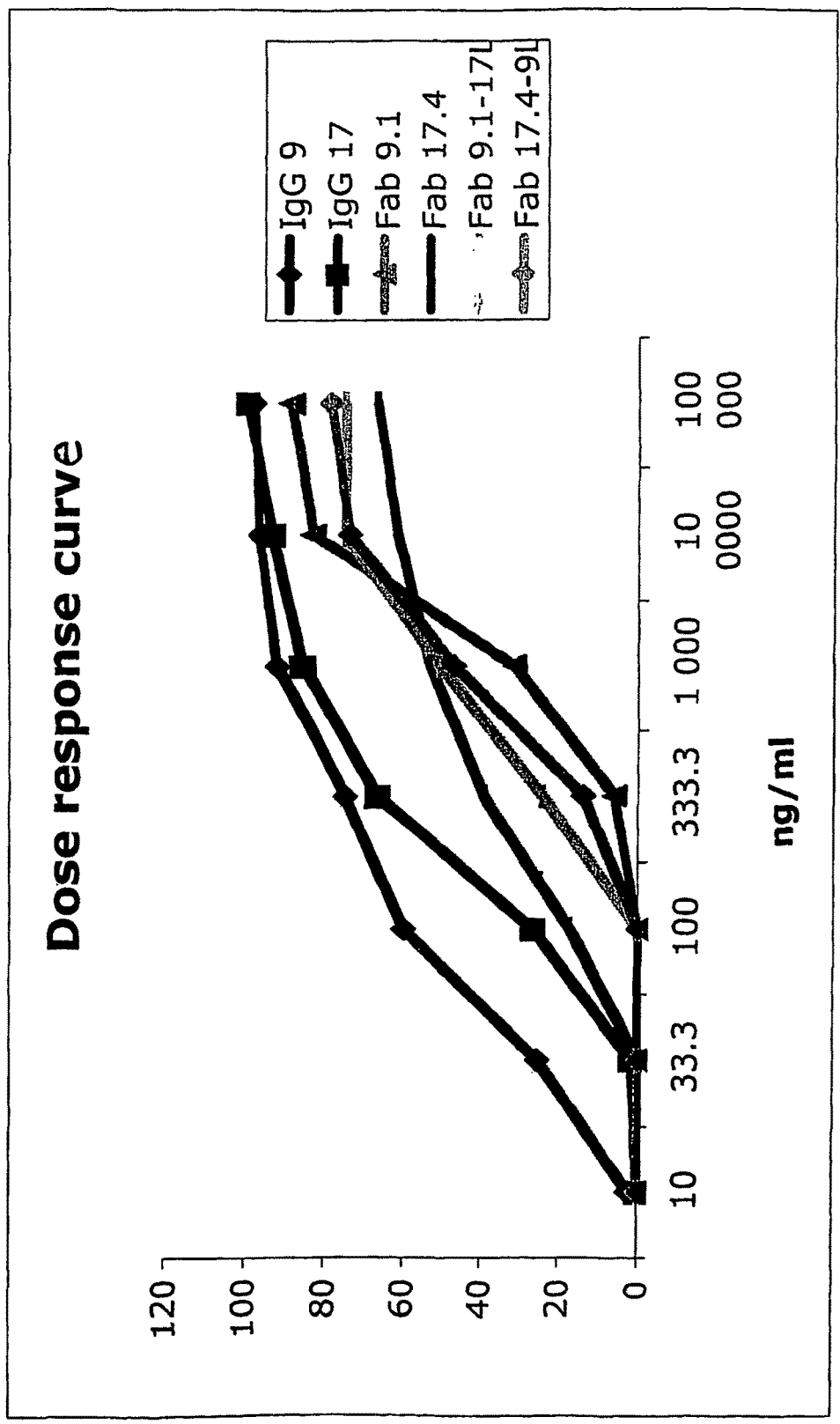
Figure 78:
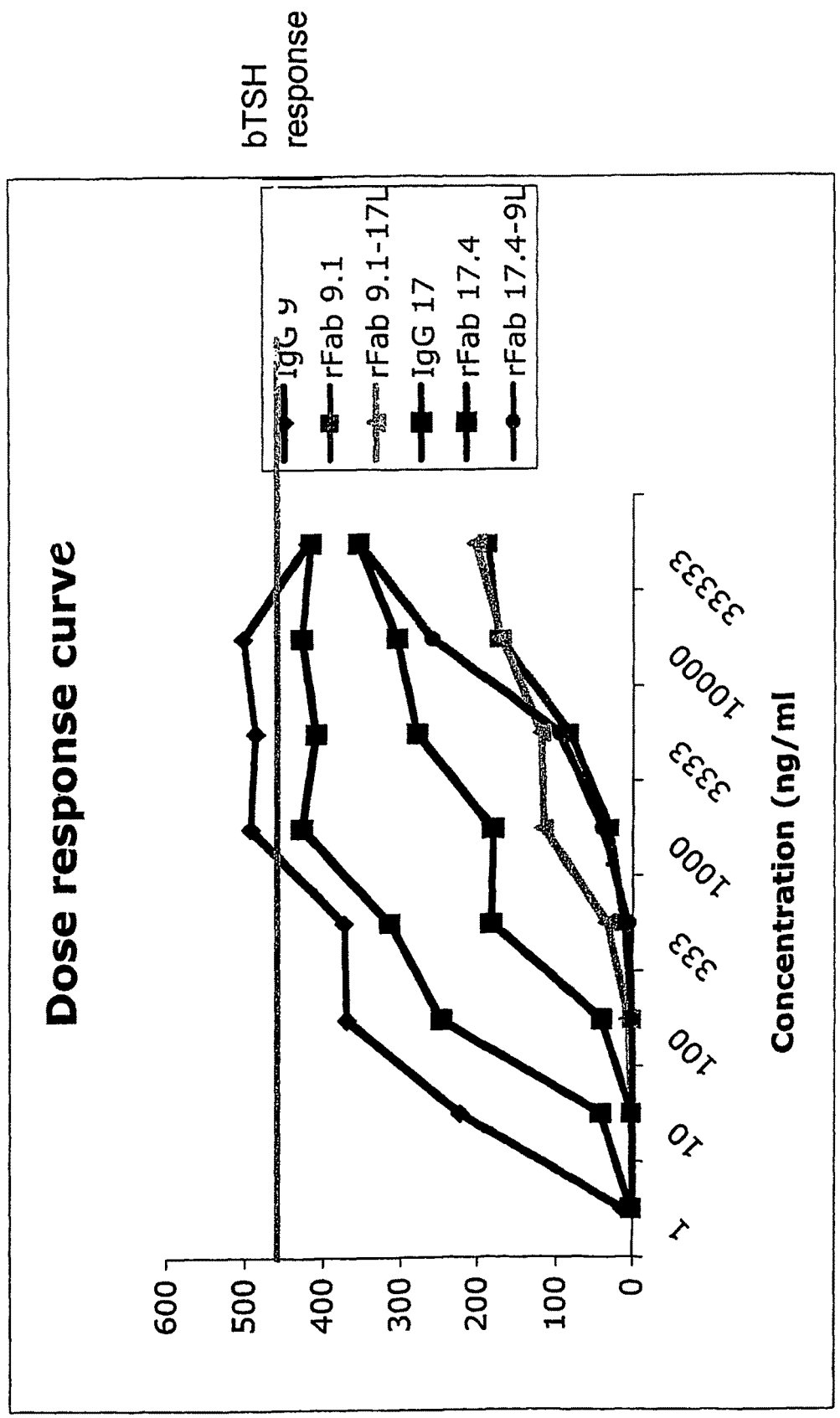

We assessed the effect of in vivo injection of KSAb1 and KSAb2 IgG into naïve mice in terms of inducing hyperthyroidism. We anticipated KSAb1 and KSAb2 to cross react with mouse TSHR since the two mabs were derived from a mouse which was significantly hyperthyroid. Two IgG doses of 10 g and 100 μg of each mab were injected iv into mice and the induced hyperthyroxinaemia determined at different time points. As control, isotype matched mab GAD1 to a pancreatic islet cell antigen was used. The results in FIG. 6 show that both KSAb1 and KSAb2 IgG are pathogenic, with a dose of 10 μg or 100 μg KSAb1 and 100 μg KSAb2 resulting in a rapid thyroid stimulatory response characterized by hyperthyroxinaemia within 7 hrs of administration. Serum thyroxine levels returned to baseline by 70 h. Injection of KSAb2 at a dose of 10 μg demonstrated a more delayed response in elevating TT4 levels, peaking at 28 hrs (FIG. 6). We also examined the effect of intraperitoneal injection of KSAb2 IgG, which paralleled the stimulation mediated by intravenous delivery (FIG. 6). These results also confirm cross reactivity of KSAb1 and KSAb2 to mouse TSHR.

Histological analysis of the thyroid glands from KSAb1 and KSAb2 treated mice showed both follicular and epithelial changes compared to the glands from the animals treated with the control mab (FIG. 7, panels A-F). In contrast to the thyroid gland from the control GAD1 mab treated animals (FIG. 7, panel A), the thyroid follicles from KSAb1 and KSAb2 IgG treated mice were of variable size and shape, with focal areas exhibiting total loss of luminal colloid associated with collapse of follicular lumina; in other areas, the colloid appears pale, thin and also finely vacuolated (FIG. 7, panel B-E). Moreover, the follicles containing the pale colloid were lined with flattened and attenuated epithelial cells, whilst the follicles without colloid showed epithelial cell lining of columnar and cuboidal cells with multilayering (broken arrows in FIG. 7. Moreover, individual necrotic cells were found to be present within the luminal colloid and also within the follicular lining epithelium with picnotic nuclei (shown in FIG. 7, panel F). Finally, histological analysis of the H&E sections revealed no mononuclear cell infiltrate into the glands of the KSAb1 and KSAb2 IgG treated animals, irrespective of the dose or the route of administration (FIG. 7, panel B-F). This was further substantiated by immunohistochemical staining of the thyroid glands, whereby staining with antibodies to mouse CD4, CD8 and CD20 failed to identify any B or T cell infiltrate (not shown).

Comparison of Fragments with Antibody

Heavy and light chain variable region fragments, the sequences of which are shown in FIG. 79, were expressed as rFab fragments in *E. coli*, purified and tested for binding to TSHR by a TSH binding inhibition assay and by measuring cAMP accumulation following TSHR stimulation. Both fragments bound to TSHR. Differences in binding between the fragments and the antibodies may be due to steric hindrance in the fragments, resulting from the expression system used. Results of the assays are shown in FIGS. 75 and 76.

Antibodies are Clonally Related

Investigation of the evolutionary development of the two antibodies indicate that they both arise from the same precursor naïve B cell. The antibodies have identical germline gene rearrangements. There are a large number of somatic hyper mutations in the $V_H$ and $V_L$ regions. However, whilst the $V_H$ regions clearly have a common ancestor and have a large number of mutations in common, the $V_L$ regions do not have such conserved sequences. Without being bound by a particular theory, the inventors postulated that the $V_H$ region contributes a predominant role in the agonist function in the antibodies and fragments. To confirm this, the inventors swapped the light chains of the antibodies and performed TSH binding inhibition and cAMP assays, the results of the assays are shown in FIGS. 77 and 78. The results indicate that the $V_H$ regions are important in determining function.

Discussion

The generation of mabs with agonist activity for the TSHR has been a long sought goal for a number of laboratories that has only recently been attained (10). Progress in this achievement has been dependent on the establishment of viable experimental models of antibody-induced hyperthyroidism. However, the one major exception has been the notable achievement of a human IgG monoclonal antibody with all the essential properties of a bona-fide pathogenic antibody (11). Among the several thyroid stimulating mabs derived from experimental models, only one showed full agonist activity and potencies that matched those present in the human disorder (12). The mabs described in this study, KSAb1 and KSAb2 fall into this category of disease associated antibodies as they display (i) full agonist activity for the human TSHR (ii) potency in nanogram quantities of IgG (iii) high affinity for human TSHR in $10^{10}$ L/mol range and (iv) in vivo pathogenicity with the induction of hyperthyroidism.

Our results show that the epitopes of KSAb 1 and KSAb2 on TSHR are likely to be conformational in nature and overlap with autoreactive determinants recognized by patients' autoantibodies. Their epitopes on the TSHR are likely to be close and intimately associated with each other since the smaller, Fab fragments of the KSAb1 and KSAb2 also compete for binding to the receptor. Additionally, our finding that these epitopes also overlap with the determinants associated with strong antagonism for TSH binding to the TSHR is in agreement with previous studies on the close relationship of the receptor epitopes associated with receptor stimulation and TSH antagonism (12, 13).

The notable aspects of our studies with KSAb1 and KSAb2 are based on the derivation of two thyroid stimulating mabs with full agonist TSHR activity, allowing us to compare their behaviour. KSAb1 and KSAb2 have comparable affinities and exhibit differences in cAMP generation, particularly at very low doses of TSH.

Antibodies with potent TSAb activity are pathogenic and directly responsible for the hyperthyroid status. Examination of serum thyroxine levels in individual mice showed that a number of animals where the hormone levels failed to correlate with serum TSAb activity. This was not surprising since a lack of concordance is also recognized both in human patients and in various models of induced Graves' disease (1, 3, 14, 15). We confirmed, in an acute study, by passive transfer of KSAb1 and KSAb2 IgG that these antibodies led to rapid hyperthyroidism in the animals. Moreover, the intraperitoneal route of injection of KSAb 2 also led to elevated serum TT4 levels, whose kinetics paralleled the intravenous route. The differences in potency between KSAb1 and KSAb2 observed at lower doses in the in vitro experiments were also apparent in the in vivo studies. Thus intravenous injections of a lower dose of 10 μg IgG of KSAb2 showed delayed kinetics of induced hyperthyroidism in the animals, in contrast to the induced hyperthyroidism with KSAb1 which showed similar induction of elevated serum thyroxine at the 10 and 100 μg tested doses. However, once maximal serum thyroxine levels were achieved with either the 10 or the 100 μg doses of either KSAb1 or KSAb2 IgG, hormone levels declined with similar kinetics until reaching basal levels by 70 h after injection.

Interestingly, histological analysis of the thyroid glands at 70 h post injection showed morphological changes suggestive of both stimulatory and cytotoxic effects. The stimulatory effects were characterized by proliferative epithelial changes as evident by foci of hyperplastic follicles with loss of colloid formation associated with multilayering and luminal collapse. The cytotoxic effects were present as individual cell necrosis within the lining epithelium and dying thyrocytes present within the colloid material. These cytotoxic effects are likely to be mediated as a result of the increased thyroid hormone production induced in the gland by the TSAbs, leading to a massive accumulation of hydrogen peroxide within the apical surface of the thyroid follicles (16, 17). There was no evidence of a mononuclear cell infiltrate, such as that present in the glands of patients with Graves' disease. It is possible that a prolonged chronic study of mab administration may lead to inflammatory changes within the thyroid gland, but it is interesting that in a similar acute study with their potent TSAb mab, the group of Costagliola and colleagues (12) reported a mononuclear cell infiltrate into the glands of their hyperthyroid mice. As the time frame in their study following the single injection of the TSAb mab was similar to that in the acute study in this report, this suggests that perhaps antibodies to different epitopes on the TSHR may be linked to the inflammatory reaction in the thyroid gland (12). Another recent study from Davies and colleagues used a hamster mab to TSHR with weaker TSAb activity than that reported in this study (18) to examine both the acute and chronic effects of the mab administration to mice (19). Although it is difficult to draw correlates of the hamster mab with the powerful stimulating mabs reported herein, it is interesting that chronic stimulation failed to induce hyperthyroxinaemia in the animals, but did lead to desensitization of the receptor, as well as considerable morphological changes such as hypertrophy and colloid depletion in the thyroid glands (19). Nevertheless, there was no reported mononuclear cell infiltration into the thyroid glands of the animals following chronic stimulation with the hamster mab (19).

The development of potent thyroid stimulating mabs such as KSAb1 and KSAb2 opens the way to a molecular dissection of the TSHR and the epitopes associated with autoimmune disease. Mapping of the conformational epitopes on the TSHR recognized by KSAb1 and KSAb2 may be performed by phage random peptide library screening in conjunction with mutagenesis (20). This will help in the characterization of the epitopes associated with thyroid stimulation on the TSHR and their modes of intracellular signaling. An understanding of these signaling events may also be relevant to the complications of Graves' disease such as TAO and pretibial myxoedema. Finally, generation of anti-idiotypic antibodies to KSAb1 and KSAb2, to identify individual clonotypes of anti-TSHR antibody specificities present in patients with Graves' disease may allow studies in the future to correlate their response to treatment and hence tailor therapies for individual patients without risk of relapse.

TABLE 1

Serum thyroid stimulating antibody activities and thyroxine levels in BALB/c mice immunized with Adenovirus TSHR A subunit, measured one week following second immunization. Eleven animals (68%) were hyperthyroid (shown in bold).

| Mouse | cAMP (pmol/ml) (1 week after 2$^{nd}$ immunization) | TT4 (µg/ml) |
|---|---|---|
| 1 | 3.8 | 100 |
| 2 | 2.0 | 66 |
| 3 | 0.8 | 100 |
| 4 | 1.2 | 81 |
| 5 | 16.6 | 134 |
| 6 | 59.2 | 56 |

TABLE 1-continued

Serum thyroid stimulating antibody activities and thyroxine levels in BALB/c mice immunized with Adenovirus TSHR A subunit, measured one week following second immunization. Eleven animals (68%) were hyperthyroid (shown in bold).

| Mouse | cAMP (pmol/ml) (1 week after 2$^{nd}$ immunization) | TT4 (µg/ml) |
|---|---|---|
| 7 | 1.9 | 89 |
| 8 | 4.0 | 213 |
| 9 | 37.3 | 237 |
| 10 | 2.0 | 84 |
| 11 | 6.1 | 101 |
| 12 | 18.1 | 107 |
| 13 | 1.9 | 138 |
| 14 | 1.5 | 148 |
| 15 | 1.4 | 63 |
| 16 | 1.8 | 60 |
| Control BALB/c mice | | |
| 17 | 0.6 | 44 |
| 18 | 0.5 | 62 |
| 19 | 0.5 | 60 |
| 20 | 0.8 | 59 |

TABLE 2

Amino acid and nucleotide sequences shown in the figures:

| | KSAb1 Amino acids | KSAb2 Amino acids | KSAb1 Nucleotides | KSAb2 Nucleotides |
|---|---|---|---|---|
| Heavy chain CDR1 | 8, 9 | 8 | 44, 45 | 44 |
| Heavy chain CDR2 | 10 | 30, 31 | 46 | 61, 62 |
| Heavy chain CDR3 | 11 | 11 | 47 | 47 |
| Light chain CDR1 | 12 | 32 | 48 | 63 |
| Light chain CDR2 | 13 | 33 | 49 | 64 |
| Light chain CDR3 | 14 | 34 | 50 | 65 |
| Heavy chain Fab | 15, 16, 17, 18 | 35, 36, 37 | 51, 52, 53, 54 | 66, 67, 68, 69 |
| Light chain Fab | 19 | 38 | 55 | 70 |
| Heavy chain V domain | 20, 21, 22, 23 | 39, 40 | 56, 57, 58, 59 | 71, 72 |
| Light chain V domain | 24 | 41 | 60 | 73 |
| scFv | 25, 26, 27, 28 | 42, 43 | | |
| scFv linker | 29 | 29 | | |

TABLE 3 sequences
mAb9 (KSAb1) heavy chain

| | CDR1 | CDR2 | CDR3 |
|---|---|---|---|
| mAb9Vh1 | | | |
| Amino acid sequence | AYTMN SEQ ID NO: 1 | LINPYNGGTNYNQEFEG SEQ ID NO: 3 | RDWDYFDY SEQ ID NO: 4 |
| Nucleotide sequence | gcctacaccatgaac SEQ ID NO: 37 | cttattaatccttacaatggtggtactaactacaaccaggagttcgagggc SEQ ID NO: 39 | agggactgggactactttgactac SEQ ID NO: 40 |
| mAb9Vh2 | | | |
| Amino acid sequence | AYTMN SEQ ID NO: 1 | LINPYNGGTNYNQEFEG SEQ ID NO: 3 | RDWDYFDY SEQ ID NO: 4 |
| Nucleotide sequence | gcctacaccatgaac SEQ ID NO: 37 | cttattaatccttacaatggtggtactaactacaaccaggagttcgagggc SEQ ID NO: 39 | agggactgggactactttgactac SEQ ID NO: 40 |

TABLE 3-continued mAb9Vh3

| | | | |
|---|---|---|---|
| Amino acid sequence | AYTMD SEQ ID NO: 2 | LINPYNGGTNYNQEFEG SEQ ID NO: 3 | RDWDYFDY SEQ ID NO: 4 |
| Nucleotide sequence | gcctacaccatggac SEQ ID NO: 38 | cttattaatccttacaatggtggtactaactacaaccaggagttcgagggc SEQ ID NO: 39 | agggactgggactactttgactac SEQ ID NO: 40 | mAb9Vh4

| | | | |
|---|---|---|---|
| Amino acid sequence | AYTMN SEQ ID NO: 1 | LINPYNGGTNYNQEFEG SEQ ID NO: 3 | RDWDYFDY SEQ ID NO: 4 |
| Nucleotide sequence | gcctacaccatgaac SEQ ID NO: 37 | cttattaatccttacaatggtggtactaactacaaccaggagttcgagggc SEQ ID NO: 39 | agggactgggactactttgactac SEQ ID NO: 40 |

| | Fab heavy chain amino acid sequence | Fab heavy chain nucleotide sequence |
|---|---|---|
| mAb9Vh1 | EVQLQQSGPELVKPGASMKISCKASGYSFSAYTMNWV KQSHGKNLEWIGLINPYNGGTNYNQEFEGKATLTVNK SSNTAFMELLSLTSDDSAVYYCARRDWDYFDYWGQGT TLTVSSAKTTTPPSVYPLAPGCGDTTGSSVTLGCLVKG YFPESVTVTWNSGSLSSSVHTFPALLQSGLYTMSSSV TVPSSTWPSQTVTCSVAHPASSTKVDKKIETRC SEQ ID NO: 8 | GAGGTCCAGCTGCAACAGTCTGGACCTGAGCTGGTGAAGCCT GGAGCTTCAATGAAGATATCCTGCAAGGCTTCTGGTTACTCAT TCTCTGCCTACACCATGAACTGGGTGAAGCAGAGCCATGGAA AGAACCTTGAGTGGATTGGACTTATTAATCCTTACAATGGTGG TACTAACTACAACCAGGAGTTCGAGGGCAAGGCCACTTTAACT GTAAACAAGTCATCCAACACAGCCTTCATGGAGCTCCTCAGTC TGACATCTGACGACTCTGCAGTCTATTACTGTGCGAGAAGGGA CTGGGACTACTTTGACTACTGGGGCCAAGGCACCACTCTCACA GTCTCCTCAGCCAAAACAACAACCCCCATCAGTCTATCCACTGG CCCCTGGGTGTGGAGATACAACTGGTTCCTCCGTGACTCTGGG ATGCCTGGTCAAGGGCTACTTCCCTGAGTCAGTGACTGTGACT TGGAACTCTGGATCCCTGTCCAGCAGTGTGCACACCTTCCCAG CTCTCCTGCAGTCTGGACTCTACACTATGAGCAGCTCAGTGAC TGTCCCCTCCAGCACCTGGCCAAGTCAGACCGTCACCTGCAGC GTTGCTCACCCAGCCAGCAGCACCAAGGTGGACAAGAAAATT GAGACGCGTTGT SEQ ID NO: 44 |
| mAb9Vh2 | EVQLQQSGPELVKPGASMKISCKASGYSFFAYTMNWV KQSHGKNLEWIGLINPYNGGTNYNQEFEGKATLTVNK SSNTAFMELLSLTSDDSAVYYCARRDWDYFDYWGQGT TLTVSSAKTTPPSVYPLAPGCGDTTGSSVTLGCLVKG YFPESVTVTWNSGSLSSSVHTFPALLQSGLYTMSSSV TVPSSTWPSQTVTCSVAHPASSTKVDKKIETRC SEQ ID NO: 9 | GAGGTCCAGCTGCAACAGTCTGGACCTGAGCTGGTGAAGCCT GGAGCTTCAATGAAGATATCCTGCAAGGCTTCTGGTTACTCAT TCTTTGCCTACACCATGAACTGGGTGAAGCAGAGCCATGGAA AGAACCTTGAGTGGATTGGACTTATTAATCCTTACAATGGTGG TACTAACTACAACCAGGAGTTCGAGGGCAAGGCCACTTTAACT GTAAACAAGTCATCCAACACAGCCTTCATGGAGCTCCTCAGTC TGACATCTGACGACTCTGCAGTCTATTACTGTGCGAGAAGGGA CTGGGACTACTTTGACTACTGGGGCCAAGGCACCACTCTCACA GTCTCCTCAGCCAAAACAACAACCCCCATCAGTCTATCCACTGG CCCCTGGGTGTGGAGATACAACTGGTTCCTCCGTGACTCTGGG ATGCCTGGTCAAGGGCTACTTCCCTGAGTCAGTGACTGTGACT TGGAACTCTGGATCCCTGTCCAGCAGTGTGCACACCTTCCCAG CTCTCCTGCAGTCTGGACTCTACACTATGAGCAGCTCAGTGAC TGTCCCCTCCAGCACCTGGCCAAGTCAGACCGTCACCTGCAGC GTTGCTCACCCAGCCAGCAGCACCAAGGTGGACAAGAAAATT GAGACGCGTTGT SEQ ID NO: 45 |
| mAb9Vh3 | EVQLQQSGPELVKPGASMKISCKASGYSFSAYTMDWV KQSHGKNLEWIGLINPYNGGTNYNQEFEGKATLTVNK SSNTAFMELLSLTSDDSAVYYCARRDWDYFDYWGQGT TLTVSSAKTTPPSVYPLAPGCGDTTGSSVTLGCLVKG YFPESVTVTWNSGSLSSSVHTFPALLQSGLYTMSSSV TVPSSTWPSQTVTCSVAHPASSTKVDKKIETRC SEQ ID NO: 10 | GAGGTCCAGCTGCAACAGTCTGGACCTGAGCTGGTGAAGCCT GGAGCTTCAATGAAGATATCCTGCAAGGCTTCTGGTTACTCAT TCTCTGCCTACACCATGGACTGGGTGAAGCAGAGCCATGGAA AGAACCTTGAGTGGATTGGACTTATTAATCCTTACAATGGTGG TACTAACTACAACCAGGAGTTCGAGGGCAAGGCCACTTTAACT GTAAACAAGTCATCCAACACAGCCTTCATGGAGCTCCTCAGTC TGACATCTGACGACTCTGCAGTCTATTACTGTGCGAGAAGGGA CTGGGACTACTTTGACTACTGGGGCCAAGGCACCACTCTCACA GTCTCCTCAGCCAAAACAACAACCCCCATCAGTCTATCCACTGG CCCCTGGGTGTGGAGATACAACTGGTTCCTCCGTGACTCTGGG ATGCCTGGTCAAGGGCTACTTCCCTGAGTCAGTGACTGTGACT TGGAACTCTGGATCCCTGTCCAGCAGTGTGCACACCTTCCCAG CTCTCCTGCAGTCTGGACTCTACACTATGAGCAGCTCAGTGAC TGTCCCCTCCAGCACCTGGCCAAGTCAGACCGTCACCTGCAGC GTTGCTCACCCAGCCAGCAGCACCAAGGTGGACAAGAAAATT GAGACGCGTTGT SEQ ID NO: 46 |
| mAb9Vh4 | EVQLQQSGPELVKPGASMKISCKASGYSFSAYTMNWV KQSHGKNLEWIGLINPYNGGTNYNQEFEGKATLTVNK SSNTAFMELLSLTSDGSAVYYCARRDWDYFDYWGQGT | GAGGTCCAGCTGCAACAGTCTGGACCTGAGCTGGTGAAGCCT GGAGCTTCAATGAAGATATCCTGCAAGGCTTCTGGTTACTCAT TCTCTGCCTACACCATGAACTGGGTGAAGCAGAGCCATGGAA |

TABLE 3-continued

| | | |
|---|---|---|
| | TLTVSSAKTTPPSVYPLAPGCGDTTGSSVTLGCLVKG<br>YFPESVTVTWNSGSLSSSVHTFPALLQSGLYTMSSSV<br>TVPSSTWPSQTVTCSVAHPASSTKVDKKIETRC<br>SEQ ID NO: 11 | AGAACCTTGAGTGGATTGGACTTATTAATCCTTACAATGGTGG<br>TACTAACTACAACCAGGAGTTCGAGGGCAAGGCCACTTTAACT<br>GTAAACAAGTCATCCAACACAGCCTTCATGGAGCTCCTCAGTC<br>TGACATCTGACGCTCTGCAGTCTATTACTGTGCGAGAAGGGA<br>CTGGGACTACTTTGACTACTGGGGCCAAGGCACCACTCTCACA<br>GTCTCCTCAGCCAAAACAACACCCCCATCAGTCTATCCACTGG<br>CCCCTGGGTGTGGAGATACAACTGGTTCCTCCGTGACTCTGGG<br>ATGCTGGTCAAGGGCTACTTCCCTGAGTCAGTGACTGTGACT<br>TGGAACTCTGGATCCCTGTCCAGCAGTGTGCACACCTTCCCAG<br>CTCTCCTGCAGTCTGGACTCTACACTATGAGCAGCTCAGTGAC<br>TGTCCCCTCAGCACCTGGCCAAGTCAGACCGTCACCTGCAGC<br>GTTGCTCACCCAGCCAGCAGCACCAAGGTGGACAAGAAAATT<br>GAGACGCGTTGT<br>SEQ ID NO: 47 |
| | Variable region amino acid sequence | Variable region nucleotide sequence |
| mAb9Vh1 | EVQLQQSGPELVKPGASMKISCKASGYSFSAYTMNWV<br>KQSHGKNLEWIGLINPYNGGTNYNQEFEGKATLTVNK<br>SSNTAFMELLSLTSDDSAVYYCARRDWDYFDYWGQGT<br>TLTVSS<br>SEQ ID NO: 13 | GAGGTCCAGCTGCAACAGTCTGGACCTGAGCTGGTGAAGCCT<br>GGAGCTTCAATGAAGATATCCTGCAAGGCTTCTGGTTACTCAT<br>TCTCTGCCTACACCATGAACTGGGTGAAGCAGAGCCATGGAA<br>AGAACCTTGAGTGGATTGGACTTATTAATCCTTACAATGGTGG<br>TACTAACTACAACCAGGAGTTCGAGGGCAAGGCCACTTTAACT<br>GTAAACAAGTCATCCAACACAGCCTTCATGGAGCTCCTCAGTC<br>TGACATCTGACGACTCTGCAGTCTATTACTGTGCGAGAAGGGA<br>CTGGGACTACTTTGACTACTGGGGCCAAGGCACCACTCTCACA<br>GTCTCCTCA<br>SEQ ID NO: 49 |
| mAb9Vh2 | EVQLQQSGPELVKPGASMKISCKASGYSFFAYTMNWV<br>KQSHGKNLEWIGLINPYNGGTNYNQEFEGKATLTVNK<br>SSNTAFMELLSLTSDDSAVYYCARRDWDYFDYWGQGT<br>TLTVSS<br>SEQ ID NO: 14 | GAGGTCCAGCTGCAACAGTCTGGACCTGAGCTGGTGAAGCCT<br>GGAGCTTCAATGAAGATATCCTGCAAGGCTTCTGGTTACTCAT<br>TCTTTGCCTACACCATGAACTGGGTGAAGCAGAGCCATGGAA<br>AGAACCTTGAGTGGATTGGACTTATTAATCCTTACAATGGTGG<br>TACTAACTACAACCAGGAGTTCGAGGGCAAGGCCACTTTAACT<br>GTAAACAAGTCATCCAACACAGCCTTCATGGAGCTCCTCAGTC<br>TGACATCTGACGACTCTGCAGTCTATTACTGTGCGAGAAGGGA<br>CTGGGACTACTTTGACTACTGGGGCCAAGGCACCACTCTCACA<br>GTCTCCTCA<br>SEQ ID NO: 50 |
| mAb9Vh3 | EVQLQQSGPELVKPGASMKISCKASGYSFSAYTMDWV<br>KQSHGKNLEWIGLINPYNGGTNYNQEFEGKATLTVNK<br>SSNTAFMELLSLTSDDSAVYYCARRDWDYFDYWGQGT<br>TLTVSS<br>SEQ ID NO: 15 | GAGGTCCAGCTGCAACAGTCTGGACCTGAGCTGGTGAAGCCT<br>GGAGCTTCAATGAAGATATCCTGCAAGGCTTCTGGTTACTCAT<br>TCTCTGCCTACACCATGGACTGGGTGAAGCAGAGCCATGGAA<br>AGAACCTTGAGTGGATTGGACTTATTAATCCTTACAATGGTGG<br>TACTAACTACAACCAGGAGTTCGAGGGCAAGGCCACTTTAACT<br>GTAAACAAGTCATCCAACACAGCCTTCATGGAGCTCCTCAGTC<br>TGACATCTGACGACTCTGCAGTCTATTACTGTGCGAGAAGGGA<br>CTGGGACTACTTTGACTACTGGGGCCAAGGCACCACTCTCACA<br>GTCTCCTCA<br>SEQ ID NO: 51 |
| mAb9Vh4 | EVQLQQSGPELVKPGASMKISCKASGYSFSAYTMNWV<br>KQSHGKNLEWIGLINPYNGGTNYNQEFEGKATLTVNK<br>SSNTAFMELLSLTSDGSAVYYCARRDWDYFDYWGQGT<br>TLTVSS<br>SEQ ID NO: 16 | GAGGTCCAGCTGCAACAGTCTGGACCTGAGCTGGTGAAGCCT<br>GGAGCTTCAATGAAGATATCCTGCAAGGCTTCTGGTTACTCAT<br>TCTCTGCCTACACCATGAACTGGGTGAAGCAGAGCCATGGAA<br>AGAACCTTGAGTGGATTGGACTTATTAATCCTTACAATGGTGG<br>TACTAACTACAACCAGGAGTTCGAGGGCAAGGCCACTTTAACT<br>GTAAACAAGTCATCCAACACAGCCTTCATGGAGCTCCTCAGTC<br>TGACATCTGACGGCTCTGCAGTCTATTACTGTGCGAGAAGGGA<br>CTGGGACTACTTTGACTACTGGGGCCAAGGCACCACTCTCACA<br>GTCTCCTCA<br>SEQ ID NO: 52 |

| | mAb9 (KSAb1) light chain | | |
|---|---|---|---|
| | CDR1 | CDR2 | CDR3 |
| mAb9Vk4 | | | |
| Amino acid<br>sequence | KASQNVGTFVA<br>SEQ ID NO: 5 | SASNRYT<br>SEQ ID NO: 6 | RQYSSYPYT<br>SEQ ID NO: 7 |
| Nucleotide<br>sequence | aaggccagtcagaatgtgggtactttttgtagcc<br>SEQ ID NO: 41 | tcggcatccaatcggtacact<br>SEQ ID NO: 42 | cggcaatatagcagctatccgtacacg<br>SEQ ID NO: 43 |
| | Fab light chain amino acid sequence | Fab light chain nucleotide sequence | |
| mAb9Vk4 | DIVMTQSQKFMSTSVGDRVSIICKASQNVGTFVAWYQQ<br>KPGQSPKLLVYSASNRYTGVPDRFTGSGSGTDFTLTIN<br>NMQSEDLADYFCRQYSSYPYTFGGGTKLEIKRADAAPT<br>VSIFPPSSEQLTSGGASVVCFLNNFYPKDINVKWKIVG<br>SERQNGVLNSWTDQDSKDSTYSMSSTLTLTKDEYERHN | GACATTGTGATGACCCAGTCTCAAAAATTCATGTCCACATCAG<br>TAGGAGACAGGGTCAGCATCATTTGCAAGGCCAGTCAGAATG<br>TGGGTACTTTTGTAGCCTGGTATCAACAGAAACCAGGACAATC<br>TCCTAAACTACTGGTTTACTCGGCATCCAATCGGTACACTGGA<br>GTCCCTGATCGCTTCACAGGCAGTGGATCTGGGACAGATTTCA | |

TABLE 3-continued

| | | |
|---|---|---|
| | SYTCEATHKTSTSPIVKSFNRNETRC<br>SEQ ID NO: 12 | CTCTCACCATCAACAATATGCAGTCTGAAGACCTGGCAGATTA<br>TTTCTGCCGGCAATATAGCAGCTATCCGTACACGTTCGGAGGG<br>GGGACCAAGCTAGAAATAAAACGGGCTGATGCTGCACCAACT<br>GTATCCATCTTCCCACCATCCAGTGAGCAGTTAACATCTGGAG<br>GTGCCTCAGTCGTGTGCTTCTTGAACAACTTCTACCCCAAAGA<br>CATCAATGTCAAGTGGAAGATTGTTGGCAGTGAACGACAAAA<br>TGGCGTCCTGAACAGTTGGACTGATCAGGACAGCAAAGACAG<br>CACCTACAGCATGAGCAGCACCCTCACGTTGACCAAGGACGA<br>GTATGAACGACATAACAGCTATACCTGTGAGGCCACTCACAA<br>GACATCAACTTCACCCATTGTCAAGAGCTTCAACAGGAATGAG<br>ACGCGTTGT<br>SEQ ID NO: 48 |
| | Variable region amino acid sequence | Variable region nucleotide sequence |
| mAb9Vk4 | DIVMTQSQKFMSTSVGDRVSIICKASQNVGTFVAWYQQ<br>KPGQSPKLLVYSASNRYTGVPDRFTGSGSGTDFTLTIN<br>NMQSEDLADYFCRQYSSYPYTFGGGTKLEI<br>SEQ ID NO: 17 | GACATTGTGATGACCCAGTCTCAAAAATTCATGTCCACATCAG<br>TAGGAGACAGGGTCAGCATCATTTGCAAGGCCAGTCAGAATG<br>TGGGTACTTTTGTAGCCTGGTATCAACAGAAACCAGGACAATC<br>TCCTAAACTACTGGTTTACTCGGCATCCAATCGGTACACTGGA<br>GTCCCTGATCGCTTCACAGGCAGTGGATCTGGGACAGATTTCA<br>CTCTCACCATCAACAATATGCAGTCTGAAGACCTGGCAGATTA<br>TTTCTGCCGGCAATATAGCAGCTATCCGTACACGTTCGGAGGG<br>GGGACCAAGCTAGAAATA<br>SEQ ID NO: 53 |

ScFv sequences (light - linker - heavy)

GGGGSGGGGSGGGGS - LINKER PEPTIDE
SEQ ID NO: 22 with Vh1

DIVMTQSQKFMSTSVGDRVSIICKASQNVGTFVAWYQQKPGQSPKLLVYSASNRYTGVPDRFTGSGSGTDFTLTINNMQSEDLADYFCRQYSSYPYTFGG
GTKLEIGGGGSGGGGSGGGGSEVQLQQSGPELVKPGASMKISCKASGYSFSAYTMNWVKQSHGKNLEWIGLINPYNGGTNYNQEFEGKATLTVNKSSNTA
FMELLSLTSDDSAVYYCARRDWDYFDYWGQGTTLTVSS
SEQ ID NO: 18 with Vh2

DIVMTQSQKFMSTSVGDRVSIICKASQNVGTFVAWYQQKPGQSPKLLVYSASNRYTGVPDRFTGSGSGTDFTLTINNMQSEDLADYFCRQYSSYPYTFGG
GTKLEIGGGGSGGGGSGGGGSEVQLQQSGPELVKPGASMKISCKASGYSFFAYTMNWVKQSHGKNLEWIGLINPYNGGTNYNQEFEGKATLTVNKSSNTA
FMELLSLTSDDSAVYYCARRDWDYFDYWGQGTTLTVSS
SEQ ID NO: 19 with Vh3

DIVMTQSQKFMSTSVGDRVSIICKASQNVGTFVAWYQQKPGQSPKLLVYSASNRYTGVPDRFTGSGSGTDFTLTINNMQSEDLADYFCRQYSSYPYTFGG
GTKLEIGGGGSGGGGSGGGGSEVQLQQSGPELVKPGASMKISCKASGYSFSAYTMDWVKQSHGKNLEWIGLINPYNGGTNYNQEFEGKATLTVNKSSNTA
FMELLSLTSDDSAVYYCARRDWDYFDYWGQGTTLTVSS
SEQ ID NO: 20 with Vh4

DIVMTQSQKFMSTSVGDRVSIICKASQNVGTFVAWYQQKPGQSPKLLVYSASNRYTGVPDRFTGSGSGTDFTLTINNMQSEDLADYFCRQYSSYPYTFGG
GTKLEIGGGGSGGGGSGGGGSEVQLQQSGPELVKPGASMKISCKASGYSFSAYTMNWVKQSHGKNLEWIGLINPYNGGTNYNQEFEGKATLTVNKSSNTA
FMELLSLTSDGSAVYYCARRDWDYFDYWGQGTTLTVSS
SEQ ID NO: 21
GACATTGTGATGACCCAGTCTCAAAAATTCATGTCCACATCAGTAGGAGACAGGGTCAGCATCATTTGCAAGGCCAGTCAGAAT
GTGGGTACTTTTGTAGCCTGGTATCAACAGAAACCAGGACAATCTCCTAAACTACTGGTTTACTCGGCATCCAATCGGTACACTG mAb17 (KSAb2) heavy chain

| | CDR1 | CDR2 | CDR3 |
|---|---|---|---|
| Mab17Vh1 | | | |
| Amino acid sequence | AYTMN<br>SEQ ID NO: 1 | LINPYNGGTSYNQKFED<br>SEQ ID NO: 23 | RDWDYFDY<br>SEQ ID NO: 4 |
| Nucleotide sequence | gcctacaccatgaac<br>SEQ ID NO: 37 | cttattaatccatacaatggtggtactagctacaaccagaagttcgaggac<br>SEQ ID NO: 54 | agggactgggactactttgactac<br>SEQ ID NO: 40 |
| Mab17Vh2 | | | |
| Amino acid sequence | AYTMN<br>SEQ ID NO: 1 | LINPYNGGTNYNQKFED<br>SEQ ID NO: 24 | RDWDYFDY<br>SEQ ID NO: 4 |

TABLE 3-continued

| | | | |
|---|---|---|---|
| Nucleotide sequence | gcctacaccatgaac SEQ ID NO: 37 | cttattaatccttacaatggtggtactaactacaaccagaagttcgaggac SEQ ID NO: 55 | agggactgggactactttgactac SEQ ID NO: 40 |

Mab17Vh3

| | | | |
|---|---|---|---|
| Amino acid sequence | AYTMN SEQ ID NO: 1 | LINPYNGGTNYNQKFED SEQ ID NO: 24 | RDWDYFDY SEQ ID NO: 4 |
| Nucleotide sequence | gcctacaccatgaac SEQ ID NO: 37 | cttattaatccttacaatggtggtactaactacaaccagaagttcgaggac SEQ ID NO: 55 | agggactgggactactttgactac SEQ ID NO: 40 |

Mab17Vh4

| | | | |
|---|---|---|---|
| Amino acid sequence | AYTMN SEQ ID NO: 1 | LINPYNGGTNYNQKFED SEQ ID NO: 24 | RDWDYFDY SEQ ID NO: 4 |
| Nucleotide sequence | gcctacaccatgaac SEQ ID NO: 37 | cttattaatccttacaatggtggtactaactacaaccagaagttcgaggac SEQ ID NO: 55 | agggactgggactactttgactac SEQ ID NO: 40 |

| | Fab heavy chain amino acid sequence | Fab heavy chain nucleotide sequence |
|---|---|---|
| mAb17Vh1 | EVQLQQSGPELVKPGASMKISCKASGYSFTAYTMNWV KQTHGKNLEWIGLINPYNGGTSYNQKFEDKATLTVDK SSNTAYMDLLSLTSEDSAVYYCARRDWDYFDYWGQGT TLTVSSAKTTAPAVYPLAPVCGDTTGSSVTLGCLVKG YFPEPVTLTWNSGSLSSGVHTFPAVLQSDLYTLSSSV TVTSSTWPSQSITCNVAHPASSTKVDKKIETRC SEQ ID NO: 28 | GAGGTCCAGCTGCAACAGTCTGGACCTGAGCTGGTGAAGCCT GGAGCTTCAATGAAGATATCCTGCAAGGCTTCTGGTTACTCAT TCACTGCCTACACCATGAACTGGGTGAAGCAGACCCATGGAA AGAACCTTGAGTGGATTGGACTTATTAATCCATACAATGGTGG TACTAGCTACAACCAGAAGTTCGAGGACAAGGCCACATTAAC TGTTGACAAGTCATCCAACACAGCCTACATGGACCTCCTCAGT CTGACATCTGAGGACTCTGCAGTCTATTATTGTGCAAGAAGGG ACTGGGACTACTTTGACTACTGGGGCCAAGGCACCACTCTCAC AGTCTCCTCAGCCAAAACAACAGCCCCAGCGGTCTATCCACTG GCCCCTGTGTGTGGAGATACGACTGGCTCCTCGGTGACTCTAG GATGCCTGGTCAAGGGTTATTTCCCTGAGCCAGTGACCTTGAC CTGGAACTCTGGATCCCTGTCCAGTGGTGTGCACACCTTCCCA GCTGTCCTGCAGTCTGACCTCTACACCCTCAGCAGCTCAGTGA CTGTAACCTCGAGCACCTGGCCCAGCCAGTCCATCACCTGCAA TGTGGCCCACCCGGCAAGCAGCACCAAGGTGGACAAGAAAAT TGAGACGCGTTGT SEQ ID NO: 59 |
| mAb17Vh2 | EVQLQQSGPELVKPGASMKISCKASGYSFTAYTMNWV KQTHGKNLEWIGLINPYNGGTNYNQKFEDKATLTVDK SSNTAYMDLLSLTSEDSAVYYCARRDWDYFDYWGQGT TLTVSSAKTTAPSVYPLAPVCGDTTGSSVTLGCLVKG YFPEPVTLTWNSGSLSSGVHTFPAVLQSDLYTLSSSV TVTSSTWPSQSITCNVAHPASSTKVDKKIETRC SEQ ID NO: 29 | GAGGTCCAGCTGCAACAGTCTGGACCTGAGCTGGTGAAGCCT GGAGCTTCAATGAAGATATCCTGCAAGGCTTCTGGTTACTCAT TCACTGCCTACACCATGAACTGGGTGAAGCAGACCCATGGAA AGAACCTTGAGTGGATTGGACTTATTAATCCTTACAATGGTGG TACTAACTACAACCAGAAGTTCGAGGACAAGGCCACATTAAC TGTCGACAAGTCATCCAACACAGCCTACATGGACCTCCTCAGT CTGACATCTGAGGACTCTGCAGTCTATTATTGTGCAAGAAGGG ACTGGGACTACTTTGACTACTGGGGCCAAGGCACCACTCTCAC AGTCTCCTCAGCCAAAACAACAGCCCCATCGGTCTATCCACTG GCCCCTGTGTGTGGAGATACAACTGGCTCCTCGGTGACTCTAG GATGCCTGGTCAAGGGTTATTTCCCTGAGCCAGTGACCTTGAC CTGGAACTCTGGATCCCTGTCCAGTGGTGTGCACACCTTCCCA GCTGTCCTGCAGTCTGACCTCTACACCCTCAGCAGCTCAGTGA CTGTAACCTCGAGCACCTGGCCCAGCCAGTCCATCACCTGCAA TGTGGCCCACCCGGCAAGCAGCACCAAGGTGGACAAGAAAAT TGAGACGCGTTGT SEQ ID NO: 60 |
| mAb17Vh3 | EVQLQQSGPELVKPGASMKISCKASGYSFTAYTMNWV KQTHGKNLEWIGLINPYNGGTNYNQKFEDKATLTVDK SSNTAYMDLLSLTSEDSAVYYCARRDWDYFDYWGQGT TLTVSSAKTTAPSVYPLAPVCGDTTGSSVTLGCLVKG YFPEPVTLTWNSGSLSSGVHT SEQ ID NO: 30 | GAGGTCCAGCTGCAACAGTCTGGACCTGAGCTGGTGAAGCCT GGAGCTTCAATGAAGATATCCTGCAAGGCTTCTGGTTACTCAT TCACTGCCTACACCATGAACTGGGTGAAGCAGACCCATGGAA AGAACCTTGAGTGGATTGGACTTATTAATCCTTACAATGGTGG TACTAACTACAACCAGAAGTTCGAGGACAAGGCCACATTAAC TGTCGACAAGTCATCCAACACAGCCTACATGGACCTCCTCAGT CTGACATCTGAGGACTCTGCAGTCTATTATTGTGCAAGAAGGG ACTGGGACTACTTTGACTACTGGGGCCAAGGCACCACTCTCAC AGTCTCCTCAGCCAAAACAACAGCCCCATCGGTCTATCCACTG GCCCCTGTGTGTGGAGATACAACTGGCTCCTCGGTGACTCTAG GATGCCTGGTCAAGGGTTATTTCCCTGAGCCAGTGACCTTGAC CTGGAACTCTGGATCCCTGTCCAGTGGTGTGCACACC SEQ ID NO: 61 |
| mAb17Vh4 | EVQLQQSGPELVKPGASMKISCKASGYSFTAYTMNWV KQTHGKNLEWIGLINPYNGGTNYNQKFEDKATLTVDK SSNTAYMDLLSLTSEDSAVYYCARRDWDYFDYWGQGT TLTVSSAKTTAPSVYPLAPVCGDTTGSSVTLGCLVKG | GAGGTCCAGCTGCAACAGTCTGGACCTGAGCTGGTGAAGCCT GGAGCTTCAATGAAGATATCCTGCAAGGCTTCTGGTTACTCAT TCACTGCCTACACCATGAACTGGGTGAAGCAGACCCATGGAA AGAACCTTGAGTGGATTGGACTTATTAATCCTTACAATGGTGG |

TABLE 3-continued

| | | |
|---|---|---|
| | YFPEPVTLTWNSGSLSSGVHT<br>SEQ ID NO: 30 | TACTAACTACAACCAGAAGTTCGAGGACAAGGCCACATTAAC<br>TGTCGACAAGTCATCCAACACAGCCTACATGGACCTCCTCAGT<br>CTGACATCTGAGGACTCTGCAGTCTATTATTGTGCAAGAAGGG<br>ACTGGGACTACTTTGACTACTGGGGCCAAGGCACCACTCTCAC<br>AGTCTCCTCAGCCAAAACAACAGCCCCATCGGTCTATCCACTG<br>GCCCCTGTGTGTGGAGATACAACTGGCTCCTCGGTGACTCTAG<br>GATGCCTGGTCAAGGGTTATTTCCCTGAGCCAGTGACCTTGAC<br>CTGGAACTCTGGATCCCTGTCCAGTGGTGTGCACACC<br>SEQ ID NO: 62 |

| | Variable region amino acid sequence | Variable region nucleotide sequence |
|---|---|---|
| mAb17Vh1 | EVQLQQSGPELVKPGASMKISCKASGYSFTAYTMNWV<br>KQTHGKNLEWIGLINPYNGGTSYNQKFEDKATLTVDK<br>SSNTAYMDLLSLTSEDSAVYYCARRDWDYFDYWGQGT<br>TLTVSS<br>SEQ ID NO: 32 | GAGGTCCAGCTGCAACAGTCTGGACCTGAGCTGGTGAAGCCT<br>GGAGCTTCAATGAAGATATCCTGCAAGGCTTCTGGTTACTCAT<br>TCACTGCCTACACCATGAACTGGGTGAAGCAGACCCATGGAA<br>AGAACCTTGAGTGGATTGGACTTATTAATCCATACAATGGTGG<br>TACTAGCTACAACCAGAAGTTCGAGGACAAGGCCACATTAAC<br>TGTTGACAAGTCATCCAACACAGCCTACATGGACCTCCTCAGT<br>CTGACATCTGAGGACTCTGCAGTCTATTATTGTGCAAGAAGGG<br>ACTGGGACTACTTTGACTACTGGGGCCAAGGCACCACTCTCAC<br>AGTCTCCTCA<br>SEQ ID NO: 64 |
| mAb17Vh2 | EVQLQQSGPELVKPGASMKISCKASGYSFTAYTMNWV<br>KQTHGKNLEWIGLINPYNGGTNYNQKFEDKATLTVDK<br>SSNTAYMDLLSLTSEDSAVYYCARRDWDYFDYWGQGT<br>TLTVSS<br>SEQ ID NO: 32 | GAGGTCCAGCTGCAACAGTCTGGACCTGAGCTGGTGAAGCCT<br>GGAGCTTCAATGAAGATATCCTGCAAGGCTTCTGGTTACTCAT<br>TCACTGCCTACACCATGAACTGGGTGAAGCAGACCCATGGAA<br>AGAACCTTGAGTGGATTGGACTTATTAATCCTTACAATGGTGG<br>TACTAACTACAACCAGAAGTTCGAGGACAAGGCCACATTAAC<br>TGTCGACAAGTCATCCAACACAGCCTACATGGACCTCCTCAGT<br>CTGACATCTGAGGACTCTGCAGTCTATTATTGTGCAAGAAGGG<br>ACTGGGACTACTTTGACTACTGGGGCCAAGGCACCACTCTCAC<br>AGTCTCCTCA<br>SEQ ID NO: 64 |
| mAb17Vh3 | EVQLQQSGPELVKPGAsMKISCKASGYSFTAYTMNWV<br>KQTHGKNLEWIGLINPYNGGTNYNQKFEDKATLTVDK<br>SSNTAYMDLLSLTSEDSAVYYCARRDWDYFDYWGQGT<br>TLTVSS<br>SEQ ID NO: 33 | GAGGTCCAGCTGCAACAGTCTGGACCTGAGCTGGTGAAGCCT<br>GGAGCTTCAATGAAGATATCCTGCAAGGCTTCTGGTTACTCAT<br>TCACTGCCTACACCATGAACTGGGTGAAGCAGACCCATGGAA<br>AGAACCTTGAGTGGATTGGACTTATTAATCCTTACAATGGTGG<br>TACTAACTACAACCAGAAGTTCGAGGACAAGGCCACATTAAC<br>TGTCGACAAGTCATCCAACACAGCCTACATGGACCTCCTCAGT<br>CTGACATCTGAGGACTCTGCAGTCTATTATTGTGCAAGAAGGG<br>ACTGGGACTACTTTGACTACTGGGGCCAAGGCACCACTCTCAC<br>AGTCTCCTCA<br>SEQ ID NO: 65 |
| mAb17Vh4 | EVQLQQSGPELVKPGASMKISCKASGYSFTAYTMNWV<br>KQTHGKNLEWIGLINPYNGGTNYNQKFEDKATLTVDK<br>SSNTAYMDLLSLTSEDSAVYYCARRDWDYFDYWGQGT<br>TLTVSS<br>SEQ ID NO: 33 | GAGGTCCAGCTGCAACAGTCTGGACCTGAGCTGGTGAAGCCT<br>GGAGCTTCAATGAAGATATCCTGCAAGGCTTCTGGTTACTCAT<br>TCACTGCCTACACCATGAACTGGGTGAAGCAGACCCATGGAA<br>AGAACCTTGAGTGGATTGGACTTATTAATCCTTACAATGGTGG<br>TACTAACTACAACCAGAAGTTCGAGGACAAGGCCACATTAAC<br>TGTCGACAAGTCATCCAACACAGCCTACATGGACCTCCTCAGT<br>CTGACATCTGAGGACTCTGCAGTCTATTATTGTGCAAGAAGGG<br>ACTGGGACTACTTTGACTACTGGGGCCAAGGCACCACTCTCAC<br>AGTCTCCTCA<br>SEQ ID NO: 65 |

| mAb17 (KSAb2) light chain | | |
|---|---|---|
| | CDR1 | CDR2 | CDR3 |

| Mab17Vk4 | | | |
|---|---|---|---|
| Amino acid<br>sequence | KASQNVGTALA<br>SEQ ID NO: 25 | SASNRNT<br>SEQ ID NO: 26 | QQYSSYPYT<br>SEQ ID NO: 27 |
| Nucleotide<br>sequence | aaggccagtcagaatgtgggtactgctttagcc<br>SEQ ID NO: 56 | tcggcatccaatcggaacact<br>SEQ ID NO: 57 | cagcaatatagcagctatccttacacg<br>SEQ ID NO: 58 |

| | Fab light chain amino acid sequence | Fab light chain nucleotide sequence |
|---|---|---|
| mAb17Vk4 | DVVMTQSQKFLSTSAGDRVSISCKASQNVGTALAWYQQ<br>KPGQSPKLLIYSASNRNTGVPDRFTGRGFGTDFTLTIS<br>NMQSEDLADYFCQQYSSYPYTFGGGTRLEIKRADAAPT<br>VSIFPPSSEQLTSGGASVVCFLNNFYPKDINVKWKIDG<br>SERQNGVLNSWTDQDSKDSTYSMSSTLTLTKDEYERHN<br>SYTCEATHKTSTSPIVKSFNRNETRC<br>SEQ ID NO: 31 | GACGTTGTGATGACCCAGTCTCAAAAATTCCTGTCCACATCAG<br>CAGGAGACAGGGTCAGCATCTCCTGCAAGGCCAGTCAGAATG<br>TGGGTACTGCTTTAGCCTGGTATCAACAGAAACCAGGACAATC<br>TCCTAAACTTTTGATTTACTCGGCATCCAATCGGAACACTGGA<br>GTCCCTGATCGCTTCACAGGCAGGGGATTTGGGACAGATTTCA<br>CTCTCACCATCAGCAATATGCAGTCTGAAGCCTGGCAGATTA<br>TTTCTGCCAGCAATATAGCAGCTATCCTTACACGTTCGGAGGG<br>GGGACCAGGCTGGAAATAAAGCGGGCTGATGCTGCACCAACT<br>GTATCCATCTTCCCACCATCCAGTGAGCAGTTAACATCTGGAG |

TABLE 3-continued

|  |  |  |
|---|---|---|
|  |  | GTGCCTCAGTCGTGTGCTTCTTGAACAACTTCTACCCCAAAGA<br>CATCAATGTCAAGTGGAAGATTGATGGCAGTGAACGACAAAA<br>TGGCGTCCTGAACAGTTGGACTGATCAGGACAGCAAAGACAG<br>CACCTACAGCATGAGCAGCACCCTCACGTTGACCAAGGACGA<br>GTATGAACGACATAACAGCTATACCTGTGAGGCCACTCACAA<br>GACATCAACTTCACCCATTGTCAAGAGCTTCAACAGGAATGAG<br>ACGCGTTGT<br>SEQ ID NO: 63 |
|  | Variable region amino acid sequence | Variable region nucleotide sequence |
| mAb17Vk4 | DVVMTQSQKFLSTSAGDRVSISCKASQNVGTALAWYQQ<br>KPGQSPKLLIYSASNRNTGVPDRFTGRGFGTDFTLTIS<br>NMQSEDLADYFCQQYSSYPYTFGGGTRLEI<br>SEQ ID NO: 34 | GACGTTGTGATGACCCAGTCTCAAAAATTCCTGTCCACATCAG<br>CAGGAGACAGGGTCAGCATCTCCTGCAAGGCCAGTCAGAATG<br>TGGGTACTGCTTTAGCCTGGTATCAACAGAAACCAGGACAATC<br>TCCTAAACTTTTGATTTACTCGGCATCCAATGGAACACTGGA<br>GTCCCTGATCGCTTCACAGGCAGGGGATTTGGGACAGATTTCA<br>CTCTCACCATCAGCAATATGCAGTCTGAAGACCTGGCAGATTA<br>TTTCTGCCAGCAATATAGCAGCTATCCTTACACGTTCGGAGGG<br>GGGACCAGGCTGGAAATA<br>SEQ ID NO: 66 |

ScFv sequences (light - linker - heavy)

GGGGSGGGGSGGGGS - LINKER PEPTIDE
SEQ ID NO: 22 with Vh1

DVVMTQSQKFLSTSAGDRVSISCKASQNVGTALAWYQQKPGQSPKLLTYSASNRNTGVPDRFTGRGFGTDFTLTISNMQSEDLADYFCQQYSSYPYTFGG
GTRLEIGGGGSGGGGSGGGGSEVQLQQSGPELVKPGASMKISCKASGYSFTAYTMNWVKQTHGKNLEWIGLINPYNGGTSYNQKFEDKATLTVDKSSNTA
YMDLLSLTSEDSAVYYCARRDWDYFDYWGQGTTLTVSS
SEQ ID NO: 35 with Vh2

DVVMTQSQKFLSTSAGDRVSISCKASQNVGTALAWYQQKPGQSPKLLIYSASNRNTGVPDRFTGRGFGTDFTLTISNMQSEDLADYFCQQYSSYPYTFGG
GTRLEIGGGGSGGGGSGGGGSEVQLQQSGPELVKPGASMKISCKASGYSFTAYTMNWVKQTHGKNLEWIGLINPYNGGTNYNQKFEDKATLTVDKSSNTA
YMDLLSLTSEDSAVYYCARRDWDYFDYWGQGTTLTVSS
SEQ ID NO: 35 with Vh3

DVVMTQSQKFLSTSAGDRVSISCKASQNVGTALAWYQQKPGQSPKLLIYSASNRNTGVPDRFTGRGFGTDFTLTISNMQSEDLADYFCQQYSSYPYTFGG
GTRLEIGGGGSGGGGSGGGGSEVQLQQSGPELVKPGASMKISCKASGYSFTAYTMNWVKQTHGKNLEWIGLINPYNGGTNYNQKFEDKATLTVDKSSNTA
YMDLLSLTSEDSAVYYCARRDWDYFDYWGQGTTLTVSS
SEQ ID NO: 36 with Vh4

DVVMTQSQKFLSTSAGDRVSISCKASQNVGTALAWYQQKPGQSPKLLIYSASNRNTGVPDRFTGRGFGTDFTLTISNMQSEDLADYFCQQYSSYPYTFGG
GTRLEIGGGGSGGGGSGGGGSEVQLQQSGPELVKPGASMKISCKASGYSFTAYTMNWVKQTHGKNLEWIGLINPYNGGTNYNQKFEDKATLTVDKSSNTA
YMDLLSLTSEDSAVYYCARRDWDYFDYWGQGTTLTVSS
SEQ ID NO: 36

References
1. Rao, P. V., P. F. Watson., A. P. Weetman., G. Carayanniotis, and J. P. Banga. 2003. Contrasting activities of thyrotropin receptor antibodies in experimental models of Graves' disease induced by injection of transfected fibroblasts or deoxyribonucleic acid vaccination. Endocrinol. 144: 260-266.
2. Muehlberg, T., J. A. Gilbert., P. V. Rao., A. M. McGregor, and J. P. Banga. 2004. Dynamics of thyroid stimulating and blocking antibodies to the thyrotropin receptor in a murine model of Graves' disease. Endocrinol. 145: 1539-1545.
3. Chen, C. R., P. Pichurin., Y. Nagayama., F. Latrofa., B. Rapoport, and S. M. Mclachlan. 2003. The thyrotropin receptor autoantigen in Graves' disease is the culprit as well as the victim. J. Clin. Invest. 111: 1897-1904.
4. Chen, C. R., P. Pichurin., G. D. Chazenbalk., H. Aliesky., Y. Nagayama., S. M. Mclachlan, and B. Rapoport. 2004. Low dose immunization with adenovirus expressing the thyroid stimulating hormone receptor A-subunit deviates the antibody response toward that of autoantibodies in human Graves' disease. Endocrinol. 145: 228-233.
5. Metcalfe, R., N. Jordan., P. F. Watson., S. Gullu., M. Wiltshire., M. Crisp., C. Evans., A. P. Weetman, and M. Ludgate. 2002. Demonstration of immunoglobulin G, A and E autoantibodies to the human thyrotropin receptor using flow cytometry. J. Clin. Endocrinol. Metab. 87: 1754-1761.
6. Harlow, E., and D. Lane. 1988. Antibodies: A Laboratory manual. Cold Spring Harbor Press.
7. Johnstone, A. P. and R. Thorpe. 1987. Radiolabelling techniques. In Immunochemistry in Practice, 2$^{nd}$ Edition. Johnstone, A. P. and Thorpe, R. eds. Blackwell Scientific Publications, p. 113.
8. Kasagi, K., J. Konishi, Y. Iida., K. Ikekuko., T. Mori., K. Kuma, and K. Torizuka. 1992. A new in vitro assay for thyroid stimulator using cultured thyroid cells: Effect of sodium chloride on adenosine 3',5'-monophosphate increase. J. Clin. Endocrinol. Metab. 54: 108-114.
9. Nicholson, L. B., H. Vlase., P. Graves., M. Nilsson., J. Molne., G. C. Huang., N. G. Morgenthaler., T. F. Davies, A. M. McGregor, and J. P. Banga. 1996. Monoclonal antibodies to the human TSH receptor; epitope mapping and binding to the native receptor on the basolateral plasma membrane of thyroid follicular cells. J. Mol. Endocrinol. 16: 159-170.
10. McLachlan, S. M. and B. Rapoport. 2004. Thyroid stimulating monoclonal antibodies: overcoming the road blocks and the way forward. Clin. Endocrinol. 61: 10-18.
11. Sanders, J., J. Jeffreys., H. Depraetere., M. Evans., T. Richards., A. Kiddie., K. Bretton., L. D. K. E. Premawardhana., D. Y. Chirgadze., R. Nunez Miguel., T. L. Blundell., J. Furmaniak, and B. Rees Smith. 2004. Characteristics of a human monoclonal autoantibody to the thyrotropin receptor: sequence structure and function. Thyroid 14: 560-570.
12. Costagliola, S., M. Bonomi., N. Morgenthaler., J. Van Durme., V. Panneels., S. Refetoff, and G. Vassart. 2004. Delineation of the discontinuous conformational epitope of a monoclonal antibody displaying full in vitro and in vivo thyrotropin activity. Mol. Endocrinol. 18: 3020-3034.
13. Pomerance M, Abdullah H B, Kamerji S, Correze C, Blondeau J P. 2000. Thyroid stimulating hormone and cyclic AMP activatep 38 mitogen-activated protein kinase cascade. J. Biol. Chem. 275: 40539-40546.
14. Noh J Y, Hamada N, Inoue Y, Abe Y, Ito K and K. Ito 2000. Thyroid-stimulating antibody is related to Graves' opthalmopathy, but thyroglobulin-binding inhibitor immunoglobulin is related to hyperthyroidism in patients with Graves'disease. Thyroid 10: 809-813.
15. Costagliola S, Many M-C, Denef J F, Pohlenz J, Refetoff S and G Vassart. 2000. Genetic immunization of outbred mice with thyrotropin receptor cDNA provides a model of Graves' disease. J Clin Invest. 105: 803-811.
16. Denef, J. F., S. Haumont., C. Cornette, and M. F. Van der Hove. 1996. Iodine induced thyroid inhibition and cell necrosis: two consequences of the same free-radical mediated mechanism. Mol. Cell. Endocrinol. 121: 101-103.
17. Riou, C., H. Tonoli., F. Bernier-Valentin., R. Rabilloud., P. Fontlupt, and B. Rousser. 1999. Susceptibility of differentiated thyrocytes in primary culture to undergo apoptosis after exposure to hydrogen peroxide: relation with the level of expression of apoptosis regulatory proteins, Bcl-2 and Bax. Endocrinol. 140: 1990-1997.
18. Ando, T., R. Latif., A. Pritsher., T. Moran., Y. Nagayama, and T. F. Davies. 2002. A monoclonal thyroid stimulating antibody. J. Clin. Invest. 110:1667-1674.
19. Ando, T., R. Latif, and T. F. Davies. 2004. Concentration dependent regulation of thyrotropin receptor function by thyroid stimulating antibody. J. Clin. Invest. 113: 1589-1595.
20. Dromey, J. A., Weenink, S. M., G. H. Peters., J. Endl., P. J. Tighe., I. Todd, and M. R. Christie. 2004. Mapping of epitopes for autoantibodies to the type 1 diabetes autoantigen IA-2 by peptide phage display and molecular modeling: overlap of antibody and T cell determinants. J. Immunol. 172: 4084-4090.

The invention claimed is:

1. An antibody which binds to human thyroid stimulating hormone receptor (TSHR) comprising a heavy chain variable region comprising a first complementarity determining region (CDR) comprising the amino acid sequence of SEQ ID NO: 1 or SEQ ID NO: 2, a second CDR comprising the amino acid sequence of SEQ ID NO: 3, and a third CDR comprising the amino acid sequence of SEQ ID NO: 4 and a light chain variable region comprising first, second and third CDRs comprising SEQ ID NOs: 5-7, respectively.

2. An antibody according to claim 1, wherein said heavy chain variable region comprises an amino acid sequence that is at least 85% identical to SEQ ID NO: 13.

3. An antibody according to claim 1, wherein said light chain variable region comprises an amino acid sequence that is at least 85% identical to SEQ ID NO: 17.

4. An antibody according to claim 1, wherein said heavy chain variable region comprises an amino acid sequence that is at least 85% identical to SEQ ID NO: 13 and wherein said light chain variable region comprises an amino acid sequence that is at least 85% identical to SEQ ID NO: 17.

5. An antibody according to claim 1, wherein said antibody is humanized.

6. An antibody according to claim 1, wherein said antibody is an IgG.

7. An antibody according to claim 1, wherein said antibody is conjugated to an active molecule selected from the group consisting of a detectable tag, an enzymatic tag, a radiolabel, a toxic agent, and another antibody.

8. An antibody according to claim 1, wherein said antibody is conjugated to radioactive iodine.

9. A composition comprising an antibody according to claim 1.

10. A kit comprising an antibody according to claim 1.

11. A nucleic acid molecule encoding an antibody according to claim 1.

12. A vector comprising a nucleic acid molecule according to claim 11.

13. An isolated host cell comprising a vector according to claim 12.

14. A method of generating an antibody according to claim 1, said method comprising culturing a host cell comprising a vector comprising a nucleic acid molecule encoding the antibody under conditions that allow expression of the antibody and isolating the antibody from the culture.

15. An antibody produced by a method according to claim 14.

16. A method of locating tumor cells expressing human thyroid stimulating hormone receptor (TSHR) in a patient comprising:

(a) administering to a patient an antibody according to claim 1, wherein said antibody is conjugated to a radioactive moiety;
(b) scanning the patient for the presence, localisation or accumulation of the radioactive compound; and
(c) generating an image of the patient.

17. The method of claim 16, wherein said radioactive moiety is radioactive iodine.

18. An antibody which binds to human thyroid stimulating hormone receptor (TSHR) comprising a heavy chain variable region comprising a first complementarity determining region (CDR) comprising the amino acid sequence of SEQ ID NO: 1, a second CDR comprising the amino acid sequence of SEQ ID NO: 23 or SEQ ID NO: 24, and a third CDR comprising the amino acid sequence of SEQ ID NO: 4 and a light chain variable region comprising first, second and third CDRs comprising SEQ ID NOs: 25-27, respectively.

19. An antibody according to claim 18, wherein said heavy chain variable region comprises an amino acid sequence that is at least 85% identical to SEQ ID NO: 32.

20. An antibody according to claim 18, wherein said light chain variable region comprises an amino acid sequence that is at least 85% identical to SEQ ID NO: 34.

21. An antibody according to claim 18, wherein said heavy chain variable region comprises an amino acid sequence that is at least 85% identical to SEQ ID NO: 32 and wherein said light chain variable region comprises an amino acid sequence that is at least 85% identical to SEQ ID NO: 34.

22. An antibody according to claim 18, wherein said antibody is humanized.

23. An antibody according to claim 18, wherein said antibody is conjugated to an active molecule selected from the group consisting of a detectable tag, an enzymatic tag, a radiolabel, a toxic agent, and another antibody.

24. An antibody according to claim 18, wherein said antibody is conjugated to radioactive iodine.

25. A composition comprising an antibody according to claim 18.

26. A kit comprising an antibody according to claim 18.

27. A nucleic acid molecule encoding an antibody according to claim 18.

28. A vector comprising a nucleic acid molecule according to claim 27.

29. An isolated host cell comprising a vector according to claim 27.

30. A method of generating an antibody according to claim 18, said method comprising culturing a host cell comprising a vector comprising a nucleic acid molecule encoding the antibody under conditions that allow expression of the antibody and isolating the antibody from the culture.

31. An antibody produced by a method according to claim 30.

32. A method of locating tumor cells expressing human thyroid stimulating hormone receptor (TSHR) in a patient comprising:
(a) administering to a patient an antibody according to claim 18, wherein said antibody is conjugated to a radioactive moiety;
(b) scanning the patient for the presence, localisation or accumulation of the radioactive compound; and
(c) generating an image of the patient.

33. The method of claim 32, wherein said radioactive moiety is radioactive iodine.

34. A hybridoma deposited under ECACC accession number 06032901.

35. An antibody produced by a hybridoma according to claim 34.

36. An antibody which binds to human thyroid stimulating hormone receptor (TSHR) comprising a heavy chain variable region comprising the complementarity determining regions (CDRs) of the heavy chain variable region of an antibody produced by a hybridoma according to claim 34 and a light chain variable region comprising the CDRs of the light chain variable region of an antibody produced by a hybridoma according to claim 34.

37. A hybridoma deposited under ECACC accession number 06032902.

38. An antibody produced by a hybridoma according to claim 37.

39. An antibody which binds to human thyroid stimulating hormone receptor (TSHR) comprising a heavy chain variable region comprising the complementarity determining regions (CDRs) of the heavy chain variable region of an antibody produced by a hybridoma according to claim 37 and a light chain variable region comprising the CDRs of the light chain variable region of an antibody produced by a hybridoma according to claim 37.

* * * * *

UNITED STATES PATENT AND TRADEMARK OFFICE
CERTIFICATE OF CORRECTION

PATENT NO. : 8,603,466 B2  Page 1 of 1
APPLICATION NO. : 12/294760
DATED : December 10, 2013
INVENTOR(S) : Banga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1283 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,603,466 B2  
APPLICATION NO. : 12/294760  
DATED : December 10, 2013  
INVENTOR(S) : Jasvinder-Paul Singh Banga et al.

Page 1 of 1

It is certified that error appears in the above-identified patent and that said Letters Patent is hereby corrected as shown below:

In the claims,

Column 80, Claim 29, Line 60:
Please delete "claim 27." and replace with --claim 28.--

Signed and Sealed this
Eighth Day of March, 2016

Michelle K. Lee
*Director of the United States Patent and Trademark Office*